(12) United States Patent
Chiu et al.

(10) Patent No.: US 10,975,096 B2
(45) Date of Patent: Apr. 13, 2021

(54) SYNTHESIS OF POLYCYCLIC-CARBAMOYLPYRIDONE COMPOUNDS

(71) Applicant: Gilead Sciences, Inc., Foster City, CA (US)

(72) Inventors: Anna Chiu, Burlingame, CA (US); John Enquist, Jr., San Mateo, CA (US); Nolan Griggs, San Mateo, CA (US); Christopher Hale, San Francisco, CA (US); Norihiro Ikemoto, South Plainfield, NJ (US); Katie Ann Keaton, Niwot, CO (US); Matt Kraft, Belmont, CA (US); Scott E. Lazerwith, Burlingame, CA (US); Michel Leeman, Fairfield, NJ (US); Zhihui Peng, Niantic, CT (US); Kate Schrier, Redwood City, CA (US); Jonathan Trinidad, Fremont, CA (US); Jochem Van Herpt, Fairfield, NJ (US); Andrew W. Waltman, Kalamazoo, MI (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 16/686,912

(22) Filed: Nov. 18, 2019

(65) Prior Publication Data

US 2020/0223866 A1 Jul. 16, 2020

Related U.S. Application Data

(63) Continuation of application No. 15/639,833, filed on Jun. 30, 2017, now Pat. No. 10,519,168, which is a continuation of application No. 14/740,954, filed on Jun. 16, 2015, now abandoned.

(60) Provisional application No. 62/015,081, filed on Jun. 20, 2014.

(51) Int. Cl.

| C07D 498/14 | (2006.01) |
| C07D 498/22 | (2006.01) |
| C07D 319/06 | (2006.01) |
| C07D 309/40 | (2006.01) |
| C07C 237/20 | (2006.01) |
| C07D 213/82 | (2006.01) |
| C07C 235/80 | (2006.01) |
| C07C 231/02 | (2006.01) |
| C07C 231/12 | (2006.01) |

(52) U.S. Cl.
CPC .......... *C07D 498/14* (2013.01); *C07C 231/02* (2013.01); *C07C 231/12* (2013.01); *C07C 235/80* (2013.01); *C07C 237/20* (2013.01); *C07D 213/82* (2013.01); *C07D 309/40* (2013.01); *C07D 319/06* (2013.01); *C07D 498/22* (2013.01)

(58) Field of Classification Search
CPC ... C07D 471/18; C07D 471/22; C07D 498/18
USPC .............................. 544/346, 95; 549/375, 379
See application file for complete search history.

(56) References Cited

U.S. PATENT DOCUMENTS

| 4,188,403 A | 2/1980 | Orth et al. |
| 5,032,583 A | 7/1991 | Evans |
| 5,631,383 A | 5/1997 | Largeau et al. |
| 5,814,639 A | 9/1998 | Liotta et al. |
| 5,889,178 A | 3/1999 | Gregson et al. |
| 5,914,331 A | 6/1999 | Liotta et al. |
| 5,922,695 A | 7/1999 | Arimilli et al. |
| 5,925,624 A | 7/1999 | Gregson et al. |
| 5,935,946 A | 8/1999 | Munger, Jr. et al. |
| 5,977,089 A | 11/1999 | Arimilli et al. |
| 6,043,230 A | 3/2000 | Arimilli et al. |
| 6,380,218 B1 | 4/2002 | Marfat et al. |
| 6,479,490 B2 | 11/2002 | Gong et al. |
| 6,620,841 B1 | 9/2003 | Fujishita et al. |
| 6,642,245 B1 | 11/2003 | Liotta et al. |
| 6,703,396 B1 | 3/2004 | Liotta et al. |
| 7,176,220 B2 | 2/2007 | Satoh et al. |
| 7,211,572 B2 | 5/2007 | Miyazaki et al. |
| 7,250,518 B2 | 7/2007 | Magee et al. |
| 7,390,803 B2 | 6/2008 | Butora et al. |

(Continued)

FOREIGN PATENT DOCUMENTS

| DE | 2244012 A1 | 3/1973 |
| DE | 2552871 A1 | 7/1976 |

(Continued)

OTHER PUBLICATIONS

Agrawal, et al. (2012) "Probing Chelation Motifs in HIV Integrase Inhibitors" Proc. Natl. Acad. Sci. U.S.A. 109(7): 2251-2256.

(Continued)

*Primary Examiner* — Venkataraman Balasubramanian

(57) ABSTRACT

Methods of making compounds of Formula I are disclosed:

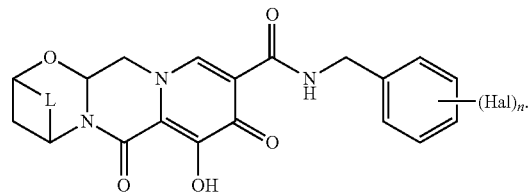

Formula I

39 Claims, No Drawings

(56) References Cited

U.S. PATENT DOCUMENTS

| | | |
|---|---|---|
| 7,419,969 B2 | 9/2008 | Naidu et al. |
| 7,550,463 B2 | 6/2009 | Yoshida |
| 7,598,288 B2 | 10/2009 | Hellberg et al. |
| 7,635,704 B2 | 12/2009 | Satoh et al. |
| 7,858,788 B2 | 12/2010 | Yoshida et al. |
| 7,888,376 B2 | 2/2011 | Salvati et al. |
| 7,968,587 B2 | 6/2011 | Gavardinas et al. |
| 8,129,385 B2 | 3/2012 | Johns et al. |
| 8,148,374 B2 | 4/2012 | Desai et al. |
| 8,188,271 B2 | 5/2012 | Yoshida et al. |
| 8,410,103 B2 | 4/2013 | Johns et al. |
| 8,592,397 B2 | 11/2013 | Dahl et al. |
| 8,629,274 B2 | 1/2014 | Hartman et al. |
| 8,633,219 B2 | 1/2014 | Matsuzaki et al. |
| 8,716,264 B2 | 5/2014 | Dahl et al. |
| 8,778,943 B2 | 7/2014 | Johns et al. |
| 8,981,103 B2 | 3/2015 | Ando et al. |
| 8,987,441 B2 | 3/2015 | Takahashi et al. |
| 9,051,337 B2 | 6/2015 | Johns et al. |
| 9,216,996 B2 * | 12/2015 | Jin .................. A61P 31/12 |
| 9,663,528 B2 | 5/2017 | Desai et al. |
| 9,682,084 B2 | 6/2017 | Carra et al. |
| 9,708,342 B2 | 7/2017 | Carra et al. |
| 9,732,092 B2 | 8/2017 | Jin et al. |
| 9,751,857 B2 | 9/2017 | Hartman et al. |
| 9,866,271 B2 | 1/2018 | Park et al. |
| 10,035,809 B2 | 7/2018 | Bacon et al. |
| 10,098,886 B2 | 10/2018 | Carra et al. |
| 10,385,067 B2 | 8/2019 | Carra et al. |
| 10,519,168 B2 * | 12/2019 | Enquist, Jr. .......... C07D 498/22 |
| 2005/0054645 A1 | 3/2005 | Miyazaki et al. |
| 2005/0137224 A1 | 6/2005 | Shima et al. |
| 2006/0086401 A1 | 4/2006 | Sato |
| 2007/0072831 A1 | 3/2007 | Cai et al. |
| 2007/0117848 A1 | 5/2007 | Puerta et al. |
| 2008/0020010 A1 | 1/2008 | Nair et al. |
| 2008/0139579 A1 | 6/2008 | Morrissette et al. |
| 2008/0161271 A1 | 7/2008 | Yoshida et al. |
| 2008/0280945 A1 | 11/2008 | Lohani et al. |
| 2009/0036684 A1 | 2/2009 | Matsuda et al. |
| 2009/0143356 A1 | 6/2009 | Yoshida et al. |
| 2009/0253677 A1 | 10/2009 | Beaulieu et al. |
| 2009/0318421 A1 | 12/2009 | Johns et al. |
| 2009/0318702 A1 | 12/2009 | Matsuda et al. |
| 2010/0068695 A1 | 3/2010 | Kiyama et al. |
| 2012/0022251 A1 | 1/2012 | Sumino et al. |
| 2012/0022255 A1 | 1/2012 | Fujishita et al. |
| 2012/0108564 A1 | 5/2012 | Miyazaki et al. |
| 2012/0115875 A1 | 5/2012 | Johns et al. |
| 2012/0184734 A1 | 7/2012 | Akiyama et al. |
| 2012/0208998 A1 | 8/2012 | Yoshida et al. |
| 2012/0232117 A1 | 9/2012 | Bae et al. |
| 2013/0006485 A1 | 1/2013 | Kwasniewski |
| 2013/0172559 A1 | 7/2013 | Johns et al. |
| 2014/0011995 A1 | 1/2014 | Sumino et al. |
| 2014/0094605 A1 | 4/2014 | Yoshida et al. |
| 2014/0221355 A1 | 8/2014 | Lazerwith et al. |
| 2014/0221356 A1 | 8/2014 | Jin et al. |
| 2014/0221378 A1 | 8/2014 | Myazaki et al. |
| 2014/0243521 A1 | 8/2014 | Yoshida et al. |
| 2014/0256937 A1 | 9/2014 | Akiyama |
| 2015/0232479 A1 | 8/2015 | Johns et al. |
| 2017/0333438 A1 | 11/2017 | Carra et al. |
| 2018/0065986 A1 | 3/2018 | Carra et al. |
| 2018/0153887 A1 | 6/2018 | Ji et al. |
| 2018/0155364 A1 | 6/2018 | Chava et al. |

FOREIGN PATENT DOCUMENTS

| | | | |
|---|---|---|---|
| DE | 2658401 A1 | | 7/1978 |
| EP | 0154199 A2 | | 9/1985 |
| EP | 0378067 A2 | | 7/1990 |
| EP | 0456073 A2 | | 11/1991 |
| EP | 1544199 A1 | | 6/2005 |
| EP | 1874117 A1 | | 1/2008 |
| EP | 2412709 A1 | | 2/2012 |
| EP | 1422218 B1 | | 3/2012 |
| EP | 2465580 A1 | | 6/2012 |
| EP | 2527007 A1 | | 11/2012 |
| EP | 2602260 A1 | | 6/2013 |
| GB | 2345058 A | | 6/2000 |
| IN | 2014/0247/CHE/2014 | | 1/2015 |
| IN | 2015/11110/1686-MUM-2014 | | 5/2015 |
| WO | WO-1994/017090 A1 | | 8/1994 |
| WO | WO-1998/011103 A1 | | 3/1998 |
| WO | WO-1999/005142 A1 | | 2/1999 |
| WO | WO-1999/025345 A1 | | 5/1999 |
| WO | WO-2000/027823 A1 | | 5/2000 |
| WO | WO-2003/030897 A1 | | 4/2003 |
| WO | WO-2003/035077 A1 | | 5/2003 |
| WO | WO-2004/004657 A2 | | 1/2004 |
| WO | WO-2004/024078 A2 | | 3/2004 |
| WO | WO-2005/016927 A1 | | 2/2005 |
| WO | WO-2005/042533 A1 | | 5/2005 |
| WO | WO-2005/074513 A2 | | 8/2005 |
| WO | WO-2005/110399 A2 | | 11/2005 |
| WO | WO-2005/110414 A2 | | 11/2005 |
| WO | WO-2005/112930 A1 | | 12/2005 |
| WO | WO-2005/113508 A1 | | 12/2005 |
| WO | WO-2005/113509 A1 | | 12/2005 |
| WO | WO-2006/028523 A2 | | 3/2006 |
| WO | WO-2006/030807 A1 | | 3/2006 |
| WO | WO-2006/066414 A1 | | 6/2006 |
| WO | WO-2006/088173 A1 | | 8/2006 |
| WO | WO-2006/116764 A1 | | 11/2006 |
| WO | WO-2007/014352 A2 | | 2/2007 |
| WO | WO-2007/049675 A1 | | 5/2007 |
| WO | WO-2007/079260 A1 | | 7/2007 |
| WO | WO-2007/089030 A1 | | 8/2007 |
| WO | WO-2007/092681 A2 | | 8/2007 |
| WO | WO-2007/099385 A1 | | 9/2007 |
| WO | WO-2007/102499 A1 | | 9/2007 |
| WO | WO-2007/102512 A1 | | 9/2007 |
| WO | WO-2008/002959 A2 | | 1/2008 |
| WO | WO-2008/033836 A2 | | 3/2008 |
| WO | WO-2008/048538 A1 | | 4/2008 |
| WO | WO-2009/006199 A1 | | 1/2009 |
| WO | WO-2009/006203 A1 | | 1/2009 |
| WO | WO-2009/018320 A1 | | 2/2009 |
| WO | WO-2009/018350 A1 | | 2/2009 |
| WO | WO-2009/036161 A1 | | 3/2009 |
| WO | WO-2009/103950 A1 | | 8/2009 |
| WO | WO-2010/011812 A1 | | 1/2010 |
| WO | WO-2010/011813 A1 | | 1/2010 |
| WO | WO-2010/011814 A1 | | 1/2010 |
| WO | WO-2010/011815 A1 | | 1/2010 |
| WO | WO-2010/011816 A1 | | 1/2010 |
| WO | WO-2010/011818 A1 | | 1/2010 |
| WO | WO-2010/011819 A1 | | 1/2010 |
| WO | WO-2010/068253 A1 | | 6/2010 |
| WO | WO-2010/068262 A1 | | 6/2010 |
| WO | WO-2010/110231 A1 | | 9/2010 |
| WO | WO-2010/110409 A1 | | 9/2010 |
| WO | WO-2010/147068 A1 | | 12/2010 |
| WO | WO-2011/094150 A1 | | 8/2011 |
| WO | WO-2011/105590 A1 | | 9/2011 |
| WO | WO-2011/119566 A1 | | 9/2011 |
| WO | WO-2012/009009 A2 | | 1/2012 |
| WO | WO-2012/018065 A1 | | 2/2012 |
| WO | WO-2012/039414 A1 | | 3/2012 |
| WO | WO-2012/106534 A2 | | 8/2012 |
| WO | WO-2012/151361 A1 | | 11/2012 |
| WO | WO-2012/151567 A1 | | 11/2012 |
| WO | WO-2013/038407 A1 | | 3/2013 |
| WO | WO-2013/054862 A1 | | 4/2013 |
| WO | WO-2013/087581 A1 | | 6/2013 |
| WO | WO-2014/008636 A1 | | 1/2014 |
| WO | WO-2014/011769 A1 | | 1/2014 |
| WO | WO-2014/014933 A1 | | 1/2014 |
| WO | WO-2014/018449 A1 | | 1/2014 |
| WO | WO-2014/022707 A1 | | 2/2014 |
| WO | WO-2014/074675 A1 | | 5/2014 |

(56) References Cited

FOREIGN PATENT DOCUMENTS

| | | |
|---|---|---|
| WO | WO-2014/093941 A1 | 6/2014 |
| WO | WO-2014/099586 A1 | 6/2014 |
| WO | WO-2014/100077 A1 | 6/2014 |
| WO | WO-2014100323 A1 | 6/2014 |
| WO | WO-2014/104279 A1 | 7/2014 |
| WO | WO-2014/200880 A1 | 12/2014 |
| WO | WO-2015/039348 A1 | 3/2015 |
| WO | WO-2015/048363 A1 | 4/2015 |
| WO | WO-2015/089847 A1 | 6/2015 |
| WO | WO-2015/095258 A1 | 6/2015 |
| WO | WO-2015/110897 A2 | 7/2015 |

OTHER PUBLICATIONS

AIDS treatment Guidelines (2013)—"AIDS info Guidelines for the Use of Antiretroviral Agents in HIV-1-Infected Adults and Adolescents," [downloaded from http://aidsinfo.nih.gov/guidelines on Mar. 15, 2013], 267 pages.
Akiyama, et al. (2013) "Discovery of Novel HIV Integrase Inhibitors Part 2. Selection and Evaluation of an Azabicylic Carbamoyl Pyridone as apre-Clinical Candidate" Poster, American Chemical Society National Meeting and Exposition; Apr. 7-11; New Orleans, LA.
Andrews, C. et al. (2014) "Long-Acting Integrase Inhibitor Protects Macaques from Intrarectal Simian/Human Immunodeficiency Virus" Science 343:1151-1154.
Arthur J. Moss et al. "Ranolazine Shortens Repolarization in Patients with Sustained Inward; Sodium Current Due to Type-3 Long-QT Syndrome", Journal of Cardiovascular Electrophysiology 19(12): 1289-1293.
Atsushi M. et al. (2001) "Regioselective Oxygenations of S-Trans Dienes, Silyl Dienol Ethers (SDEs), by Triphenyl Phosphite Ozonide (TPPO) and It's Mechanistic Study" The Journal of Organic Chemistry 66(10): 3548-3553.
Barrow J. C. et al (2000) "Preparation and Evaluation of 1, 3-diaminocyclopentane-linked dihydropyrimidinone derivatives as selective alphala-receptor antagonists" Bioorganic & Medicinal Chemistry Letters, Pergamon, Amsterdam, NL 10(17): 1917-1920.
Barrow, et al., (2000) "Preparation and Evaluation of 1,3-Diaminocyclopentane-Linked Dihydropyrimidinone Derivatives as Selective 1a-Receptor Antagonists" Bioorganic & Medicinal Chemistry Letters, 10(17): 1917-1920.
Bisel, P. et al. (1998) "Diastereoselective .alpha.-iminoamine rearrangement: asymmetric synthesis of (R)-(−)- and (S)-(−)-2-benzyl-2-hydroxycyclohexanone" Tetrahedron: Asymmetry 9:4027-4034.
Brehm et. al. (1954) "The Relative Acidifying Influence of Oxygen and Sulfur Atoms on α—Hydrogen Atoms" 76:5389-5391.
Brinson, C. et al. (2013) "Dolutegravir Treatment Response and Safety by Key Subgroups in Treatment Naive HIV Infected Individuals" Poster, 20th Conference on Retroviruses and Opportunistic Infections; 2013, Mar. 3-6; Atlanta, GA.
Brocklehurst, C.E. et al. (2011) "Diastereoisomeric Salt Formation and Enzyme-Catalyzed Kinetic Resolution as Complementary Methods for the Chiral Separation of cis-/ trans-Enantiomers of 3-Aminocyclohexanol" Organic Process Research and Development 15(1):294-300.
Cahn, P. et al. (2013) "Dolutegravir (DTG) is Superior to Raltegravir (RAL) in ART-Experienced, Integrase-Naive Subjects: Week 48 Results From Sailing (ING111762)" Presentation, 7.sup.th IAS Conference on HIV Pathogenesis, Treatment and Prevention;Jun. 30-Jul. 3; Kuala Lumpur, Malaysia.
Canducci, F. et al. (2013) "In vitro phenotypes to elvitegravir and dolutegravir in primary macrophages and lymphocytes of clonal recombinant viral variants selected in patients failing raltegravir", J Antimicrob Chemother., 68:2525-32.
Castagna, A. et al. (2014) "Dolutegravir in Antiretroviral-Experienced Patients With Raltegravir- and/or Elvitegravir-Resistant HIV-1: 24-Week Results of the Phase III VIKING-3 Study" Infectious Diseases Society of America Journal of InfectiousDiseases 210:354-62.
Castellino, S., et al., (2013), "Metabolism, Excretion, and Mass Balance of the HIV-1 Integrase Inhibitor Dolutegravir in Humans", Antimicrobial Agents and Chemother., 57:3536-46.
Chava, et al., Indian Patent Application No. 0247/CHE/2014 (Publication Date Aug. 14, 2015), "Novel Process for the Preparation of Dolutegravir and Pharmaceutically Acceptable Salts Thereof" Laurus Labs Private Limited, pp. 1-83.
Chen, D. et al. (2003) "New C19-diterpenoid alkaloids from the roots of Aconitum transsecutum" Abstract, Huaxue Xuebao 61(6):901-906.
Chen, S. et al. (2014) "Evaluation of the effect of UGT1A1 polymorphisms on dolutegravir pharmacokinetics" Pharmacogenomics 15(1):9-16.
Chorell, E et al. (2012) "Design and Synthesis of Fluorescent Pilicides and Curlicides: Bioactive Tools to Study Bacterial Virulence Mechanisms" Chemistry—A European Journal, 18(15): 4522-4532.
Clotet, G. et al. (2014) "Once-daily dolutegravir versus darunavir plus ritonavir in antiretroviral-naive adults with HIV-1 infection (FLAMINGO) 48 week results from the randomised open-label phase 3b study", Lancet, 383:2222-31.
Cohen, J. et al. (2014) "A Bid to Thwart HIV With Shot of Long-Lasting Drug" Science 343:1067.
Cottrell, M. et al. (2013) "Clinical Pharmacokinetic, Pharmacodynamic and Drug-Interaction Profile of the Integrase Inhibitor Dolutegravir" Clin Pharmacokinet 52:981-994.
Culp, A. et al. (2014) "Metabolism, Excretion, and Mass Balance of the HIV Integrase Inhibitor, Cabotegravir (GSK1265744) in Humans" Presentation, 54th Intersience Conference on Antimicrobial Agents and Chemotherapy; Sep. 5-9; Washington, DC., 1-7.
Curtis, L. et al. (2013) "Once-Daily Dolutegravir (DTG; GSK1349572) Has a Renal Safety Profile Comparable to Raltegravir (RAL) and Efavirenz in Antiretroviral (ART)-Naive Adults: 48 Week Results From SPRING-2 (ING113086) and SINGLE (ING114467)" Poster No. CUPE 282, 7.sup.th IAS Conference on HIV Pathogenesis, Treatment and Prevention; Jun. 30-Jul. 3; Kuala Lumpur, Malaysia.
Dauvergne J. et al. (2004) "Synthesis of 4-azacyclopent-2-enones and 5,5-dialkyl-4-azacyclopent-2-enones" Tetrahedron, Elsevier Science Publishers 60(11): 2559-2567.
Deanda, F. et al. (2013) "Dolutegravir Interactions with HIV-1 Integrase-DNA: Structural Rationale for Drug Resistance and Dissociation Kinetics" PLoS One 8(10): e77448 1-12.
Disclosed Anonymously. (2014) "Preparation of Methyl 3-(benzyloxy)-5-992,4-difluorobenzyl)carbamoyl)-1-(2,2-dimethoxy ethyl)-4-oxo1,4-dihydropyridine-2-carboxylate" An IP.com Prior Art Database Technical Disclosure, the whole document.
Disclosed Anonymously. (2014) "Process for the Preparation of 4H-PYRAN-4-ONE Derivatives" An IP.com Prior Art Database Technical Disclosure, //priorat.ip.com/IPCOM/000235923.
Enright, B. et al. (2010) "Assessment of Hydroxypropyl Methylcellulose, Propylene Glycol, Polysorbate 80, and Hydroxypropyl-beta-Cyclodextrin for Use in Developmental and Reproductive Toxicology Studies" Birth Defects Research (Part B)89:504-516.
European Search Report dated Mar. 31, 2015 for EP application No. 13815937.1.
Extended European Search Report dated Jul. 19, 2019 for EP App. No. 19167626.1.
Extended Search Report dated Jun. 12, 2019 for European Appl. No. 19152851.2.
Farzaneh-Far Ramin et al. (2013) "The Anto-Ischemic Effect of Ranolazine Closely Parallels its QTC-Shortening Effect in Patients with Long-QT Syndrome 3", *Journal of the American College of Cardiology* 61(10):1176-6.
FDA DTG Pharmacology Review—Center for Drug Evaluation and Research; DTG PharmTox Review 2013, 103 pages.
FDA_DDI (2012) Guidance for Industry—Drug Interaction Studies—Study Design, Data Analysis, Implications for Dosing, and Labeling Recommendations, 79 pages.
Feinberg, J. et al. (2013) "Once-Daily Dolutegravir (DTG) is Superior to Darunavir/Ritonavir (DRV)/f) in Antiretroviral-Naive

(56) References Cited

OTHER PUBLICATIONS

Adults: 48 Week Results from FLAMINGO (ING114915)" Presentation, 53.sup.rd ICAAC Interscience Conference on AntimicrobialAgents and Chemotherapy; Sep. 10-13; Denver CO.
Forro, et al., (2008) "Enzymatic Method for the Synthesis of Blockbuster Drug Intermediates—Synthesis of Five-Membered Cyclic ?-Amino Acid and ?-Lactam Enantiomers" European Journal of Organic Chemistry , 31: 5263-5268.
Gad, S. et al. (2006) "Nonclinical Vehicle Use in Studies by Multiple Routes in Multiple Species" International Journal of Toxicology 25:499-521.
Gao, Y. et al. (2007) "Attenuating Pregnane X Receptor (PXR Activiatin: A Molecular Modeling Approach" Xenobiotica 37(2):124-138.
Gein, V. L. et al. (1992) "Synthesis of 4-Substituted 1-Methyl-5-Aryl- and 1,5-Diaryltetrahydropyrrole-2,3-Diones and their Antiviral Action" Translated from Khimik-farmatsevticheskii Zhumal 25(12):37-40.
Goldys et al. (2014) "Creation through Immobilization: A New Family of High Performance Heterogeneous Bifunctional Iminophosphorane (BIMP) Superbase Organocatalyts" Organic Letters, 16(24): 6294-6297; see the preparation of the compound 11f accordgin to pp. S15-S16 of the Suppplementary Information.
Gould, S. et al. (2005) "2-Hydroxypropy.beta.-cyclodextrin (HP-.beta.-CD): A toxicology review" Food and Chemical Toxicology 43:1451-1459.
Gouverneur, V. et al. (1998) "New Acylnitroso Compounds for the Asymmetric Oxyamination of Dienes" Tetrahedron 54:10537-10554.
Grobler, J., et al. (2002) "Diketo Acid Inhibitor Mechanism and HIV-1 Integrase: Implications for Metal Binding in the Active Site of Phosphotransferase Enzymes" Proc. Natl. Acad. Sci. U.S.A.; 99(10):6661-6666.
Gutierrez, M., "Drug safety profile of integrase strand transfer inhibitors," Expert Opin. Drug Saf. (2014) 13(4):431-445.
Hall (1960) "Synthesis and Polymerization of Aton-bridged Bicyclic Lactams" Journal of Organic Chemistry, 82: 1209-1215.
Hare, S. et al. (2011) "Structural and Functional Analyses of the Second-Generation Integrase Strand Transfer Inhibitor Dolutegravir (S/GSK1349572)" Molecular Pharmacology 80(4):565-572.
Hightower, K., "Dolutegravir (S/GKS1349572) Exhibits Siginifcantly Slower Dissociation than Raltegrvir and Elvitegravir from Wild-Type and Integrase Inhibitor-Resistant HIV-1 Integrase-DNA Complexes," Antimicrobial Agents and Chemotherapy 55(10):4552-4559 (2011).
Huang, W. et al. (2014) "Impact of Raltegravir/Elvitegravir Selected Mutationson Dolutegravir Cross-Resistance" Poster 595, 21st Conference on Retroviruses and Opportunistic Infection; Mar. 3-6; Boston, MA.
Huang, W. et al. (2014) "Impact of Raltegravir/Elvitegravir Selected Mutationson Dolutegravir Cross-Resistance" Poster 595; 21.sup.st Conference on Retroviruses and Opportunistic Infection; Mar. 3-6; Boston, MA.
Hurt et al., (2014), "Resistance to HIV Integrase Strand Transfer Inhibitors Among Clinical Specimens in the United States, 2009-2012", Clin Infect Dis., 58:423-31.
Hurt, C. et al. (2013) "Characterization of Resistance to Integrase Strand Transfer Inhibitors among Clinical Specimens in the United States, 2009-2012" Poster 591, 20th Conference on Retroviruses and Opportunistic Infections; Mar. 3-6; Atlanta, GA.
Hurtley, (1901) "The chlorodibromo- and dichlorobromobenzens" J. Chem. Soc., Trans., 79: 1293-1305.
International Preliminary Report on Patentability dated Jun. 23, 2015 for PCT/US2013/076367.
Intl Search Report—Written Opinion dated Sep. 18, 2006 for PCT/US2006/016604.
Intl. Search Report—Written Opinion dated Feb. 9, 2016 for PCT/US2015/026017.
Intl. Search Report—Written Opinon dated Feb. 27, 2015 for PCT/US2014/071310.
Intl. Search Report dated Mar. 12, 2014 for PCT/US2013/076367.
Jagt et al., (1974) "Diels-Alder Cycloadditions of Sulfonyl Cyanides with Cyclopentadiene. Synthesis of 2-Azabicyclo [2.2.1]hepta-2,5-dienes" J. Org. Chem., 39(4) 564-566.
Johns, B. et al., (2013), "HIV Integrase Inhibitors", Successful Strategies for Discovery of Antiviral Drugs, 32(6):149-88.
Johns, B., et al., "Carbamoyl Pyridone HIV-1 Integrase Inhibitors 3. A Diastereomeric Approach to Chiral Nonracemic Tricyclic Ring Systems and the Discovery of Dolutegravir (S/GSK1349572) and (S/GSK1265744)," J. Med. Chem. (2013) 56:5901-5916 (16 pages).
Kawasuji, T., et al. (2007) "3-Hydroxy-1,5-dihydro-pyrrol-2-one Derivatives as Advanced Inhibitors of HIV Integrase" Bioorganic & Medicinal Chemistry; 15:5487-5492.
Kawasuji, T., et al. (2012) "Carbamoyl Pyridone HIV-1 Integrase Inhibitors. 1. Molecular Design and Establishment of an Advanced Two-Metal Binding Pharmacophore" J. Med. Chem.; 55(20):8735-8744.
Kliewer, S. et al. (2002) "The Nuclear Pregnane X Receptor: A Key Regulator of Xenobiotic Metabolism" Endocrine Reviews 23(5):687-702.
Kobayashi, M. et al. (2011) "In Vitro Antiretroviral Properties of S/GSK1349572, a Next-Generation HIV Integrase Inhibitor" Antimicrob Agents and Chemother 55(2):813-21.
Krow, G. et al. (2008) "Selectfluor as a Nucleofuge in the Reactions of Azabicyclo[n. 2.1]alkane.beta.-Halocarbamic Acid Esters (n=2,3)" J. Org. Chem. 73:2122-2129.
Kudoh, et al., (2005) "Synthesis of Stable and Cell-type Selective Analogues of Cyclic ADP-Ribose, a Ca2+-Mobilizing Second Messenger. Structure-Activity Relationship of the N1-Ribose Moiety" Journal of the American Chemical Society, 127(24): 8846-8855.
Lepist, E. et al. (2011) "Effect of Cobicistat and Ritonavir on Proximal Renal Tubular Cell Uptake and Efflux Tansporters" Poster A1-1724; 51.sup.st Interscience Conference on Antimicrobial Agents and Chemotherapy; Sep. 17-20; Chicago, IL.
Letendre, S. et al. (2013) "Distribution and Antiviral Activity in Cerebrospinal Fluid (CSF) of the Integrase Inhibitor, Dolutegravir (DTG): ING116070 Week 16 Results" Poster 178LB; 20th Conference on Retroviruses and Opportunistic Infections; Mar. 3-6; Atlanta, GA.
Llyod, J. et al. (2009) "Dihydropyrazolopyrimidines containing benzimidazoles as KV1.5 potassium channel antagonistics" Bioorganic & Medicinal Chemistry Letters 19(18):5469-5473.
Lou, Y. et al. (2013) "Meta-Analysis of Safety Data From 8 Clinical Studies With GSK1265744, an HIV Integrase Inhibitor, Dosed Orally or as Injection of Long-Acting Parenteral Nanosuspension (LAP)" Poster H-672; 53rd Interscience Conference onAntimicrobial Agents and Chemotherapy; Sep. 10-13; Denver, CO.
Maggi, P. (2014) "The Problem of Renal Function Monitoring in Patients Treated With the Novel Antiretroviral Drugs", HIV Clinical Trials, HIV Clin Trials;15(3):87-91.
Malet, I., et al., (2014) "New raltegravir resistance pathways induce broad cross-resistance to all currently used integrase inhibitors", J Antimicrob Chemother, 69: 2118-2122.
Margolis et al. (2014) "744 and Rilpivirine As Two Drug Oral Maintenance Therapy: LAI116482 (LATTE) Week 48 Results" Presentation; 21st Conference on Retroviruses and Opportunistic Infections; Mar. 3-6; Boston, MA.
Menendez-Arias, L., Alvarez, M., "Antiretroviral therapy and drug resistance in human immunodeficiency virus type 2 infection," Antiviral Res. (2013), http://dx.doi.org/10.1016/j.antiviral.2013.12.001.
Metifiot, M. et al. (2013) "HIV Integrase Inhibitors: 20-Year Landmark and Challenges" Advances in Pharmacology 67:75-105.
Min' S. S et al.(2010) "Pharmacokinetics and Safety of S/GSK1349572, a Next-Generation HIV Integrase Inhibitor, in Healthy Volunteers" Antimicrob Agents and Chemother 54(1):254-258.
Min' S. et al.(2011) "Antiviral activity, safety, and pharmacokinetics/pharmacodynamics of dolutegravir as 10-day monotherapy in HIV-1-infected adults" AIDS 25(14):1737-1745.
Mulvihill M.J. et al. (1998) "Enzymatic resolution of aminocyclopentenols as precursors to D- and L-carbocyclic nucleosides" The Journal of Organic Chemistry, American Chemistry Society, US, 63(10): 3357-3363.

(56) References Cited

OTHER PUBLICATIONS

Nair, V. et al (2014) "Pharmacokinetics and Dose-range Finding Toxicity of a Novel anti-HIV Active Integrase Inhibitor" Supplementary Materials.
Nichols, G. et al (2013) "Phase 3 Assessment of Dolutegravir (DTG) 50 mg Twice Daily (BID) in HIV-1-Infected Subjects With Raltegravir (RAL) and/or Elvitegravir (EVG) Resistance in VIKING-3: Week 24 Results of All 183 Subjects Enrolled" PosterTULBPE19; 7.sup.th IAS Conference on HIV Pathogenesis, Treatment and Prevention Jun. 30-Jul. 3; Kuala Lumpur, Malaysia.
Nichols, G. et al. (2012) "Antiviral Activity of Dolutegravir in Subjects With Failure on an Integrase Inhibitor-Based Regimen: Week 24 Phase 3 Results From VIKING-3" Presentation O232; 11th International Congress on Drug Therapy in HIV Infection;Nov. 11-15; Glasgow, UK.
Nishioka, K. et al. (1992) "C-Labeling of a Tetrahydroacridine, a Novel CNS-Selective Cholinesterase Inhibitor" Journal of Labelled Compounds and Radiopharmaceuticals XXXI(7):553-560.
Office Action dated Mar. 30, 2015 for Pakistan Appl. No. 908/2013.
Office Action dated Dec. 6, 2018 for Israeli App. No. 260675, 4pgs.
Office Action dated Jun. 25, 2019 for Israeli App. No. 249161.
Office Action dated Jul. 3, 2019 for Salvadorian App. No. 5002-2015.
Office Action dated Aug. 16, 2019 for Chilean App. No. 201701191.
Opposition dated Jun. 20, 2017 for Colombian Appl. No. 15-265.717.
Opposition Decision in European patent application No. 02749384.0, dated Mar. 12, 2015.
Pace, P., et al. (2007) "Dihydroxypyrimidine-4-carboxamides as Novel Potent and Selective HIV Integrase Inhibitors" J. Med. Chem; 50:2225-2239.
Park, B. et al. (2001) "Metabolism of Fluorine-Containing Drugs" Annu. Rev. Pharmacol. Toxicol. 41:443-70.
Patel, P. et al. (2014) "Relative Bioavailability of a Paediatric Granule Formulation of the HIV Integrase Inhibitor, Dolutegravir, in Healthy Adult Subjects" Antiviral Therapy.
Patel, P., et al., "Pharmacokinetics of the HIV integrase inhibitor S/GSK1349572 co-administered with acid-reducing agents and multivitamins in healthy volunteers," J Antimicrob Chemother (2011); 66: 1567-1572.
Peng, C. et al. (2002) "Norditerpenoid alkaloids from the roots of Aconitum hemsleyanum Pritz. var. *pengzhouense*" Abstract, Chinese Chemical Letters 13(3):233-236.
Petrocchi, A., et al. (2007) "From Dihydroxypyrimidine Carboxylic Acids to Carboxamide HIV-1 Integrase Inhibitors: SAR Around the Amide Moiety" Bioorganic & Medicinal Chemistry Letters; 17:350-353.
Plamen A. et al. (2012) "Biomimetic Synthesis, antibacterial activity and structure-activity properties of the pyroglutamate core of oxazolomycin" Organic & Biomolecular Chemistry, 10(17): 3472-3485.
Pozniak, A. et al. (2013) "Dolutegravir (DTG) Versus Raltegravir (RAL) in ART-Experienced, Integrase-Naive Subjects: 24-Week Interim Results from Sailing (ING111762)" Poster 179LB; 20th Conference on Retroviruses and Opportunistic Infections; Mar. 3-6; Atlanta, GA.
PXR Background and data, 2 pages.
Quashie, P. et al. (2013) "Evolution of HIV integrase resistance mutations" Curr Opin Infect Dis 26:43-49.
Raffi et al, "Once-daily dolutegravir versus twice-daily raltegravir in; antiretroviral-naive adults with HIV-1 infection (SPRING-2; study): 96 week results from a randomised, double-blind,; non-inferiority trial," www.thelancet.com/infection vol. 13, pp. 927-935, Published online Nov. 2013.
Raffi, et al., (2013), "Once-daily dolutegravir versus raltegravir in antiretroviral-naive adults with HIV-1 infection: 48 week results from the randomised, double-blind, non-inferiority SPRING-2 study", Lancet, 381:735-43, http://dx.doi.org/10.1016/S0140-6736(12)61853-4.

Raffi, F. et al. (2012) "Once-daily Dolutegravir (DTG; S/GSK1349572) is Non-inferior to Raltegravir (RAL) in Antiretroviral-naive Adults. 48 Week Results from SPRING-2 (ING113086)" Presentation THLBB04; XIX International AIDS Conference; Jul. 22-27;Washington, DC.
Raffi, F. et al. (2013) "Dolutegravir is Non-Inferior to Raltegravir and Shows Durable Response Through 96 Weeks: Results From the SPRING-2 Trial" Poster TULBPE17; 7.sup.th IAS Conference on HIV Pathogenesis, Treatment and Prevention; Jun. 30-Jul. 3; Kuala Lumpur, Malaysia.
Raffi_Poster_DTG clinical data summary IAS Kuala Lumpur Jul. 2013 (Spring 2), 1 page.
Ragan, J. et al. (1995) "Studies of the Alkylation of Chiral, Non-Racemic, Tricyclic Pyrrolidinones," Heterocycles 41:57-70.
Rao, et al., Indian Parent Application No. 1686/MUM/2014 (Publication Date Nov. 27, 2015), "Process for Preparing Polycyclic Carbamoyl Pyridone Derivatives" Cipla Limited, pp. 1-81.
Reese, M. et al. (2013) "In Vitro Investigations into the Roles of Drug Transporters and Metabolizing Enzymes in the Disposition and Drug Interactions of Dolutegravir, a HIV Integrase Inhibitor" Drug Metab Dispos 41:353-361.
Rhodes, M., et al., "Assessing a Theoretical Risk of Dolutegravir-Induced Developmental Immunotoxicity in Juvenile Rats," Toxicological Sciences 130(1), 70-81 (2012).
Saag, M.S., (2006), "Emtricitabine, a new antiretroviral agent with activity against HIV and hepatitis B virus", Clin Infect Dis., 42:126-31.
Schenone et al. (1990) "Reaction of 2-Dimethylaminomethylene-1,3-diones with Dinucleophiles. VIII. Synthesis of Ethyl and Methyl 2,4-disubstituted 5-Pyrimidinecarboxylates" 27(2): 295-305.
Seed, J.W. et al., (2013) Trends in Pharmacological Sciences 34(3):185-193.
Song, I. et al. (2010) "Lack of Interaction Between the HIV Integrase Inhibitor S/GSK1349572 and Tenofovir in Healthy Subjects" JAIDS 55(3):365-367.
Song, I. et al. (2012) "Effect of Food on the Pharmacokinetics of the Integrase Inhibitor Dolutegravir" Antimicrob Agents and Chemother 56(3):1627-1629.
Song, I. et al. (2013) "Dolutegrvir Has No Effect on the Pharmacokinetics of Methadone or Oral Contraceptives With Norgestimate and Ethinyl Estradiol" Poster 535; 20th Conference on Retroviruses and Opportunistic Infections; Mar. 3-6; Atlanta, GA.
Song, I. et al. (2013) "Pharmacokinetics (PK) and Pk.sub.—Pharmacodynamic (PD) Relationship of Dolutegravir (DTG) in Integrase Inhibitor (INI)-Naive Subjects" Poster A-1573; 53rd Interscience Conference on Antimicrobial Agents and Chemotherapy;Sep. 10-13; Denver, CO.
Soriano, V., et al. (2011) "Dolutegravir (GSK/ViiV Integrase) Treatment (with 50mg Once & Twice Daily) of HIV Subjects with Raltegravir Resistance & 3-Class ART Resistance: viral suppression at Week 24 in the VIKING Study" Presentation; EACS; Oct. 12-15; Belgrade, Serbia.
Spreen, W. et al (2013) "First study of repeat dose co-administration of GSK1265744 and TMC278 long-acting parenteral nanosuspensions: pharmacokinetics, safety, and tolerability in healthy adults" Presentation; 7.sup.th IAS Conference on HIVPathogenesis, Treatment and Prevention Jun. 30-Jul. 3; Kuala Lumpur, Malaysia.
Spreen, W. et al. (2012) "Pharmacokinetics, Safety and Tolerability of the HIV Integrase Inhibitor S/GSK1265744 Long Acting Parenteral Nanosuspension Following Single Dose Administration to Healthy Adults" Presentation; 19th International AIDSConference; Jul. 22-27; Washington DC.
Spreen, W. et al. (2013) "Pharmacokinetics, Safety, and Monotherapy Antiviral Activity of GSK1265744, an HIV Integrase Strand Transfer Inhibitor" HIV Clin Trials 14(5):192-203.
Springthorpe et. al (2007) "From ATP to AZD61640: The Discovery of an Orally Active Reversible P2Y(12) Receptor Antagonist for the Prevention of Thrombosis." Biorganic & Medicinal Chemistry Letters, 17(21):6013-6018.
Springthorpe, et al., (2007) "From ATP to AZD6140: the discovery of an orally active reversible P2Y12 receptor antagonist for the prevention of thrombosis" Bioorganic & Medicinal Chemistry Letters 17(21): 6013-6018.

(56) References Cited

OTHER PUBLICATIONS

Steed, (2013), "The role of co-crystals in pharmaceutical design", Trends Pharmacol Sci., 34:185-93.
Stellbrink, H. et al. (2013) "Dolutegravir in antiretroviral-naive adults with HIV-1: 96-week results from a randomized dose-ranging study" AIDS 27:1771-1778.
Summa, V., et al. (2006) "4,5-Dihydroxypyrimidine Carboxamides and N-Alkyl-5-hydroxypyrimidinone Carboxamides are Potent, Selective HIV Integrase Inhibitors with Good Pharmacokinetic Profiles in Preclinical Species" J. Med. Chem; 49:6646-6649.
Summary of Product Characteristics Annex I, Leaflet, 62 pages; EU Triumeq [downloaded Sep. 8, 2014].
Tao Y. et al., (1994), "Stereoselective synthesis of disubstituted 3(2H)—furanones via catalytic intramolecular C—H insertion reactions of [alpha]-diazo-[beta]-keto esters including asymmetric induction" Tetrahedron Letters, 35(39): 7626-7272.
Taoda, Y. et al. (2013) "Discovery of Novel HIV Integrase Inhibitors Part 1. Molecular Design and SAR of Azabicyclic Carbamoyl Pyridone Inhibitors" Poster; 245.sup.th American Chemical Society National Meeting and Exposition; Apr. 7-11; New Orleans,LA.
Tchaparian, Eskouhie, "Drug Transporters: An Overview of Their Role in Drug Interactions; Recommended Strategies to Assess Drug Transporters froma Regulatory and Industry Perspective," FDA Guidance Compliance Regulatory Information Guidances (Feb. 14, 2013), 19 pages.
Thackaberry, E. et al. (2010) "Comprehensive Investigation of Hydroxypropyl Methylcellulose, Propylene Glycol, Polysorbate 80, and Hydroxypropyl-Beta-Cyclodextrin for use in General Toxicology Studies" Toxicological Sciences 117(2):485-492.
Thomson Reuters Drug New, "Coadministration of long-acting GSK-744 and rilpivirine found feasible" [downloaded on the web http://drugnews.thomson-pharma.com/ddn/article.do?id=124544] Jul. 8, 2013 8:33:31 AM on Mon Jul. 8, 2013, 1 page; retrieved byHaolun Jin.
Thomson Reuters Drug News "Results from phase III trials of dolutegravir presented" Fri Jul. 5, 2013, 1 page; retrieved by Haolun Jin.
TIVICAY Product Label (Revised Sep. 2018) GlaxoSmithKline, 44 Pages.
Trinite, B. et al. (2013) "An HIV-1 Replication Pathway Utilizing Reverse Transcription Products That Fail to Integrate" Journal of Virology 87(23):12701-12720.
TRIUMEQ Product Label (Revised Nov. 2017) GlaxoSmithKline, 48 Pages.
Tseng, A. et al. (2014) "Drug Interactions with Integrase Inhibitors" Pharm. D.
Van Lunzen, J. et al. (2012) "Once daily dolutegravir (S/GSK1349572) in combination therapy in antiretroviral-naive adults with HIV: planned interim 48 week results from SPRING-1, a dose-ranging, randomised, phase 2b trial" Lancet Infectious Disease12(2):111-118.
Wai, J., et al. (2007) "Dihydroxypyridopyrazine-1,6-dione HIV-1 Integrase Inhibitors" Bioorganic & Medicinal Chemistry Letters; 17:5595-5599.
Walmsley, S. et al. (2012) "Dolutegravir (DTG; S/GSK1349572) + Abacavir/Lamivudine Once Daily Statistically Superior to Tenofovir/ Emtricitabine/Efavirenz: 48-Week Results—SINGLE (ING114467)" Presentation H-556b; 52nd Interscience Conference onAntimicrobial Agents and Chemotherapy; Sep. 9-12; San Francisco, CA.
Walmsley, S. et al. (2013) "Dolutegravir plus Abacavir-Lamivudine for the Treatment of HIV-1 Infection" N Engl J Med 369(19):1807-1818.
Wang, F. et al. (1999) "Modifications of norditerpenoid alkaloids. I. N-deethylation reactions" Abstract, Chinese Chemical Letters 10(5):375-378.
Wang, F. et al. (2005) "To seek an approach toward the chemical conversion of C19-diterpenoid alkaloids to taxoids" Tetrahedron 61(8):2149-2167.
Wang, H. et al. (2015) "An Efficient and Highly Diastereoselective Synthesis of GSK1265744, a Potent HIV Integrase Inhibitor" Org. Letters 17:564-567.
Wang, Ying-Chuan, et al., "Switch in asymmetric induction sense in cycloadditions using camphor-based nitroso dienop," Tetrahedron: Asymmetry 13 (2002) 691-695.
Weller, S. et al. (2013) "Pharmacokinetics (PK) and Safety of Dolutegravir (DTG) in Subjects With Severe Renal Impairment and Healthy Controls" Poster A-1571, 53rd Interscience Conference on Antimicrobial Agents and Chemotherapy; Sep. 10-13; Denver, CO.
Weller, S., et al., (2013) "Bioequivalence of a Dolutegravir, Abacavir, and Lamivudine Fixed-Dose Combination Tablet and the Effect of Food", Poster A-1572; 53rd Interscience Conference on Antimicrobial Agents and Chemotherapy; Sep. 10-13, 2013; Denver, CO.
Wensing, A. et al. (2014) "Special Contribution. 2014 Update of the Drug Resistance Mutations in HIV-1" IAS-USA Topics in Antiviral Medicine 22(3):642-650.
Wolkowicz, U. et al. (2014) "Structural Basis of Mos1 Transposase Inhibition by the Anti-retroviral Drug Raltegravir" ACS Chem. Biol. 9:743-751.
Wu Y.Q. et al. (1993) "Preparation of the pure diastereomeric forms of S-(5'-deoxy-5'-adenosyl)-1-ammonio-4-methyl sulfonio-2 cyclopentene and their evaluation as irreversible inhibitors of S-adenosylmethionine decarboxylase from *Escherichia coli*" Bioorganic & Medicinal Chemistry, 1(5)349-360.
Wu, B. et al. (2008) "Enantioselective Desymmetrization of meso-Aziridines with TMSN.sub.3 and TMSCN Catalyzed by Discrete Yttrium Complexes" Supporting Information, Angew. Chem. Int. Ed., 64pgs.
Xu et al., (2003) "An efficient and inexpensive catalyst system for the aza-Michael reactions of enones with carbamates" Chemical Communications, 20: 2570-2571.
Yoshifumi et al. (2015) " Dioxanone-Fused Dienes Enable Highly Endo-Selective Intramolecular Diels-Alder Reactions" Organic Letters, 17(11): 2756-2759; 2758: Scheme 7, compounds 10a and 10b.
Zhang, X. et al. (2008) "Rapid analysis of a Chinese herbal prescription by liquid chromatography-time-of-flight tandem mass spectrometry" Abstract, Journal of Chromatography A 1206(2:140-146).
Zhao, X. et al. (2014) "4-Amino-1-hydroxy-2-oxo-1,8-naphthyridine-Containing Compounds Having High Potency against Raltegravir-Resistant Integrase Mutants of HIV-1" J Med Chem 57:5190-5202.

\* cited by examiner

SYNTHESIS OF POLYCYCLIC-CARBAMOYLPYRIDONE COMPOUNDS

CROSS REFERENCE TO RELATED APPLICATIONS

This application is a Continuation of application Ser. No. 15/639,833, filed Jun. 30, 2017, which is a Continuation of application Ser. No. 14/740,954, filed Jun. 16, 2015. Application Ser. No. 14/740,954 claims the benefit of U.S. Provisional Application No. 62/015,081, filed Jun. 20, 2014. The entire contents of these applications are incorporated herein by reference in their entirety.

BACKGROUND

Field

Novel methods of synthesis of polycyclic carbamoylpyridone compounds are disclosed. Intermediates in the synthetic pathway of polycyclic carbamoylpyridone compound are also disclosed.

Description of the Related Art

Human immunodeficiency virus infection and related diseases are a major public health problem worldwide. Human immunodeficiency virus type 1 (HIV-1) encodes three enzymes which are required for viral replication: reverse transcriptase, protease, and integrase. Although drugs targeting reverse transcriptase and protease are in wide use and have shown effectiveness, particularly when employed in combination, toxicity and development of resistant strains have limited their usefulness (Palella, et al. *N. Engl. J Med.* (1998) 338:853-860; Richman, D. D. *Nature* (2001) 410:995-1001). Accordingly, there is a need for new agents that inhibit the replication of HIV and that minimize PXR activation when co-administered with other drugs.

Certain polycyclic carbamoylpyridone compounds have been found to have antiviral activity, as disclosed in PCT/US2013/076367. Accordingly, there is a need for synthetic routes for such compounds.

SUMMARY

The present invention is directed to a novel synthetic process for preparing the polycyclic carbamoylpyridone compounds of Formula I using the synthetic steps described herein. The present invention is also directed to particular individual steps of this process and particular individual intermediates used in this process. One embodiment of the present invention provides a process to prepare a Compound of Formula I:

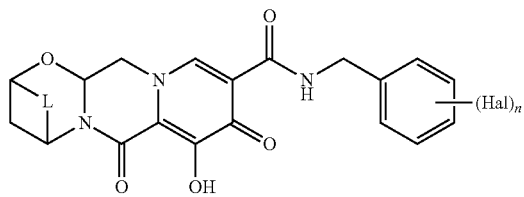

A further embodiment provides a process to prepare a Compound of Formula I

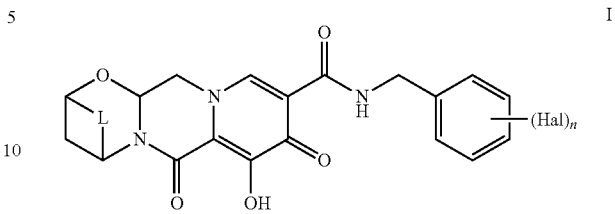

according to the following General Scheme I:

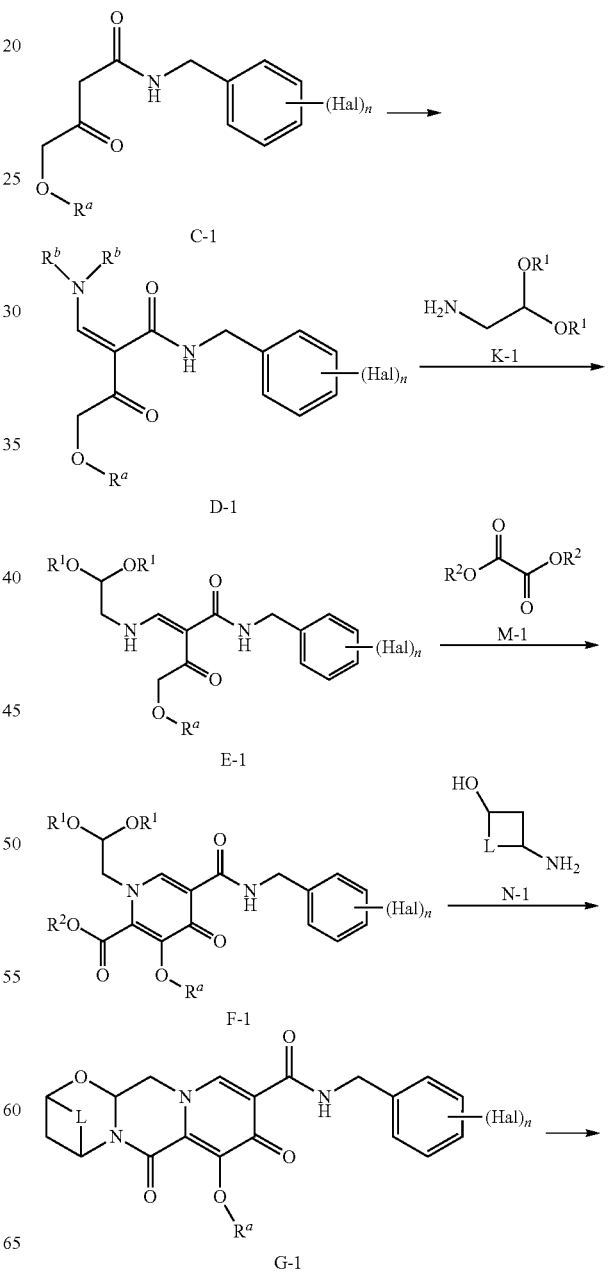

General Scheme I

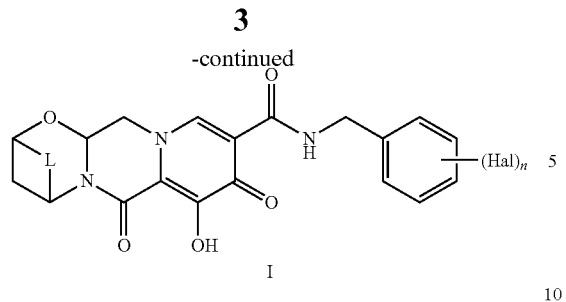

I wherein the process comprises the following steps:
reacting C-1 with an alkylated formamide acetal to yield D-1;
reacting D-1 with K-1 to yield E-1;
reacting E-1 with M-1 in the presence of a base to yield F-1;
reacting F-1 with at least one acid and N-1, or salts or co-crystals thereof, in the presence of a base to yield G-1;
reacting G-1 under conditions suitable to yield a compound of Formula I;
wherein
Hal is halogen, which may be the same or different,
n is 1, 2, or 3,
L is —C($R^c$)$_2$—, —C($R^c$)$_2$C($R^c$)$_2$—, —C($R^c$)$_2$C($R^c$)$_2$C($R^c$)$_2$—, or —C($R^c$)$_2$C($R^c$)$_2$C($R^c$)$_2$C($R^c$)$_2$—,
each $R^c$ is, independently, hydrogen, halo, hydroxyl or $C_1$-$C_4$alkyl,
each $R^a$, $R^1$, and $R^2$ is, independently, ($C_1$-$C_4$)alkyl, ($C_2$-$C_{10}$)aryl, or ($C_2$-$C_{10}$)aryl ($C_1$-$C_4$)alkyl.

In some embodiments, each $R^b$ is independently ($C_1$-$C_4$) alkyl.

In some embodiments, each $R^a$, $R^1$, and $R^2$ is, independently, ($C_1$-$C_4$)alkyl, ($C_6$-$C_{10}$)aryl, or ($C_6$-$C_{10}$)aryl ($C_1$-$C_4$) alkyl.

Another embodiment provides a process to prepare a compound of Formula I

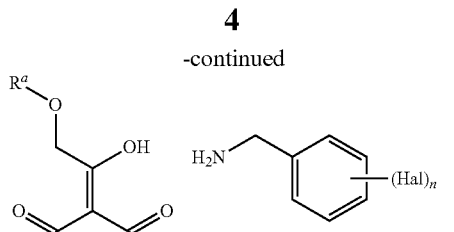

I according to the following General Scheme II:

General Scheme II

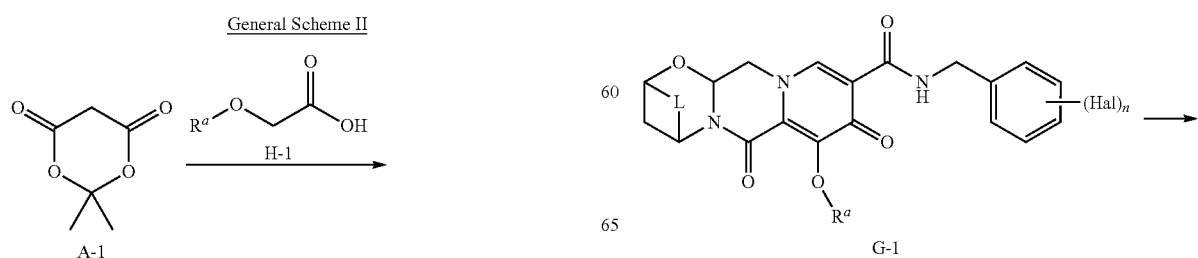

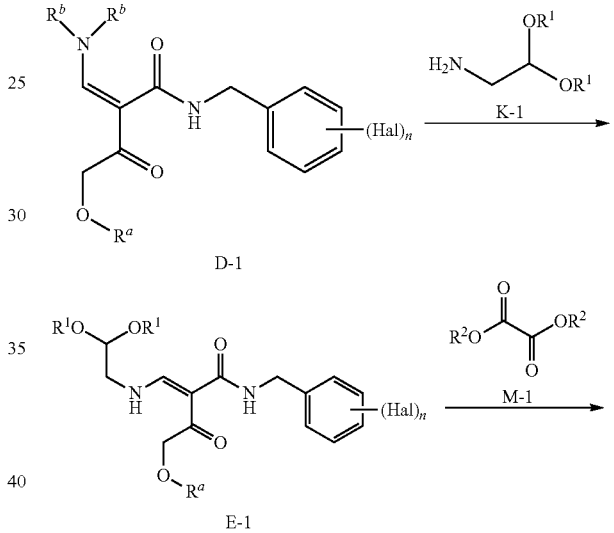

-continued

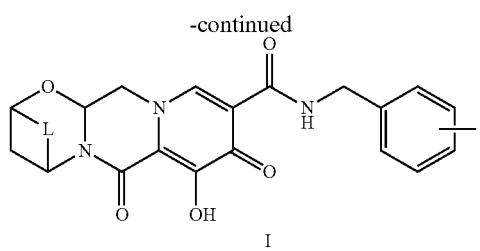

wherein the process comprises the following steps:
- reacting A-1 with H-1 in the presence of a catalyst, a base, and an acylating reagent to yield B-1;
- reacting B-1 with J-1 in the presence of an acid to yield C-1;
- reacting C-1 with an alkylated formamide acetal to yield D-1;
- reacting D-1 with K-1 to yield E-1;
- reacting E-1 with M-1 in the presence of a base to yield F-1;
- reacting F-1 with at least one acid and N-1, in the presence of a base to yield G-1;
- reacting G-1 under conditions suitable to yield a compound of Formula I;

wherein
Hal is halogen,
n is 1, 2, or 3,
L is —C(R$^c$)$_2$—, —C(R$^c$)$_2$C(R$^c$)$_2$—, —C(R$^c$)$_2$C(R$^c$)$_2$C(R$^c$)$_2$—, or —C(R$^c$)$_2$C(R$^c$)$_2$C(R$^c$)$_2$C(R$^c$)$_2$—,
each R$^c$ is, independently, hydrogen, halo, hydroxyl or C$_1$-C$_4$alkyl,
each R$^a$, R$^b$, R$^1$, and R$^2$ is, independently(C$_1$-C$_4$)alkyl, (C$_2$-C$_{10}$)aryl, or (C$_2$-C$_{10}$)aryl (C$_1$-C$_4$)alkyl.

In some embodiments, Hal is halogen, which may be the same or different.

In some embodiments, each R$^a$, R$^b$, R$^1$, and R$^2$ is, independently, (C$_1$-C$_4$)alkyl, (C$_6$-C$_{10}$)aryl, or (C$_6$-C$_{10}$)aryl (C$_1$-C$_4$)alkyl.

In some embodiments, J-1 is in the form of a salt or a co-crystal.

In some embodiments, N-1 is in the form of a salt or a co-crystal.

Another embodiment provides a process to prepare a Compound of Formula I

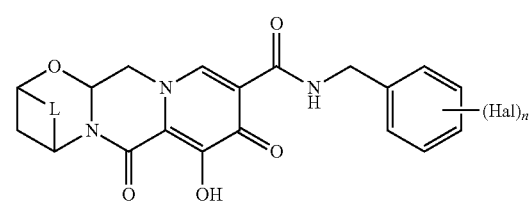

according to the following General Scheme III:

General Scheme III

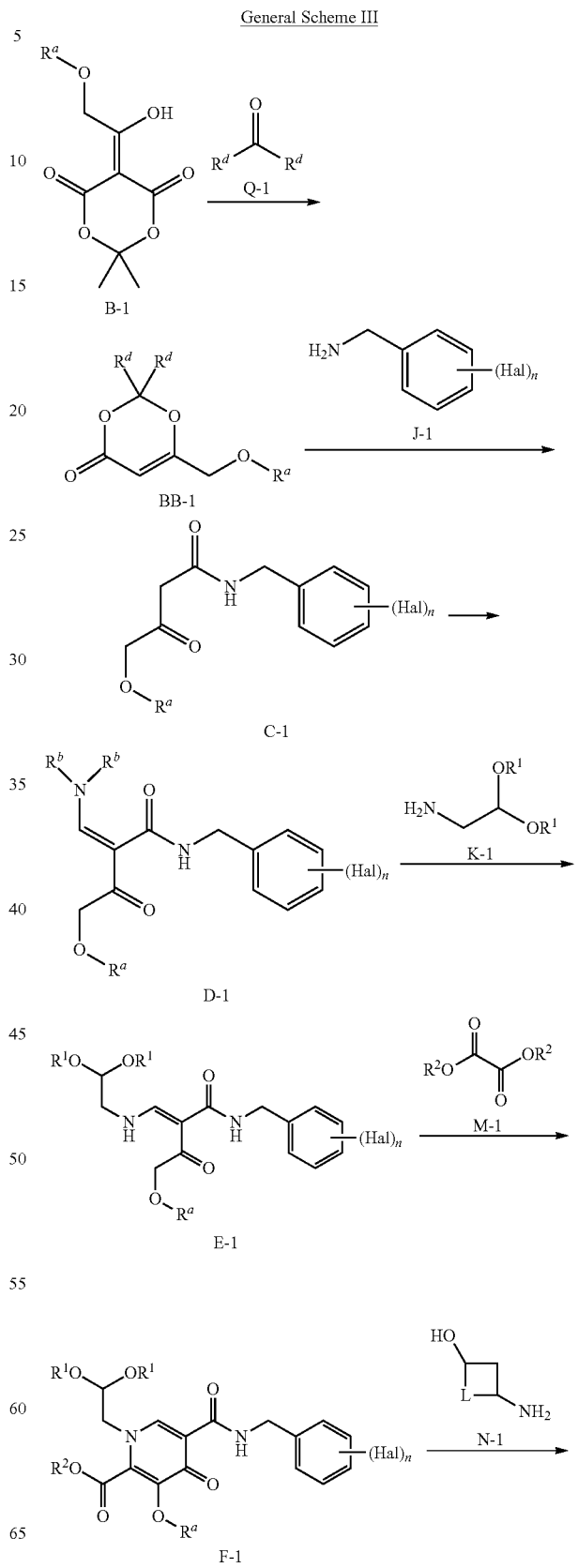

-continued

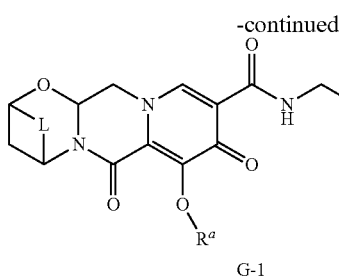

G-1

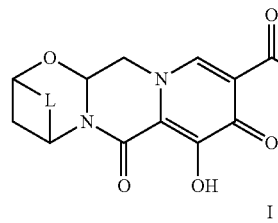

I wherein the process comprises the following steps:
reacting B-1 with Q-1 to yield BB-1 reacting BB-1 with J-1 to yield C-1;
reacting C-1 with an alkylated formamide acetal to yield D-1;
reacting D-1 with K-1 to yield E-1;
reacting E-1 with M-1 in the presence of a base to yield F-1;
reacting F-1 with at least one acid and N-1, or salts or co-crystals thereof, in the presence of a base to yield G-1;
reacting G-1 under conditions suitable to yield a compound of Formula I;
wherein
Hal is halogen,
n is 1, 2, or 3,
L is —C($R^c$)$_2$—, —C($R^c$)$_2$C($R^c$)$_2$—, —C($R^c$)$_2$C($R^c$)$_2$C($R^c$)$_2$—, or —C($R^c$)$_2$C($R^c$)$_2$C($R^c$)$_2$C($R^c$)$_2$—,
each $R^c$ is, independently, hydrogen, halo, hydroxyl or $C_1$-$C_4$alkyl,
each $R^a$, $R^b$, $R^d$, $R^1$, and $R^2$ is, independently, ($C_1$-$C_4$)alkyl, ($C_2$-$C_{10}$)aryl, or ($C_2$-$C_{10}$)aryl ($C_1$-$C_4$)alkyl.

In some embodiments, Hal is halogen, which may be the same or different.

In some embodiments, each $R^a$, $R^b$, $R^d$, $R^1$, and $R^2$ is, independently, ($C_1$-$C_4$)alkyl, ($C_6$-$C_{10}$)aryl, or ($C_6$-$C_{10}$)aryl ($C_1$-$C_4$)alkyl.

In some embodiments, J-1 is in the form of a salt or a co-crystal.

Another embodiment provides a process to prepare a Compound of Formula I

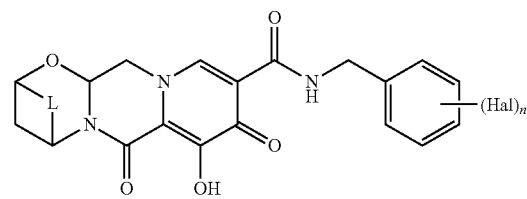

I according to the following General Scheme IV:

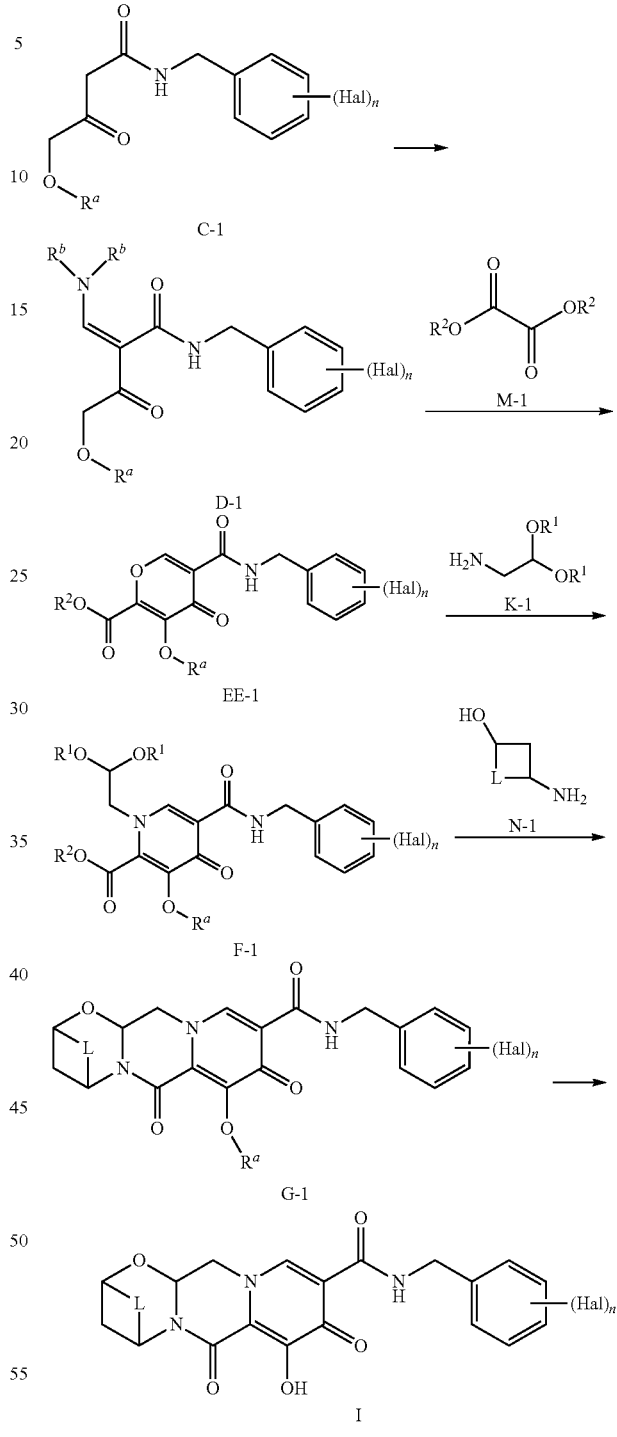

wherein the process comprises the following steps:
reacting C-1 with an alkylated formamide acetal to yield D-1;
reacting D-1 with M-1 to yield EE-1;
reacting EE-1 with K-1 to yield F-1;
reacting F-1 with at least one acid and N-1, in the presence of a base to yield G-1;
reacting G-1 under conditions suitable yield a compound of Formula I;

wherein

Hal is halogen, n is 1, 2, or 3,

L is —C(R$^c$)$_2$—, —C(R$^c$)$_2$C(R$^c$)$_2$—, —C(R$^c$)$_2$C(R$^c$)$_2$C(R$^c$)$_2$—, or —C(R$^c$)$_2$C(R$^c$)$_2$C(R$^c$)$_2$C(R$^c$)$_2$—, each R$^a$ is, independently, hydrogen, halo, hydroxyl or C$_1$-C$_4$alkyl, each R$^a$, R$^b$, R$^1$, and R$^2$ is, independently, (C$_1$-C$_4$)alkyl, (C$_2$-C$_{10}$)aryl, or (C$_2$-C$_{10}$)aryl (C$_1$-C$_4$)alkyl.

In some embodiments, Hal is halogen, which may be the same or different.

In some embodiments, each R$^a$, R$^b$, R$^1$, and R$^2$ is, independently, (C$_1$-C$_4$)alkyl, (C$_6$-C$_{10}$)aryl, or (C$_6$-C$_{10}$)aryl (C$_1$-C$_4$)alkyl.

In some embodiments, N-1 is in the form of a salt or a co-crystal.

Another embodiment provides a process to prepare a compound of Formula II:

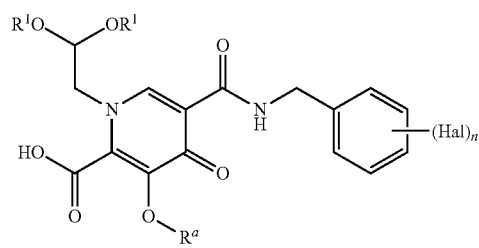

II according to the following General Scheme V:

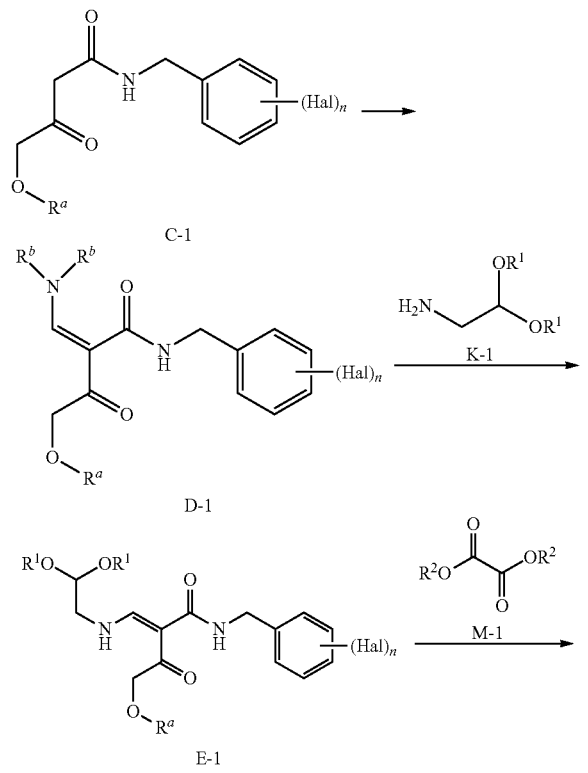

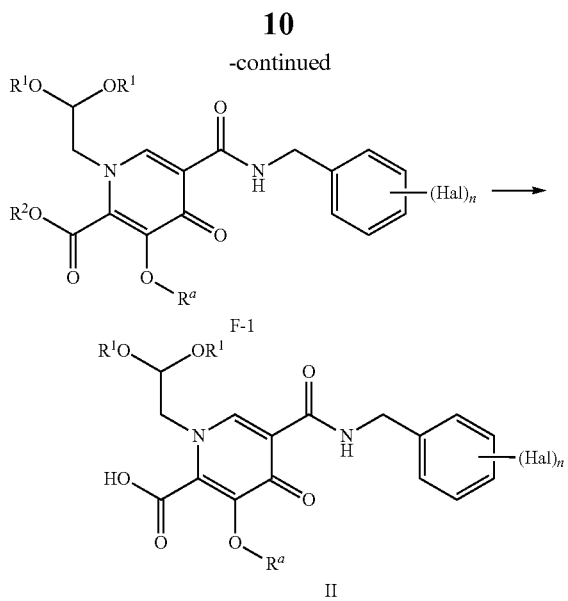

wherein the process comprises the following steps:
- reacting C-1 with an alkylated formamide acetal to yield D-1;
- reacting D-1 with K-1 to yield E-1;
- reacting E-1 with M-1 in the presence of a base to yield F-1;
- reacting F-1 with a base to yield a compound of Formula II, wherein Hal is halogen, n is 1, 2, or 3, each R$^a$, R$^b$, R$^1$, and R$^2$ is, independently, (C$_1$-C$_4$)alkyl, (C$_2$-C$_{10}$)aryl, or (C$_2$-C$_{10}$)aryl (C$_1$-C$_4$)alkyl.

In some embodiments, Hal is halogen, which may be the same or different.

In some embodiments, each R$^a$, R$^b$, R$^1$, and R$^2$ is, independently, (C$_1$-C$_4$)alkyl, (C$_6$-C$_{10}$)aryl, or (C$_6$-C$_{10}$)aryl (C$_1$-C$_4$)alkyl.

Another embodiment provides a process to prepare a Compound of Formula I:

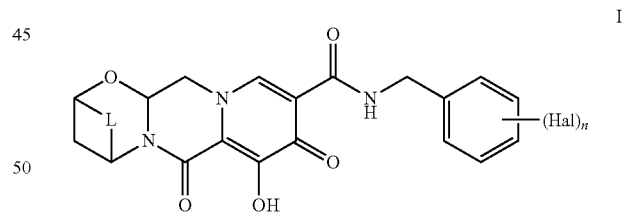

I according to the following General Scheme VI

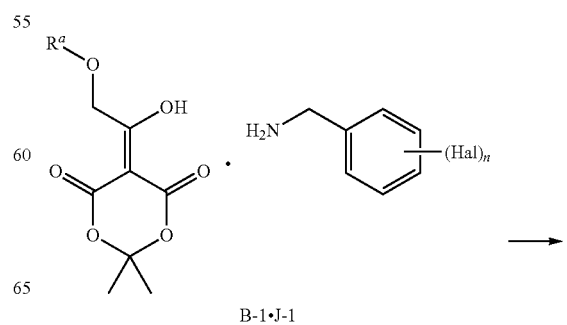

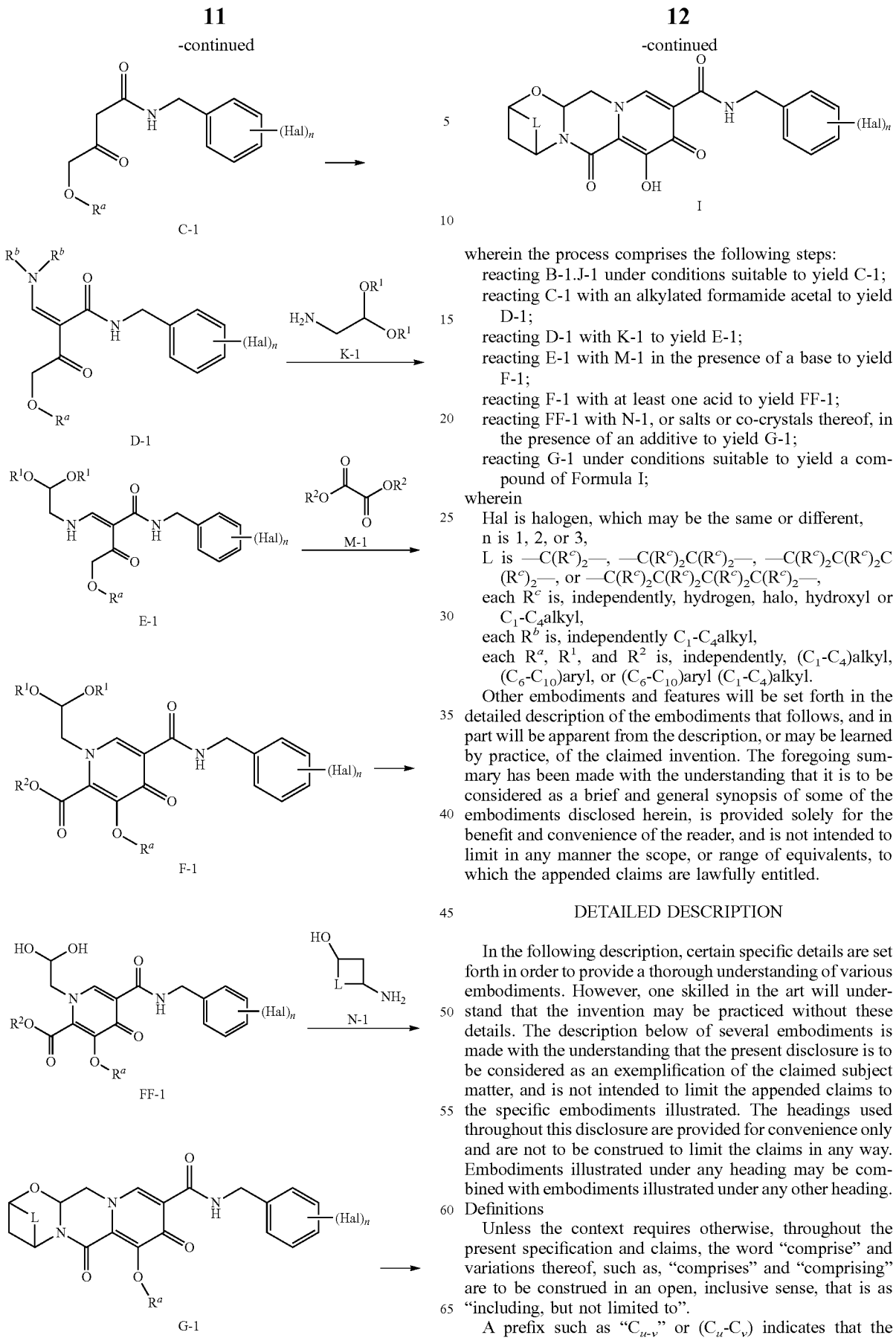

wherein the process comprises the following steps:
reacting B-1.J-1 under conditions suitable to yield C-1;
reacting C-1 with an alkylated formamide acetal to yield D-1;
reacting D-1 with K-1 to yield E-1;
reacting E-1 with M-1 in the presence of a base to yield F-1;
reacting F-1 with at least one acid to yield FF-1;
reacting FF-1 with N-1, or salts or co-crystals thereof, in the presence of an additive to yield G-1;
reacting G-1 under conditions suitable to yield a compound of Formula I;
wherein
Hal is halogen, which may be the same or different,
n is 1, 2, or 3,
L is —C(R$^c$)$_2$—, —C(R$^c$)$_2$C(R$^c$)$_2$—, —C(R$^c$)$_2$C(R$^c$)$_2$C(R$^c$)$_2$—, or —C(R$^c$)$_2$C(R$^c$)$_2$C(R$^c$)$_2$C(R$^c$)$_2$—,
each R$^c$ is, independently, hydrogen, halo, hydroxyl or C$_1$-C$_4$alkyl,
each R$^b$ is, independently C$_1$-C$_4$alkyl,
each R$^a$, R$^1$, and R$^2$ is, independently, (C$_1$-C$_4$)alkyl, (C$_6$-C$_{10}$)aryl, or (C$_6$-C$_{10}$)aryl (C$_1$-C$_4$)alkyl.

Other embodiments and features will be set forth in the detailed description of the embodiments that follows, and in part will be apparent from the description, or may be learned by practice, of the claimed invention. The foregoing summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled.

DETAILED DESCRIPTION

In the following description, certain specific details are set forth in order to provide a thorough understanding of various embodiments. However, one skilled in the art will understand that the invention may be practiced without these details. The description below of several embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

Definitions

Unless the context requires otherwise, throughout the present specification and claims, the word "comprise" and variations thereof, such as, "comprises" and "comprising" are to be construed in an open, inclusive sense, that is as "including, but not limited to".

A prefix such as "C$_{u-v}$" or (C$_u$-C$_v$) indicates that the following group has from u to v carbon atoms. For example, "($C_1$-$C_6$)alkyl" indicates that the alkyl group has from 1 to 6 carbon atoms and ($C_6$-$C_{10}$)aryl($C_1$-$C_6$)alkyl indicates that the aryl portion of the group has from 6 to 10 carbon atoms and the alkyl portion of the group has from one to six carbon atoms.

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —$NH_2$ radical.
"Cyano" refers to the —CN radical.
"Hydroxy" or "hydroxyl" refers to the —OH radical.
"Imino" refers to the =NH substituent.
"Nitro" refers to the —$NO_2$ radical.
"Oxo" refers to the =O substituent.
"Thioxo" refers to the =S substituent.
"BzOH" refers to benzoic acid or

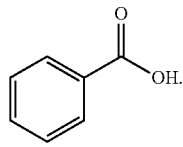

"Alkyl" refers to a straight or branched saturated hydrocarbon chain radical consisting solely of carbon and hydrogen atoms, having from one to twelve carbon atoms ($C_1$-$C_{12}$ alkyl), or one to eight carbon atoms ($C_1$-$C_8$ alkyl), or one to six carbon atoms ($C_1$-$C_6$ alkyl), or one to 4 carbon atoms ($C_1$-$C_4$ alkyl) and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

In some embodiments, "Alkyl" refers to a straight or branched saturated hydrocarbon chain radical consisting solely of carbon and hydrogen atoms, having from one to twelve carbon atoms ($C_1$-$C_{12}$ alkyl), or one to eight carbon atoms ($C_1$-$C_8$ alkyl), or one to six carbon atoms ($C_1$-$C_6$ alkyl), or one to 4 carbon atoms ($C_1$-$C_4$ alkyl) and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group may be optionally substituted.

"Alkenyl" refers to any group derived from a straight or branched hydrocarbon with at least one carbon-carbon double bond. Alkenyl groups include, but are not limited to, ethenyl (vinyl), propenyl (allyl), 1-butenyl, 1,3-butadienyl, and the like. Unless otherwise specified, an alkenyl group has from 2 to about 10 carbon atoms, for example from 2 to 10 carbon atoms, for example from 2 to 6 carbon atoms, for example from 2 to 4 carbon atoms.

"Alkynyl" refers to any group derived from a straight or branched hydrocarbon with at least one carbon-carbon triple bond and includes those groups having one triple bond and one double bond. Examples of alkynyl groups include, but are not limited to, ethynyl (—C≡CH), propargyl (—$CH_2$C≡CH), (E)-pent-3-en-1-ynyl, and the like. Unless otherwise specified, an alkynyl group has from 2 to about 10 carbon atoms, for example from 2 to 10 carbon atoms, for example from 2 to 6 carbon atoms, for example from 2 to 4 carbon atoms.

"Alkoxy" refers to a radical of the formula —$OR^A$ where $R^A$ is an alkyl radical as defined above containing one to twelve carbon atoms, or one to eight carbon atoms, or one to six carbon atoms, or one to four carbon atoms. Unless stated otherwise specifically in the specification, an alkoxy group may be optionally substituted.

"Alkylamino" refers to a radical of the formula —$NHR^A$ or —$NR^A R^A$ where each $R_A$ is, independently, an alkyl radical as defined above containing one to twelve carbon atoms, or one to eight carbon atoms, or one to six carbon atoms, or one to four carbon atoms. Unless stated otherwise specifically in the specification, an alkylamino group may be optionally substituted.

"Thioalkyl" refers to a radical of the formula —$SR^A$ where $R^A$ is an alkyl radical as defined above containing one to twelve carbon atoms, or one to eight carbon atoms, or one to six carbon atoms, or one to four carbon atoms. Unless stated otherwise specifically in the specification, a thioalkyl group may be optionally substituted.

"Aryl" refers to a monocyclic hydrocarbon ring system radical comprising hydrogen and 6 to 18 carbon atoms, or 6 to 10 carbon atoms or 6 to 8 carbon atoms. Aryl radicals include, but are not limited to, aryl radicals derived from benzene. Unless stated otherwise specifically in the specification, the term "aryl" or the prefix "ar-" (such as in "aralkyl") is meant to include aryl radicals that are optionally substituted.

"Arylalkyl" (also "aralkyl") refers to a radical of the formula —$R^B$—$R^C$ where $R^B$ is an alkyl group as defined above and $R_C$ is one or more aryl radicals as defined above, for example, benzyl. Arylalkyl groups include, but are not limited to, those groups derived from benzyl, tolyl, dimethylphenyl, 2-phenylethan-1-yl, 2-naphthylmethyl, phenylmethylbenzyl, 1,2,3,4-tetrahydronapthyl, and the like. An arylalkyl group comprises from 6 to about 30 carbon atoms, for example the alkyl group can comprise from 1 to about 10 carbon atoms and the aryl group can comprise from 5 to about 20 carbon atoms. Unless stated otherwise specifically in the specification, an aralkyl group may be optionally substituted.

In some embodiments, "Arylalkyl" (also "aralkyl") refers to a radical of the formula —$R^B$-$R^C$ where $R^B$ is an alkyl group as defined above and $R^C$ is one or more aryl radicals as defined above, for example, benzyl. Arylalkyl groups include, but are not limited to, those groups derived from benzyl, tolyl, dimethylphenyl, 2-phenylethan-1-yl, 2-naphthylmethyl, phenylmethylbenzyl, 1,2,3,4-tetrahydronapthyl, and the like. An arylalkyl group comprises from 6 to about 30 carbon atoms, for example the alkyl group can comprise from 1 to about 10 carbon atoms and the aryl group can comprise from 6 to about 20 carbon atoms. Unless stated otherwise specifically in the specification, an aralkyl group may be optionally substituted.

"Cycloalkyl" refers to a cyclic alkyl group. A cycloalkyl group can have one or more cyclic rings and includes fused and bridged groups. Examples include, but are not limited to, cyclopropyl, cyclobutyl, cyclopentyl, cyclohexyl, adamantyl, and the like. Unless otherwise stated specifically in the specification, a carbocyclic group may be optionally substituted.

"Carbocyclic ring" or "carbocycle" refers to a stable non-aromatic monocyclic hydrocarbon radical consisting solely of carbon and hydrogen atoms, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Unless otherwise stated specifically in the specification, a carbocyclic group may be optionally substituted.

"Cycloalkylalkyl" refers to a radical of the formula —$R_B R_D$ where $R_B$ is an alkyl group as defined above and $R^D$ is a carbocyclic radical as defined above. Unless stated otherwise specifically in the specification, a cycloalkylalkyl group may be optionally substituted.

In some embodiments, "Cycloalkylalkyl" refers to a radical of the formula —$R_B R_D$ where $R_B$ is an alkyl group as defined above and $R_D$ is a carbocyclic radical as defined above. Unless stated otherwise specifically in the specification, a cycloalkylalkyl group may be optionally substituted.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. In some embodiments, the heterocyclyl radical is a 3 to 12 membered non-aromatic ring, or a 3 to 8 membered non-aromatic ring, or a 3 to 6 membered non-aromatic ring. In some embodiments, the heterocyclyl radical contains one to four heteroatoms, or one to three heteroatoms, or one to two heteroatoms, or one heteroatom. In the embodiments disclosed herein, the heterocyclyl radical is a monocyclic ring system; and the heterocyclyl radical may be partially or fully saturated. Examples of such heterocyclyl radicals include, but are not limited to, dioxolanyl, thienyl, [1,3] dithianyl, imidazolinyl, imidazolidinyl, isothiazolidinyl, isoxazolidinyl, morpholinyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group may be optionally substituted.

In some embodiments, "Heterocyclyl" or "heterocyclic ring" refers to a stable 4- to 18-membered non-aromatic ring radical which consists of 3 to 17 carbon atoms and from one to six heteroatoms selected from the group consisting of nitrogen, oxygen and sulfur. In some embodiments, the heterocyclyl radical is a 4 to 12 membered non-aromatic ring, or a 4 to 8 membered non-aromatic ring, or a 4 to 6 membered non-aromatic ring. In some embodiments, the heterocyclyl radical contains one to four heteroatoms, or one to three heteroatoms, or one to two heteroatoms, or one heteroatom. Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, an N-heterocyclyl group may be optionally substituted.

"Heterocyclylalkyl" refers to a radical of the formula —$R_B R_E$ where $R_B$ is an alkylgroup as defined above and $R_E$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to an aryl group in which one or more of the carbon atoms (and any associated hydrogen atoms) are each independently replaced with the the same or different heteroatom selected from the group consisting of nitrogen, oxygen and sulfur. Unless otherwise specified, an heteroaryl group has from 5 to about 20 carbon atoms, for example from 5 to 18 carbon atoms, for example from 5 to 14 carbon atoms, for example from 5 to 10 carbon atoms. Heteroaryl groups have from one to six heteroatoms, from one to four heteroatoms, from one to three heteroatoms, from one to two heteroatoms or one heteroatom. Unless stated otherwise specifically in the specification, a heteroaryl group may be optionally substituted.

In some, embodiments, "Heteroaryl" refers to an aryl group in which one or more of the carbon atoms (and any associated hydrogen atoms) are each independently replaced with the the same or different heteroatom selected from the group consisting of nitrogen, oxygen and sulfur. Heteroaryl groups include, but are not limited to, groups derived from furan, imidazole, isothiazole, isoxazole, oxadiazole, oxazole, pyrazine, pyrazole, pyridazine, pyridine, pyrimidine, pyrrole, tetrazole, thiadiazole, thiazole, thiophene, triazole, and the like. Unless otherwise specified, an heteroaryl group has from 5 to about 20 carbon atoms, for example from 5 to 18 carbon atoms, for example from 5 to 14 carbon atoms, for example from 5 to 10 carbon atoms. Heteroaryl groups have from one to six heteroatoms, from one to four heteroatoms, from one to three heteroatoms, from one to two heteroatoms or one heteroatom. Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —$R_B R_F$ where $R_B$ is an alkyl group as defined above and $R_F$ is a heteroaryl radical as defined above. Unless stated otherwise specifically in the specification, a heteroarylalkyl group may be optionally substituted.

The term "substituted" used herein means any of the above groups (i.e., alkyl, alkylene, alkoxy, alkylamino, thioalkyl, aryl, aralkyl, carbocycle, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_GR_H$, —$NR_GC(=O)R_H$, —$NR_GC(=O)NR_GR_H$, —$NR_GC(=O)OR_H$, —$NR_GC(=NR_g)NR_GR_H$, —$NR_GSO_2R_H$, —$OC(=O)NR_GR_H$, —$OR_G$, —$SR_G$, —$SOR_G$, —$SO_2R_G$, —$OSO_2R_G$, —$SO_2OR_G$, =$NSO_2R_G$, and —$SO_2NR_GR_H$. "Substituted also means any of the above groups in which one or more hydrogen atoms are replaced with —$C(=O)R_G$, —$C(=O)OR_G$, —$C(=O)NR_GR_H$, —$CH_2SO_2R_G$, —$CH_2SO_2NR_GR_H$. In the foregoing, $R_G$ and $R_H$ are the same or different and independently hydrogen, alkyl, alkoxy, alkylamino, thioalkyl, aryl, aralkyl, carbocycle, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, carbocycle, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

The term "alkylated formamide acetal" as used herein, refers to a compound of Formula:

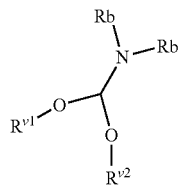

wherein each $R^b$ is independently $(C_1-C_4)$alkyl, $R^{v1}$ and $R^{v2}$ are independently $(C_1-C_6)$alkyl or $R^{v1}$ and $R^{v2}$ together with the atoms to which they are attached form a 5 to 10 membered heterocyclyl.

"Alkylated formamide acetal" includes, but is not limited to N,N-dimethylformamide dimethyl acetal, N,N-dimethylformamide diethyl acetal, N,N-dimethylformamide diisopropyl acetal, N,N-diethylformamide dimethyl acetal, and N,N-diisopropylformamide dimethyl acetal.

The term "acyl donor" as used herein, refers to a reactive compound which transfers a group —CO—$R^x$ onto another molecule, wherein $R^x$ is $(C_1-C_6)$alkyl-$R^y$ and $R^y$ is selected from the group consisting of H, CN, —$NR^{z1}R^{z2}$, $C(O)R^{z1}$, —$C(O)OR^{z1}$, —$C(O)NR^{z1}R^{z2}$, —$OC(O)NR^{z1}R^{z2}$, —$NR^{z1}C(O)R^{z2}$, —$NR^{z1}$, $C(O)NR^{z2}$, —$NR^{z1}C(O)OR^{z2}$, —$S(O)_{1-2}R^{z1}$, —$S(O)_2NR^{z1}R^{z2}$, $S(O)_2R^{z2}$, $NR^{z1}S(O)_2R^{z2}$, and $OR^{z1}$ and $R^{z2}$ are independently selected from the group consisting of H, $C_{1-6}$alkyl, $C_{2-6}$alkenyl, $C_{2-6}$alkynyl, $C_{1-6}$heteroalkyl, $C_{3-10}$cycloalkyl, 3 to 12 membered heterocyclyl, $C_{6-10}$aryl and 5 to 10 membered heteroaryl. In certain embodiments, $R^y$ is H. In certain embodiments, $R^{z1}$ and $R^{z2}$ are independently selected from the group consisting of H and $C_{1-6}$alkyl. Acyl donors include but are not limited to anhydrides, esters and acid chlorides such as succinic anhydride, glutaric anhydride, acetic anhydride, vinyl acetate, isopropenyl acetate, 4-chlorophenyl acetate, ethyl methoxy acetate, acetyl chloride and benzoyl chloride.

A person skilled in the art will understand that throughout this application, and more specifically in Schemes I, II, III, V and VI, compound E-1 may exist in an E or in a Z configuration or as a mixture of an E and Z configuration. Accordingly, in certain embodiments, compound E-1 is in an E or a Z configuration, or a mixture thereof. In certain embodiments, compound E-1 is in an E configuration. In certain embodiments, compound E-1 is in an Z configuration. In certain embodiments, compound E-1 is in a mixture of Z and E configurations.

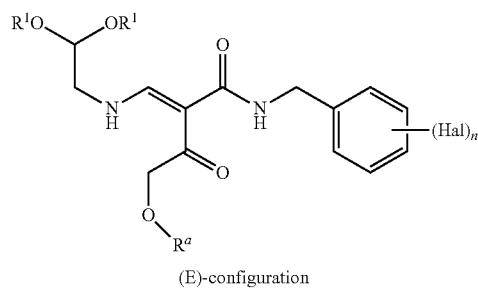

(E)-configuration

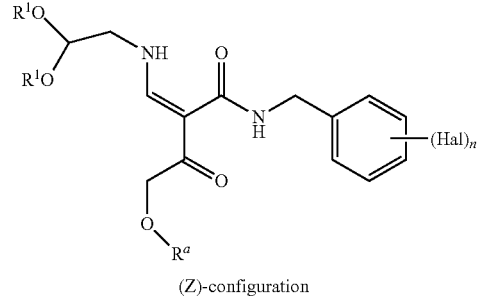

(Z)-configuration

A person skilled in the art will understand that throughout this application, compound B-1.J-1 is a salt:

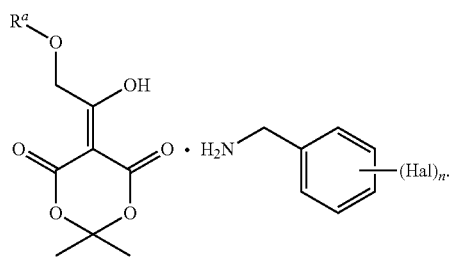

B-1•J-1

The term "protecting group," as used herein, refers to a labile chemical moiety which is known in the art to protect reactive groups including without limitation, hydroxyl and amino groups, against undesired reactions during synthetic procedures. Hydroxyl and amino groups protected with a protecting group are referred to herein as "protected hydroxyl groups" and "protected amino groups", respectively. Protecting groups are typically used selectively and/or orthogonally to protect sites during reactions at other reactive sites and can then be removed to leave the unprotected group as is or available for further reactions. Protecting groups as known in the art are described generally in Greene and Wuts, Protective Groups in Organic Synthesis, 3rd edition, John Wiley & Sons, New York (1999). Generally, groups are protected or present as a precursor that will be inert to reactions that modify other areas of the parent molecule for conversion into their final groups at an appropriate time. Further representative protecting or precursor groups are discussed in Agrawal, et al., Protocols for Oligonucleotide Conjugates, Eds, Humana Press; New Jersey, 1994; Vol. 26 pp. 1-72. Examples of "hydroxyl protecting groups" include, but are not limited to, t-butyl, t-butoxymethyl, methoxymethyl, tetrahydropyranyl, 1-ethoxyethyl, 1-(2-chloroethoxy)ethyl, 2-trimethy lsilylethyl, p-chlorophenyl, 2,4-dinitrophenyl, benzyl, 2,6-dichlorobenzyl, diphenylmethyl, p-nitrobenzyl, triphenylmethyl, trimethylsilyl, triethylsilyl, t-butyldimethylsilyl, t-butyldiphenylsilyl (TBDPS), triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate. Examples of "amino protecting groups" include, but are not limited to, carbamate-protecting groups, such as 2-trimethylsilylethoxycarbonyl (Teoc), 1-methyl-1-(4-biphenylyl)ethoxy-carbonyl (Bpoc), t-butoxycarbonyl (BOC), allyloxycarbonyl (Alloc), 9-fluoreny lmethy loxycarbonyl (Fmoc), and benzyloxycarbonyl (Cbz); amide protecting groups, such as formyl, acetyl, trihaloacetyl, benzoyl, and nitrophenylacetyl; sulfonamide-protecting groups, such as 2-nitrobenzenesulfonyl; and imine and cyclic imide protecting groups, such as phthalimido and dithiasuccinoyl.

The invention disclosed herein is also meant to encompass all pharmaceutically acceptable compounds of Formula I and compounds of Formula II being isotopically-labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabeled compounds could be useful to help determine or measure the effectiveness of the compounds, by characterizing, for example, the site or mode of action, or binding affinity to pharmacologically important site of action. Certain isotopically-labeled compounds of Formula I and compounds of Formula II, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability. For example, in vivo half-life may increase or dosage requirements may be reduced. Thus, heavier isotopes may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Formula I and compounds of Formula II can generally be prepared by conventional techniques known to those skilled in the art or by processes analogous to those described in the Examples as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabeled compound described in the embodiments herein in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Lewis acid" refers to a group that can accept a nonbonding pair of electrons, i.e., an electron-pair acceptor. Lewis acids are able to react with a Lewis base to form a Lewis adduct, by sharing the electron pair supplied by the Lewis base.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" refers to a salt of a compound that is pharmaceutically acceptable and that possesses (or can be converted to a form that possesses) the desired pharmacological activity of the parent compound. Examples of "pharmaceutically acceptable salts" of the compounds disclosed herein include salts derived from an appropriate base, such as an alkali metal (for example, sodium), an alkaline earth metal (for example, magnesium), ammonium and $NX_4^+$ (wherein X is $C_1$-$C_4$ alkyl). Pharmaceutically acceptable salts of a nitrogen atom or an amino group include for example salts of organic carboxylic acids such as acetic, benzoic, camphorsulfonic, citric, glucoheptonic, gluconic, lactic, fumaric, tartaric, maleic, malonic, malic, mandelic, isethionic, lactobionic, succinic, 2-napthalenesulfonic, oleic, palmitic, propionic, stearic, and trimethylacetic acids; organic sulfonic acids, such as methanesulfonic, ethanesulfonic, benzenesulfonic and p-toluenesulfonic acids; and inorganic acids, such as hydrochloric, hydrobromic, sulfuric, nitric, phosphoric and sulfamic acids. Pharmaceutically acceptable salts of a compound of a hydroxy group include the anion of said compound in combination with a suitable cation such as $Na^+$ and $NX_4^+$ (wherein X is independently selected from H or a $C_1$-$C_4$ alkyl group). Pharmaceutically acceptable salts also include salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., J. Pharma Sci., 66(1), 1-19 (1977), and Remington: The Science and Practice of Pharmacy, R. Hendrickson, ed., 21st edition, Lippincott, Williams & Wilkins, Philadelphia, Pa., (2005), at p. 732, Table 38-5, both of which are hereby incorporated by reference herein.

For therapeutic use, salts of active ingredients of the compounds disclosed herein will typically be pharmaceutically acceptable, i.e. they will be salts derived from a physiologically acceptable acid or base. However, salts of acids or bases which are not pharmaceutically acceptable may also find use, for example, in the preparation or purification of a compound of Formula I, a compound of Formula II or another compound described herein. All salts, whether or not derived from a physiologically acceptable acid or base, are within the scope of the present invention.

Metal salts refer to salts wherein the cation is a metal, such as those formed when an acidic proton present in a compound is replaced by either a metal ion, e.g., an alkali metal ion, an alkaline earth ion, or an aluminium ion; or a metal ion coordinates with an organic base such as diethanolamine, triethanolamine, N-methylglucamine and the like.

The metal can be an alkali metal, alkaline earth metal, transition metal, or main group metal. Non-limiting examples of suitable metals include lithium, sodium, potassium, cesium, cerium, magnesium, manganese, iron, calcium, strontium, cobalt, titanium, aluminum, copper, cadmium, and zinc.

Non-limiting examples of suitable metal salts include a lithium salt, a sodium salt, a potassium salt, a cesium salt, a cerium salt, a magnesium salt, a manganese salt, an iron salt, a calcium salt, a strontium salt, a cobalt salt, a titanium salt, a aluminum salt, a copper salt, a cadmium salt, and a zinc salt.

In addition, salts may be formed from acid addition of certain organic and inorganic acids, e.g., HCl, HBr, $H_2SO_4$, $H_3PO_4$ or organic sulfonic acids, to basic centers, typically amines.

Finally, it is to be understood that the compositions herein comprise compounds disclosed herein in their un-ionized, as well as zwitterionic form, and combinations with stoichiometric amounts of water as in hydrates.

Often crystallizations produce a solvate of the compound described in the embodiments disclosed herein. As used herein, the term "solvate" refers to an aggregate that comprises one or more molecules of a compound described herein with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compounds described herein may be true solvates, while in other cases, the compound described herein may merely retain adventitious water or be a mixture of water plus some adventitious solvent.

A "pharmaceutical composition" refers to a formulation of a compound described herein and a medium generally accepted in the art for the delivery of the biologically active compound to mammals, e.g., humans. Such a medium includes all pharmaceutically acceptable carriers, diluents or excipients therefor.

"Effective amount" or "therapeutically effective amount" refers to an amount of a compound according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds described herein, and the age, body weight, general health, sex and diet of the patient. Such a therapeutically effective amount can be determined routinely by one of ordinary skill in the art having regard to their own knowledge, the state of the art, and this disclosure.

The term "treatment" as used herein is intended to mean the administration of a compound or composition according to the present invention to alleviate or eliminate symptoms of HIV infection and/or to reduce viral load in a patient. The term "treatment" also encompasses the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectible levels in the blood, and the administration of a compound or composition according to the present invention to prevent perinatal transmission of HIV from mother to baby, by administration to the mother before giving birth and to the child within the first days of life.

The term "antiviral agent" as used herein is intended to mean an agent (compound or biological) that is effective to inhibit the formation and/or replication of a virus in a human being, including but not limited to agents that interfere with either host or viral mechanisms necessary for the formation and/or replication of a virus in a human being.

The term "inhibitor of HIV replication" as used herein is intended to mean an agent capable of reducing or eliminating the ability of HIV to replicate in a host cell, whether in vitro, ex vivo or in vivo.

The compounds described herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

An "enantioenriched" compound refers to a compound which contains more than 50% of one of a pair of enantiomers. An "enantioenriched" compound may have an enantiomeric excess (% ee) of over 5%, over 10%, over 20%, over 30%, over 40%, over 50%, over 60%, over 70%, over 80%, over 90%, over 95%, over 99%, or over 99.9%.

Reference to "about" a value or parameter herein includes (and describes) embodiments that are directed to that value or parameter per se. For example, description referring to "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

General Schemes

Certain embodiments are directed to the multistep general synthetic methods described below, namely General Schemes I-VI. All substituent groups in the steps described below are as defined as follows:

Hal is halogen,
n is 1, 2, or 3,
L is —C($R^c$)$_2$—, —C($R^c$)$_2$C($R^c$)$_2$—, —C($R^c$)$_2$C($R^c$)$_2$C($R^c$)$_2$—, or —C($R^c$)$_2$C($R^c$)$_2$C($R^c$)$_2$C($R^c$)$_2$—,
each $R^c$ is, independently, hydrogen, halo, hydroxyl or $C_1$-$C_4$alkyl,
each $R^a$, $R^b$, $R^d$, $R^1$, and $R^2$ is, independently, alkyl, aryl, or aralkyl.

In some embodiments, Hal is halogen, which may be the same or different.

In certain embodiments, each $R^a$, $R^b$, $R^d$, $R^1$, and $R^2$ is, independently, ($C_1$-$C_4$)alkyl, ($C_2$-$C_{10}$)aryl, or ($C_2$-$C_{10}$)aryl($C_1$-$C_4$)alkyl.

In some embodiments, each $R^a$, $R^b$, $R^1$, and $R^2$ is, independently, ($C_1$-$C_4$)alkyl, ($C_6$-$C_{10}$)aryl, or ($C_6$-$C_{10}$)aryl($C_1$-$C_4$)alkyl.

In certain embodiments, each $R^b$ is, independently, ($C_1$-$C_4$)alkyl.

In certain embodiments, each $R^c$ is, independently, hydrogen, —F, —Cl, hydroxyl, or methyl. In certain embodiments, each $R^c$ is, independently, hydrogen, —F, or —Cl. In certain embodiments, each $R^c$ is hydrogen.

In certain embodiments, each $R^a$, $R^b$, $R^d$, $R^1$, and $R^2$ is, independently, methyl, ethyl, phenyl, or benzyl. In certain embodiments, each $R^a$, $R^b$, $R^1$, and $R^2$ is methyl. In particular embodiments, $R^d$ is ethyl.

In certain embodiments, each $R^1$ is $C_1$-$C_4$alkyl and each $R^1$, together along with the atoms to which they are bonded, forms a heterocycle. In certain embodiments, each $R^1$ is methyl or ethyl, and each $R^1$, together along with the atoms to which they are bonded, forms a heterocycle. In certain embodiments, each $R^1$ is methyl, and each $R^1$, together along with the atoms to which they are bonded, forms a heterocycle General Scheme I:

In certain embodiments, a process according to general scheme I is provided:

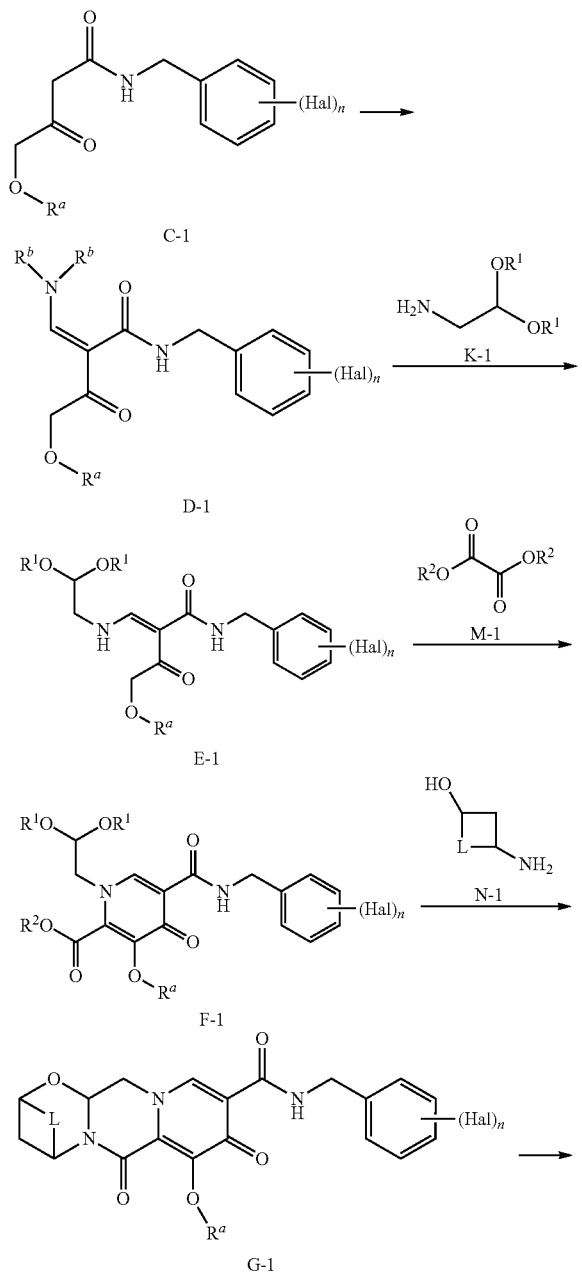

-continued

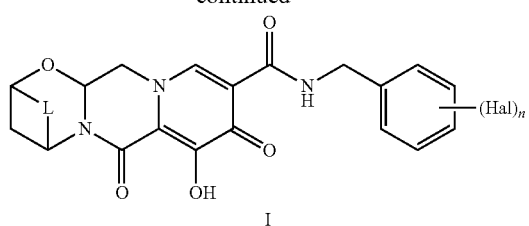

I wherein the process comprises the following steps:
reacting C-1 with an alkylated formamide acetal to yield D-1;
reacting D-1 with K-1 to yield E-1;
reacting E-1 with M-1 in the presence of a base to yield F-1;
reacting F-1 with at least one acid and N-1, or salts or co-crystals thereof, in the presence of a base to yield G-1;
reacting G-1 under conditions suitable to yield a compound of Formula I.

In some embodiments, N-1 is in the form of a salt or a co-crystal.

General Scheme II:

In certain embodiments, a process according to general scheme I is provided:

General Scheme II

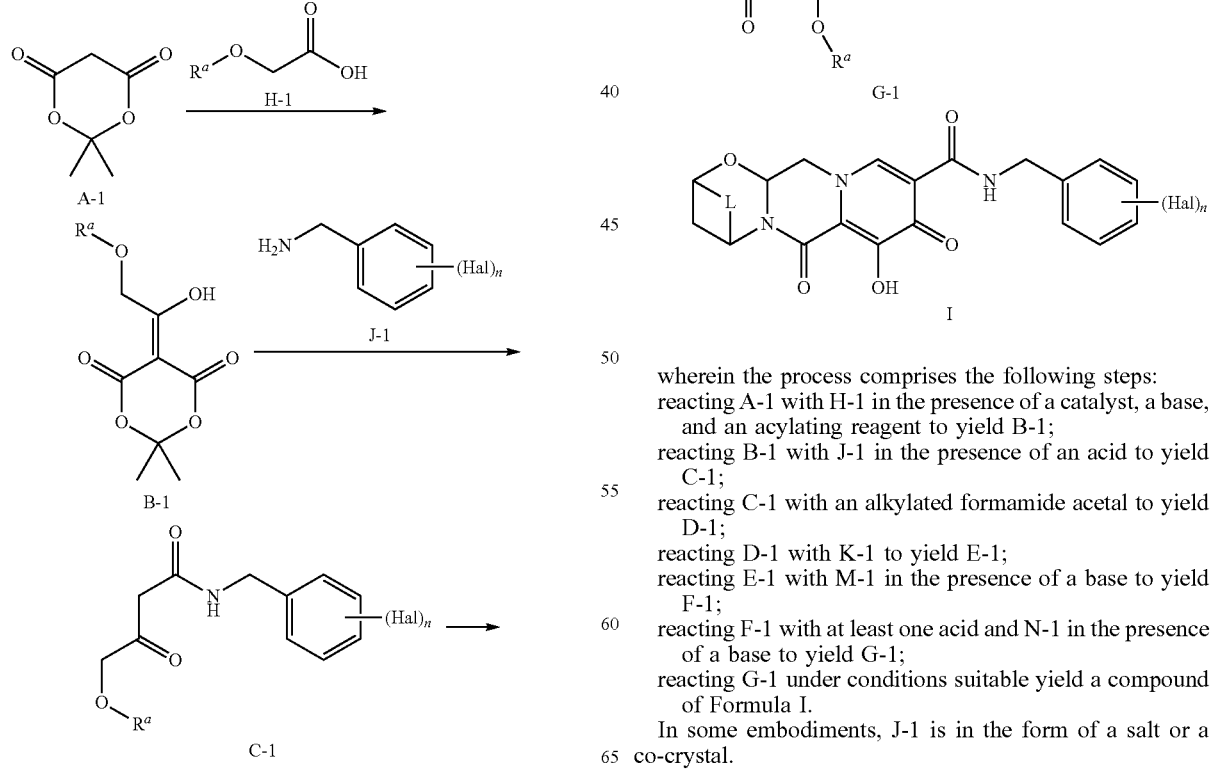

-continued

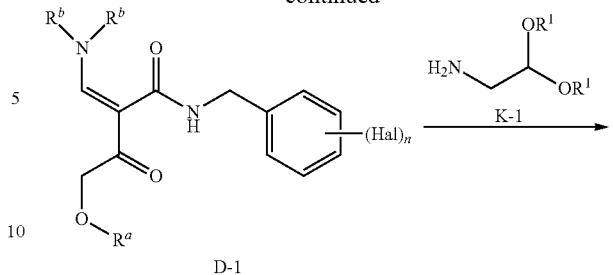

wherein the process comprises the following steps:
reacting A-1 with H-1 in the presence of a catalyst, a base, and an acylating reagent to yield B-1;
reacting B-1 with J-1 in the presence of an acid to yield C-1;
reacting C-1 with an alkylated formamide acetal to yield D-1;
reacting D-1 with K-1 to yield E-1;
reacting E-1 with M-1 in the presence of a base to yield F-1;
reacting F-1 with at least one acid and N-1 in the presence of a base to yield G-1;
reacting G-1 under conditions suitable yield a compound of Formula I.

In some embodiments, J-1 is in the form of a salt or a co-crystal.

In some embodiments, N-1 is in the form of a salt or a co-crystal.

General Scheme III:

In certain embodiments, a process according to general scheme I is provided:

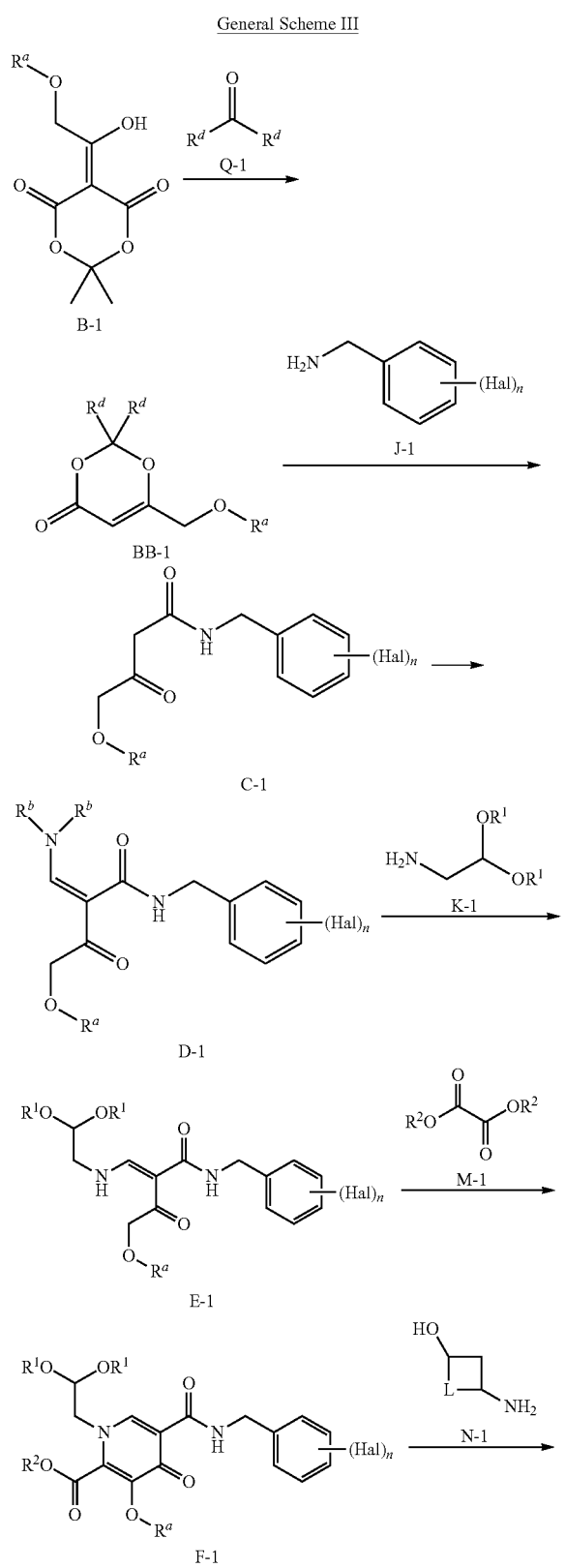

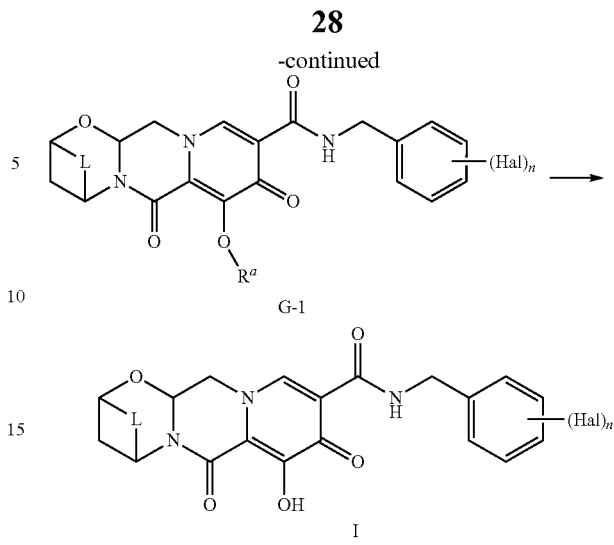

wherein the process comprises the following steps:

reacting B-1 with Q-1 to yield BB-1 reacting BB-1 with J-1 to yield C-1;

reacting C-1 with an alkylated formamide acetal to yield D-1;

reacting D-1 with K-1 to yield E-1;

reacting E-1 with M-1 in the presence of a base to yield F-1;

reacting F-1 with at least one acid and N-1, or salts or co-crystals thereof, in the presence of a base to yield G-1;

reacting G-1 under conditions suitable to yield a compound of Formula I.

In some embodiments, J-1 is in the form of a salt or a co-crystal.

General Scheme IV:

In certain embodiments, a process according to general scheme I is provided:

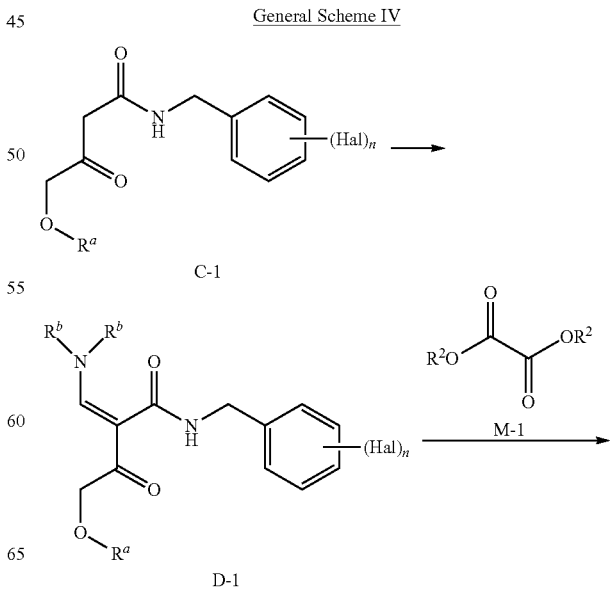

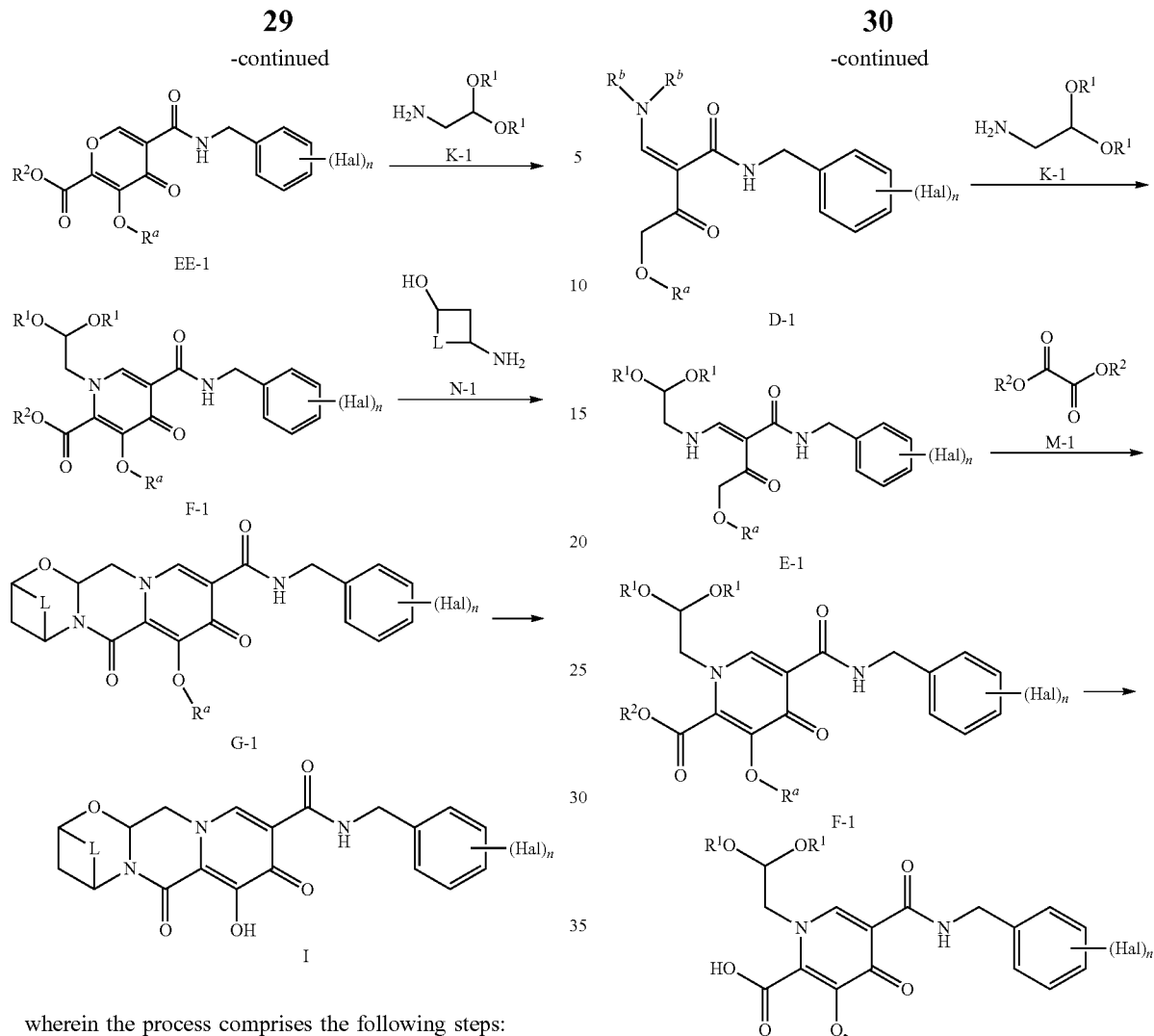

wherein the process comprises the following steps:
reacting C-1 with an alkylated formamide acetal to yield D-1;
reacting D-1 with M-1 to yield EE-1;
reacting EE-1 with K-1 to yield F-1;
reacting F-1 with at least one acid and N-1, in the presence of a base to yield G-1;
reacting G-1 under conditions suitable to yield a compound of Formula I.

In some embodiments, N-1 is in the form of a salt or a co-crystal.

General Scheme V

In certain embodiments, a process according to general scheme I is provided:

General Scheme V wherein the process comprises the following steps:
reacting C-1 with an alkylated formamide acetal to yield D-1;
reacting D-1 with K-1 to yield E-1;
reacting E-1 with M-1 in the presence of a base to yield F-1;
reacting F-1 with a base to yield a compound of Formula II.

General Scheme VI

In certain embodiments, a process according to general scheme I is provided:

General scheme VI

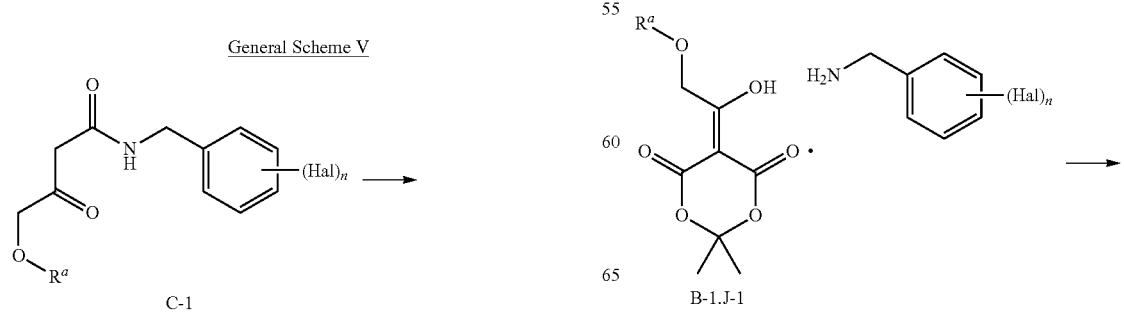

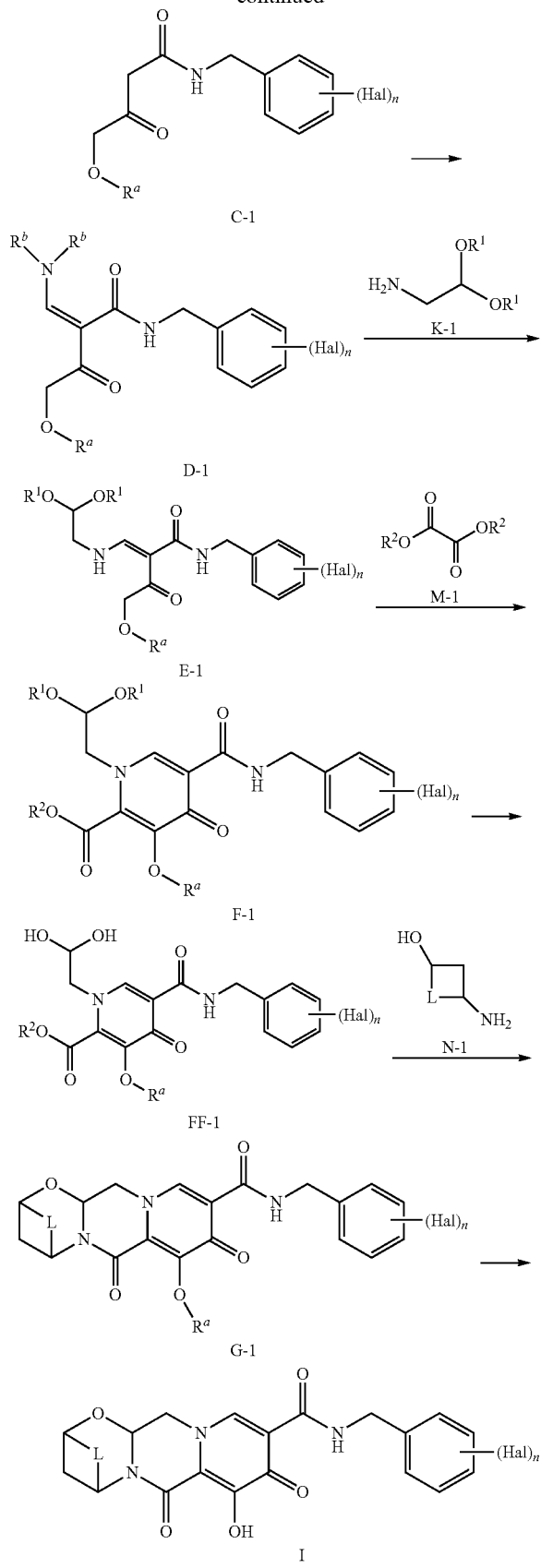

wherein the process comprises the following steps:
reacting B-1.J-1 under conditions suitable to yield C-1;
reacting C-1 with an alkylated formamide acetal to yield D-1;
reacting D-1 with K-1 to yield E-1;
reacting E-1 with M-1 in the presence of a base to yield F-1;
reacting F-1 with at least one acid to yield FF-1;
reacting FF-1 with N-1, or salts or co-crystals thereof, in the presence of an additive to yield G-1;
reacting G-1 under conditions suitable to yield a compound of Formula I.

In some embodiments reacting F-1 with at least one acid yields the following aldehyde:

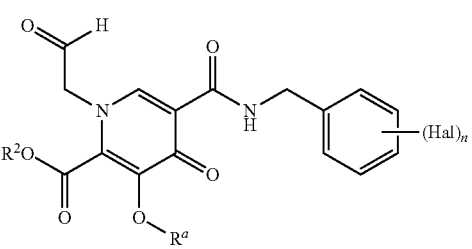

which is hydrated to give FF-1.

General Scheme VII

Certain embodiments are directed to the multistep synthetic method described below, namely General Scheme VII:

General scheme VII

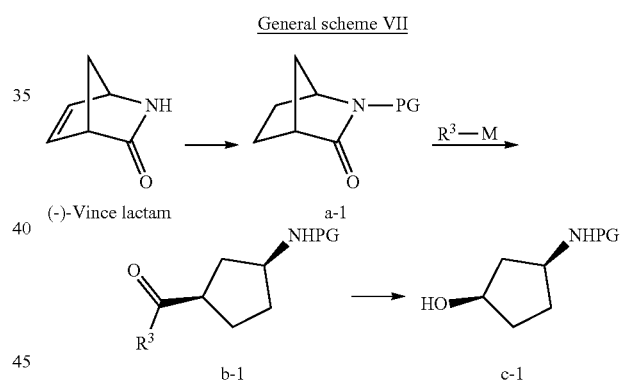

wherein the process comprises the following steps:
hydrogenating (−)-Vince lactam and protecting the reduced product to yield a-1;
reacting a-1 with $R^3$-M to yield b-1;
oxidizing b-1 and hydrolyzing the product of the oxidation to yield c-1.

In General Scheme VII:
PG is a protecting group; and
$R^3$M is a n-alkyl Grignard reagent or an alkyl organolithium reagent.

In certain embodiments, the protecting group (PG) is selected from the group consisting of Boc, phtalimide, benzyl, FMoc, acetyl, triphenylmethyl, trifluoroacetyl, benzylidene, p-Toluenesulfonamide, p-Methoxybenzyl carbonyl, benzoyl, p-methoxybenzyl, carbamates, 3,4-Dimethoxybenzyl, p-methoxyphenyl, sulfonamides and carbobenzyloxy. In particular embodiments, the protecting group is Boc.

In certain embodiments, $R^3$M is an ethylmagnesium halide, an n-propylmagnesium halide, and n-butylmagnesium halide, methyl lithium, n-butyllithium, or n-hexyllithium. In particular embodiments, R³M is methyl magnesium bromide.

Scheme VIII

Certain embodiments are directed to the multistep synthetic method described below, namely Scheme VIII:

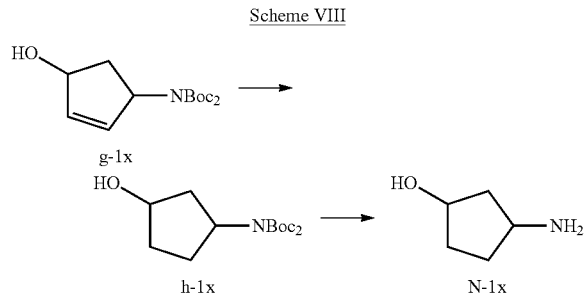

wherein the process comprises the following steps:

reacting g-1x under conditions effective to yield h-1x; and reacting h-1x under conditions effective to yield N-1x.

In some embodiments, the process further comprises the following step:

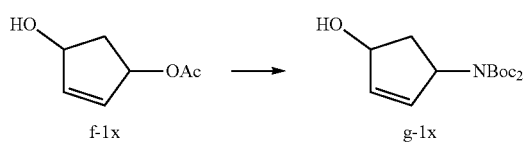

reacting f-1x under conditions effective to yield g-1x.

In some embodiments, g-1x is hydrogenated in the presence of a catalyst and a source of hydrogen to yield h-1x.

In some embodiments, the catalyst is selected form the group consisting of palladium (Pd) based catalysts, PtO₂, Raney Nickel, RhCl(PPh₃)₃, Nyori's catalyst, and Crabtree's catalyst. Exemplary palladium catalyst include Pd/C. In some embodiments, the catalyst is selected form the group consisting of Pd/C, PtO₂, Raney Nickel, RhCl(PPh₃)₃, Nyori's catalyst, and Crabtree's catalyst. In some embodiments, the catalyst is PtO₂.

In certain embodiments, the source of hydrogen is formic acid, hydrazine, dihydronapthalene, dihydroanthracene, H₂ gas or Hantzch ester and isopropanol. In particular embodiments, the source of hydrogen is H₂ gas. In particular embodiments, the source of hydrogen is H₂ gas under an atmosphere of hydrogen.

In some embodiments, h-1x is reacted with an acid to yield N-1x. In some embodiments, the acid is a sulfonic acid, including but not limited to methanesulfonic acid, p-toluenesulfonic acid and camphorsulfonic acid; an inorganic acid, including but not limited to phosphoric acid, hydrochloric acid and sulfuric acid; a carboxylic acid including but not limited to trifluoroacetic acid, oxalic acid and benzoic acid. In certain embodiments, the acid is an inorganic acid. In particular embodiments, the acid is hydrochloric acid. In particular embodiments, the acid is anhydrous hydrochloric acid.

In some embodiments, g-1x is

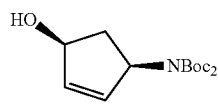

and N-1x is

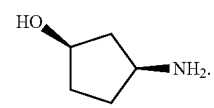

In some embodiments, f-1x is

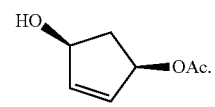

Scheme IX

Certain embodiments are directed to the multistep synthetic method described below, namely General Scheme IX:

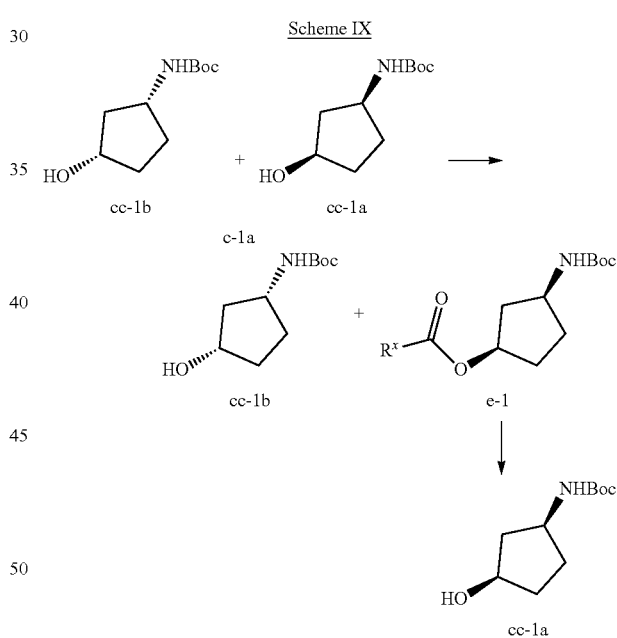

wherein the process comprises the following steps:
reacting racemic c-1a (which is a mixture of cc-1b and cc-1a) with an acyl donor and an enzyme to yield cc-1b and e-1;
isolating e-1 from cc-1b; and
hydrolyzing e-1 to yield enantioenriched cc-1a.

In certain embodiments, $R^x$ is $(C_1-C_6)$alkyl-$R^y$ and $R^y$ is selected from the group consisting of H, CN, —$NR^{z1}R^{z2}$, $C(O)R^{z1}$, —$C(O)OR^{z1}$, —$C(O)NR^{z1}R^{z2}$, —$OC(O)NR^{z1}R^{z2}$, —$NR^{z1}C(O)R^{z2}$, —$NR^{z1}C(O)NR^{z2}$, —$NR^{z1}C(O)OR^{z2}$, —$SR^{z1}$, —$S(O)_{1-2}R^{z1}$, —$S(O)_2NR^{z1}R^{z2}$, —$NR^{z1}S(O)_2R^{z2}$, $NR^{z1}S(O)_2R^{z2}$, and $OR^{z1}$.

In certain embodiments, $R^{z1}$ and $R^{z2}$ are independently selected from the group consisting of H, $C_{1-6}$ alkyl, $C_{2-6}$alkenyl, $C_{2-6}$alkynyl, $C_{1-6}$ heteroalkyl, $C_{3-10}$ cycloalkyl, 3 to 12 membered heterocyclyl, $C_{6-10}$aryl and 5 to 10 membered heteroaryl.

In certain embodiments, $R^x$ is $(C_1-C_6)$alkyl-$R^y$ and $R^y$ is selected from the group consisting of H, —C(O)O$R^{z1}$ and $R^{z1}$ is selected from the group consisting of H, $C_{1-6}$alkyl, $C_{3-10}$ cycloalkyl, and 3 to 12 membered heterocyclyl.

In certain embodiments, $R^x$ is $(C_1-C_6)$alkyl-$R^y$ and $R^y$ is selected from the group consisting of H, —C(O)O$R^{z1}$ and $R^{z1}$ is selected from the group consisting of H and $C_{1-6}$alkyl.

In certain embodiments, $R^x$ is $(C_1-C_4)$alkyl-$R^y$ and $R^y$ is selected from the group consisting of H and $CO_2H$.

In certain embodiments, $R^x$ is methyl or $(CH_2)_3$—$CO_2H$.
In certain embodiments, $R^x$ is $(CH_2)_3$—$CO_2H$.

In certain embodiments, the acyl donor is an anhydride or an ester. In certain embodiments, the anhydride includes but is not limited to glutaric anhydride and acetic anhydride. In certain embodiments, the ester includes but is not limited to vinyl acetate, isopropenyl acetate, 4-chlorophenyl acetate and ethyl methoxy acetate. In particular embodiments, the acyl donor is glutaric anhydride.

In certain embodiments, the enzyme is a lipase. In certain embodiments, the lipase includes but is not limited to Novozyme 435, CAL-A, CAL-B, PPL, PSL-C, PSL, CRL and MML. In certain embodiments, the lipase includes but is not limited to CAL-A, CAL-B, PPL, PSL-C, PSL, CRL and MML. In certain embodiments, the enzyme is CAL-B. In certain embodiments, the enzyme is Novozyme 435.

Novozyme 435 is a CAL-B lipase immobilized on an hydrophobic carrier (acrylin resin).

CAL-B is *Candida antartica* B lipase.
CAL-A is *Candida antartica* A lipase.
PPL is Porcine Pancreas Lipase.
PSL is *Pseudomonas cepacia* lipase.
PSL-C is an immobilized lipase from *Pseudomonas cepacia*.
CRL is *Candida rugosa* lipase.
MML is *Mucor miehei* lipase.

Scheme X

Certain embodiments are directed to the multistep synthetic method described below, namely General Scheme X:

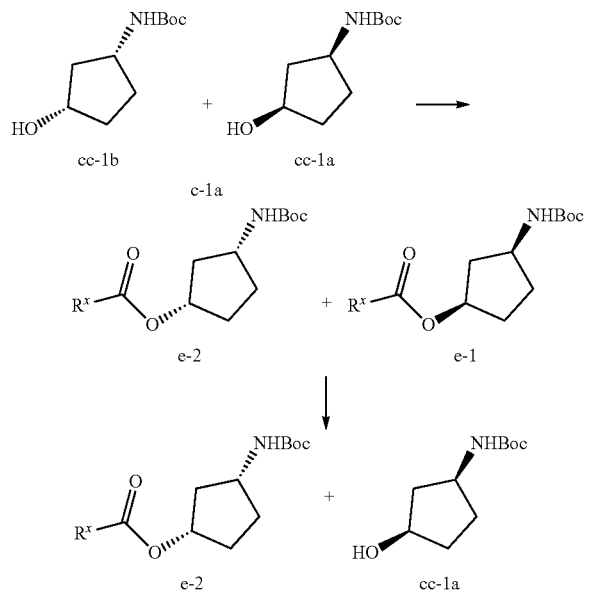

wherein the process comprises the following steps:
reacting racemic c-1a (which is a mixture of cc-1b and cc-1a) with an acyl donor to yield racemic ee-1;
reacting racemic ee-1 (which is a mixture of e-1 and e-2) with an enzyme to yield e-2 and cc-1a; and
isolating enantioenriched cc-1a.

In certain embodiments, $R^x$ is $(C_1-C_6)$alkyl-$R^y$ and $R^y$ is selected from the group consisting of H, CN, —N$R^{z1}R^{z2}$, C(O)$R^{z1}$, —C(O)O$R^{z1}$, —C(O)N$R^{z1}R^{z2}$, —OC(O)N$R^{z1}R^{z2}$, —N$R^{z1}$C(O)$R^{z2}$, —N$R^{z1}$C(O)N$R^{z2}$, —N$R^{z1}$C(O)O$R^{z2}$, —S$R^{z1}$, —S(O)$_{1-2}R^{z1}$, —S(O)$_2$N$R^{z1}R^{z2}$, —N$R^{z1}$S(O)$_2R^{z2}$, N$R^{z1}$S(O)$_2R^{z2}$, and O$R^{z1}$.

In certain embodiments, each $R^{z1}$ and $R^{z2}$ is independently selected from the group consisting of H, $C_{1-6}$alkyl, $C_{2-6}$alkenyl, $C_{2-6}$alkynyl, $C_{1-6}$heteroalkyl, $C_{3-10}$cycloalkyl, 3 to 12 membered heterocyclyl, $C_{6-10}$aryl and 5 to 10 membered heteroaryl.

In certain embodiments, $R^x$ is $(C_1-C_6)$alkyl-$R^y$ and $R^y$ is selected from the group consisting of H, —C(O)O$R^{z1}$ and $R^{z1}$ is selected from the group consisting of H, $C_{1-6}$ alkyl, $C_{3-10}$cycloalkyl, and 3 to 12 membered heterocyclyl.

In certain embodiments, $R^x$ is $(C_1-C_6)$alkyl-$R^y$ and $R^y$ is selected from the group consisting of H, —C(O)O$R^{z1}$ and $R^{z1}$ is selected from the group consisting of H and $C_{1-6}$alkyl.

In certain embodiments, is $(C_1-C_4)$alkyl-$R^y$ and $R^y$ is selected from the group consisting of H and $CO_2H$.

In certain embodiments, $R^x$ is methyl or $(CH_2)_3$—$CO_2H$.
In certain embodiments, $R^x$ is $(CH_2)_3$—$CO_2H$.

In certain embodiments, the acyl donor includes but is not limited to an anhydride or an acid chloride. In certain embodiments, the anhydride includes but is not limited to succinic anhydride and acetic anhydride. In certain embodiments, the acid chloride include but is not limited to acetyl chloride and benzoyl chloride. In particular embodiments, the acyl donor is Glutaric anhydride.

In certain embodiments, the enzyme is a lipase such as but are not limited to CAL-A, CAL-B, PPL, PSL-C, PSL, CRL, and MML. In particular embodiments, the enzyme is CAL-B.

Scheme XI

Certain embodiments are directed to the multistep synthetic method described below, namely Scheme XI:

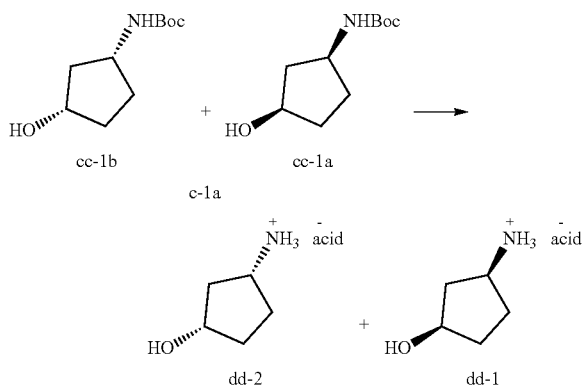

wherein the process comprises the following steps:
reacting racemic c-1a (which is a mixture of cc-1b and cc-1a) with a chiral acid to yield dd-1 and dd-2; and
isolating enantioenriched dd-1.

In certain embodiments, the chiral acid is selected from the group consisting of:
- single enantiomers of carboxylic acids including but not limited to: naproxen, phenyl succinic acid, malic acid, 2-phenylpropionic acid, alpha-methoxyphenyl acetic acid, tartranilic acid, 3-phenyllactic acid, α-hydroxyisovaleric acid, 2'-methoxy-tartranilic acid, (alpha-methylbenzyl)phthalamic acid, 2'-chloro-tartranilic acid, pyroglutamic acid;
- single enantiomers of mandelic acid derivatives including but not limited to: mandelic acid, 2-chloromandelic acid, 4-bromo-mandelic acid, O-acetyl mandelic acid, 4-methyl-mandelic acid;
- single enantiomers of sulfonic acids including but not limited to: camphor sulfonic acid;
- single enantiomers of tartaric acid derivatives including but not limited to: tartaric acid, dibenzoyl tartaric acid hydrate, di-p-anisoyltartaric acid, di-toluyltartaric acid, dibenzoyl tartaric acid hydrate;
- single enantiomers of phosphoric acid derivatives including but not limited to: phencyphos hydrate, chlocyphos, anisyphos, BINAP phosphate; and
- single enantiomers of amino acids including but not limited tos: N-acetyl-phenylalanine, N-acetyl-leucine, N-acetyl-proline, boc-phenylalanine, and boc-homophenylalanine.

In certain embodiments, the chiral acid is a single enantiomers of a carboxylic acid.

In particular embodiments, the acid is (R)-Naproxen. In particular embodiments, the acid is R-(+)-mandelic acid.

In particular embodiments, the acid is (S)-Naproxen. In particular embodiments, the acid is S-(+)-mandelic acid.

In certain embodiments, the reaction with the chiral acid occurs in a solvent selected from the group consisting of water, acetonitrile, ethanol, isopropanol, methyl ethyl ketone, isopropyl acetate, dioxane, a mixture of water and a water-miscible organic solvents such as ethanol and isopropanol, an halogenated solvent such as dichloromethane and chloroform. In particular embodiments, the solvent is water or isopropanol or a mixture thereof. In particular embodiments, the solvent is water. In particular embodiments, the solvent is isopropanol.

In certain embodiments, the reaction with the chiral acid is stirred at 0 to 120° C., 20 to 120° C., 50 to 120° C., 80 to 120° C., or about 100° C. In certain embodiments, the reaction is stirred at about 20° C.

In certain embodiments, isolating dd-1 comprises selectively recrystallizing dd-1. In certain embodiments, the recrystallization occurs in water, acetonitrile, ethanol, isopropanol, methyl ethyl ketone, isopropyl acetate, dioxane; a mixture of water and water-miscible organic solvents such as ethanol and isopropanol, or a halogenated solvent such as dichloromethane or chloroform. In certain embodiments, the recrystallization occurs in a mixture of methyl ethyl ketone and water.

In certain embodiments, dd-1 precipitates out of solution and is filtered.

Schemes VII-XI disclose steps and intermediates which are useful for the the preparation of N-1 and/or a compound of Formula I.

General Schemes—Individual Steps

Additional embodiments are directed to the individual steps of the multistep general synthetic methods described above, namely General Schemes I-V and VI to XI. These individual steps and intermediates of the present invention are described in detail below. All substituent groups in the steps described below are as defined in the multi-step method above.

A. Acylation and Amidation of Meldrum's Acid to Provide C-1:

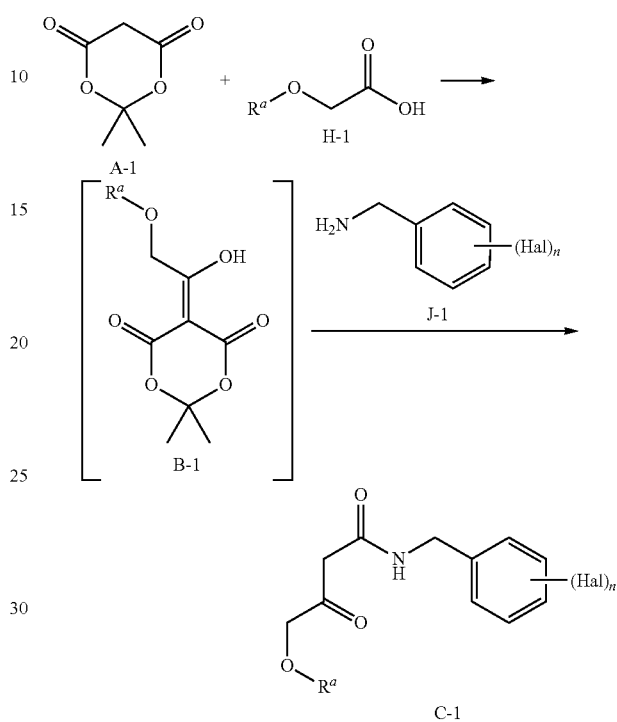

1. Conversion of A-1 to B-1

In particular embodiments, one equivalent of Meldrum's acid (A-1) and a suitable catalyst are suspended in a suitable solvent, and the resulting solution is treated with about 1.2 equivalents of H-1. About 2 equivalents of a suitable base are slowly added to the resulting solution, followed by the addition of about 1.1 equivalents of a suitable acylating reagent. The reaction occurs at about 20 to 80° C. and is allowed to continue until consumption of Meldrum's acid is complete, as monitored by any suitable method known in the art.

In certain embodiments, the catalyst is a nucleophilic amine-containing compound, such as, but is not limited to, 4-dimethylaminopyridine, imidazole, 1,4-diazabicyclo[2.2.2]octane, 1,8-diazabicyclo[5.4.0]undec-7-ene, or pyridine. In further embodiments, the catalyst is a nucleophilic phosphine containing compound, such as, but not limited to, triphenylphosphine. In a particular embodiment, the catalyst is 4-dimethylaminopyridine.

In certain embodiments, the solvent for the above reaction is a polar non-protic solvent or an aromatic solvent. In certain embodiments, the solvent for the above reaction is a polar non-protic solvent. In certain embodiments, the solvent for the above reaction is an aromatic solvent. Exemplary polar non-protic solvents include, but are not limited to, acetonitrile, N,N-dimethylformamide, N,N-dimethylacetamide, 1,4-dioxane, or N-methyl-2-pyrrolidinone. Exemplary aromatic solvents for the above reaction include, but not limited to, pyridine, toluene, xylene, benzene, or chlorobenzene. In still further embodiments, the solvent is a mixture comprising at least one of the forgoing solvents. For example, in certain embodiments, the solvent is a mixture of up to three, or up to two, polar non-protic solvents selected from the group consisting of acetonitrile, N,N-dimethylformamide, N,N-dimethylacetamide, 1,4-dioxane, and N-methyl-2-pyrrolidinone. In other embodiments, the solvent is a mixture of up to three, or up to two, aromatic solvents selected from the group consisting of pyridine, toluene, xylene, benzene, and chlorobenzene. In one embodiment the solvent is a mixture of up to three, or up to two, solvents selected from the group consisting of acetonitrile, N,N-dimethylformamide, N,N-dimethylacetamide, 1,4-dioxane, N-methyl-2-pyrrolidinone, pyridine, toluene, xylene, benzene, and chlorobenzene. In a further embodiment, the solvent is acetonitrile.

In certain embodiments, $R^a$ is $(C_1-C_4)$alkyl, $(C_2-C_{10})$aryl, or $(C_2-C_{10})$aryl $(C_1-C_4)$alkyl. In certain embodiments, $R^a$ is $(C_1-C_4)$alkyl, $(C_6-C_{10})$aryl, or $(C_6-C_{10})$aryl $(C_1-C_4)$alkyl. In certain embodiments, $R^a$ is $(C_1-C_4)$alkyl. In certain embodiments $R^a$ is —$CH_3$, that is H-1 is methoxyacetic acid.

In certain embodiments, the base is an amine base, an aromatic base, inorganic carbonate, a metal hydride, an alkoxide, or mixtures thereof. In certain embodiments, the base is an amine base. In certain embodiments, the base is an aromatic base. In certain embodiments, the base is an inorganic carbonate. In certain embodiments, the base is a metal hydride. In certain embodiments, the base is an alkoxide. Exemplary amine bases include, but are not limited to, triethylamine, N,N-diisopropylethylamine, quinuclidine, 1,4-diazabicyclo[2.2.2]octane, 1,8-diazabicyclo[5.4.0]undec-7-ene, tripropylamine, and tributylamine. Exemplary aromatic amine bases include, but are not limited to, pyridine. Exemplary inorganic carbonates include, but are not limited to, lithium carbonate, sodium carbonate, potassium carbonate, or cesium carbonate. Exemplary metal hydrides, include, but are not limited to, sodium hydride or potassium hydride. Exemplary alkoxides include, but are not limited to, sodium methoxide, sodium tert-butoxide or lithium tert-butoxide. In still further embodiments, the base is a mixture comprising at least one of the preceding bases. For example, in certain embodiments, the base is a mixture of up to three, or up to two, amine bases. In certain embodiments, the base is a mixture of up to three, or up to two, aromatic bases. In certain embodiments, the base is a mixture of up to three, or up to two, inorganic carbonates. In certain embodiments, the base is a mixture of up to three, or up to two, metal hydrides. In certain embodiments, the base is a mixture of up to three, or up to two, alkoxides. In certain embodiments, the base is a mixture of up to three, or up to two, bases from the group consisting of triethylamine, N,N-diisopropylethylamine, quinuclidine, 1,4-diazabicyclo[2.2.2]octane, 1,8-diazabicyclo[5.4.0]undec-7-ene, tripropylamine, tributylamine, pyridine, lithium carbonate, sodium carbonate, potassium carbonate, cesium carbonate, sodium hydride, potassium hydride, sodium methoxide, sodium tert-butoxide and lithium tert-butoxide. In a particular embodiment, the base is triethylamine.

In certain embodiments, the acylating reagent is a carboxylic acid activating reagent, a carbodiimide derivative, or a mixture thereof. In certain embodiments, the acylating reagent is a carboxylic acid activating reagent. In certain embodiments, the acylating reagent is a carbodiimide derivative. In certain embodiments, the acylating reagent is a mixture of a carboxylic acid activating reagent and a carbodiimide derivative. Exemplary carboxylic acid activating reagents include, without limitation, pivaloyl chloride, carbonyldiimidazole, thionyl chloride, and oxalyl chloride. Exemplary carbodiimide derivatives include, without limitation, carbonyldiimidazole and N,N'-dicyclohexylcarbodiimide. In certain embodiments, the acylating reagent is pivaloyl chloride, carbonyldiimidazole, thionyl chloride, oxalyl chloride, or N,N'-dicyclohexylcarbodiimide. In certain embodiments, the acylating reagent is a mixture of up to three, or up to two, reagents from the groups consisting of pivaloyl chloride, carbonyldiimidazole, thionyl chloride, oxalyl chloride, or N,N'-dicyclohexylcarbodiimide. In certain embodiments, the acylating reagent is pivaloyl chloride.

In certain embodiments, the reaction occurs at about 20 to 70° C., about 20 to 60° C., about 20 to 50° C., about 20 to 40° C., about 20 to 30° C., about 30 to 80° C., about 30 to 70° C., about 30 to 60° C., about 30 to 50° C., about 30 to 40° C., about 40 to 80° C., about 40 to 70° C., about 40 to 60° C., about 40 to 50° C., about 50 to 80° C., about 50 to 70° C., about 50 to 60° C., about 60 to 80° C., about 60 to 70° C., about 70 to 80° C., or any subrange therebetween. In particular embodiments, the reaction occurs at about 35 to 40° C., about 40 to 45° C., about 45 to 50° C., or any subrange therebetween.

In particular embodiments, the catalyst is 4-dimethylaminopyridine, the solvent is acetonitrile, $R^a$ is —$CH_3$, the base is triethylamine, the acylating reagent is pivaloyl chloride and the reaction occurs at about 45 to 50° C.

2. Conversion of B-1 to C-1

In a separate vessel, about 1.2 equivalents of J-1 is suspended in a suitable solvent. The resulting solution is treated with about 1.5 equivalents of a suitable acid, and then this acidic solution is added to the above acylation reaction in progress. The reaction is allowed to continue for about 12 to about 24 hours at about 20 to 80° C., after which time the solvent is removed and C-1 is recovered and purified from the residue using any suitable technique known in the art, such as, but not limited to solvent extraction, silica gel chromatography and crystallization.

In certain embodiments, J-1 is suspended in a polar non-protic solvent or an aromatic solvent. In certain embodiments, J-1 is suspended in a polar non-protic solvent. In certain embodiments, J-1 is suspended in an aromatic solvent. Exemplary polar non-protic solvent include, but are not limited to, acetonitrile, N,N-dimethylformamide, N,N-dimethylacetamide, 1,4-dioxane, and N-methyl-2-pyrrolidinone. Exemplary aromatic solvents include, but are not limited to, pyridine, toluene, xylene, benzene, and chlorobenzene. In still further embodiments, J-1 is suspended in a solvent mixture comprising one or more polar non-protic solvents and/or one or more aromatic solvents. In certain embodiments, J-1 is suspended in a solvent mixture comprising up to three, or up to two, polar non-protic solvents. In certain embodiments, J-1 is suspended in a solvent mixture comprising up to three, or up to two, aromatic solvents. In certain embodiments, J-1 is suspended in a solvent mixture comprising up to three, or up to two, solvents from the group consisting of acetonitrile, N,N-dimethylformamide, N,N-dimethylacetamide, 1,4-dioxane, N-methyl-2-pyrrolidinone, pyridine, toluene, xylene, benzene, and chlorobenzene. In a further embodiment, J-1 is suspended in acetonitrile.

In particular embodiments, the acid is an inorganic acid, an organic acid, or a halogenated organic acid. In certain embodiments, the acid is an inorganic acid. In certain embodiments, the acid is an organic acid. Exemplary inorganic acids, include, but are not limited to hydrochloric acid, hydrobromic acid, and hydroiodic acid. Exemplary organic acids, include, but are not limited to, formic acid and acetic acid. In yet other embodiments the organic acid is a halogenated organic acid. Exemplary halogenated organic acids include, but are not limited to, trifluoromethanesulfonic acid, trifluoroacetic acid, trichloroacetic acid, and perfluoropropionic acid. In still further embodiments, the acid is a mixture comprising one or more organic acids and one or more inorganic acids. In certain embodiments, the acid is a mixture comprising up to three, or up to two, organic acids. In certain embodiments, the acid is a mixture comprising up to three, or up to two, halogenated organic acids. In certain embodiments, the acid is a mixture comprising up to three, or up to two, inorganic acids. In a certain embodiment, the acid is a mixture of up to three, or up to two, acids selected from the group consisting of hydrochloric acid, hydrobromic acid, hydroiodic acid, formic acid, trifluoromethanesulfonic acid, trifluoroacetic acid, trichloroacetic acid, and perfluoropropionic acid. In a particular embodiment, the acid is trifluoroacetic acid.

In particular embodiments, each Hal is independently —F or —Cl. In a particular embodiment, Hal is —F In certain embodiments, n=1-3. In certain embodiments, n=2. In certain embodiments, n=3. In further embodiments, J-1 is

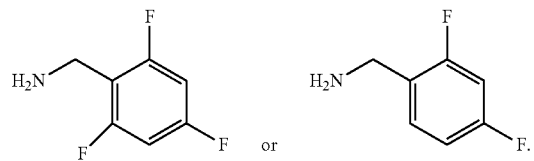 [SMILES: NCc1c(F)cc(F)cc1F ; NCc1ccc(F)cc1F]

In certain embodiments, J-1 is

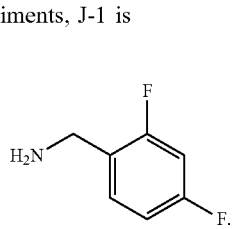

In further embodiments, J-1 is

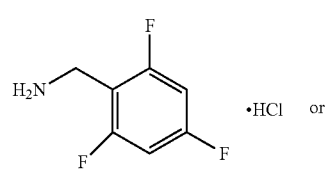

In still further embodiments, J-1 is in the form of a salt or co-crystal, such as, but not limited to a salt or co-crystal of hydrochloric acid or trifluoroacetic acid. In certain embodiments, J-1 is a salt or co-crystal of methane sulfonic acid.

For example, in certain embodiments, J-1 is:

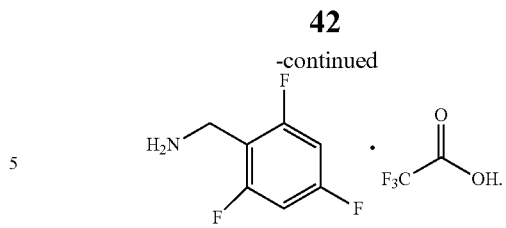

In a particular embodiment, J-1 is

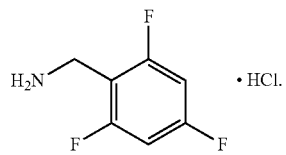 [SMILES: NCc1c(F)cc(F)cc1F]

In a particular embodiment, J-1 is

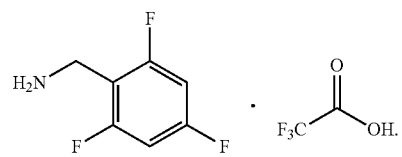 [SMILES: NCc1c(F)cc(F)cc1F ; O=C(O)C(F)(F)F]

For example, in certain embodiments, J-1 is:

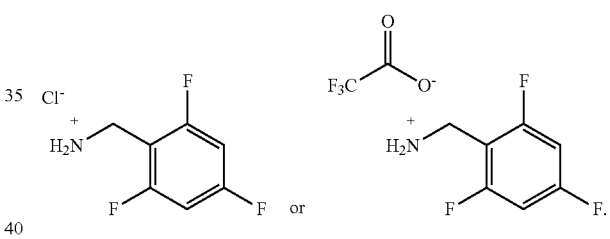

In a particular embodiment, J-1 is

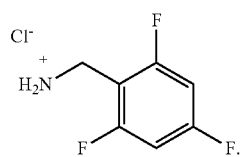 [SMILES: [Cl-] ; NCc1c(F)cc(F)cc1F]

In a particular embodiment, J-1 is

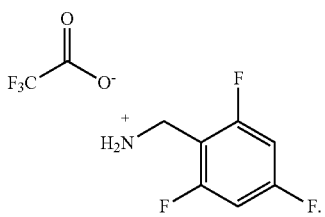 [SMILES: O=C([O-])C(F)(F)F ; NCc1c(F)cc(F)cc1F]

In certain embodiments, the reaction occurs at about 20 to 70° C., about 20 to 60° C., about 20 to 50° C., about 20 to 40° C., about 20 to 30° C., about 30 to 80° C., about 30 to 70° C., about 30 to 60° C., about 30 to 50° C., about 30 to 40° C., about 40 to 80° C., about 40 to 70° C., about 40 to 60° C., about 40 to 50° C., about 50 to 80° C., about 50 to 70° C., about 50 to 60° C., about 60 to 80° C., about 60 to 70° C., about 70 to 80° C., or any subrange therebetween. In particular embodiments, the reaction occurs at about 35 to 40° C., about 40 to 45° C., about 45 to 50° C., or any subrange therebetween.

In certain embodiments, the solvent is removed under reduced pressure. In particular embodiments, C-1 is extracted from the crude residue by solvent extraction. In a particular embodiment, the crude residue is dissolved in an organic solvent, such as ethyl acetate, and the organic layer is washed with water. The combined aqueous layers are extracted with an organic solvent, such as ethyl acetate. The combined organic layers are washed with saturated sodium bicarbonate solution, and the combined bicarbonate washes are back extracted with an organic solvent such as ethyl acetate. Total combined organic layers are dried over a drying agent, such as magnesium sulfate, filtered, and concentrated under reduced pressure. The resulting crude material is purified using any suitable technique, such as silica gel chromatography to yield C-1.

In particular embodiments, J-1 is suspended in acetonitrile, the acid is trifluoroacetic acid, J-1 is

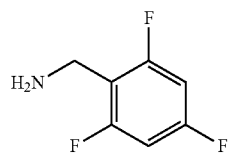 [SMILES: NCc1c(F)cc(F)cc1F]

and the reaction occurs at about 45 to 50° C.

3. Formation of C-1 Through B-1.J-1 Salt

Alternatively, in certain embodiments, C-1 is formed via formation of a B-1.J-1 salt following the procedure below.

a. Formation of B-1.J-1 Salt by Addition of J-1 to B-1

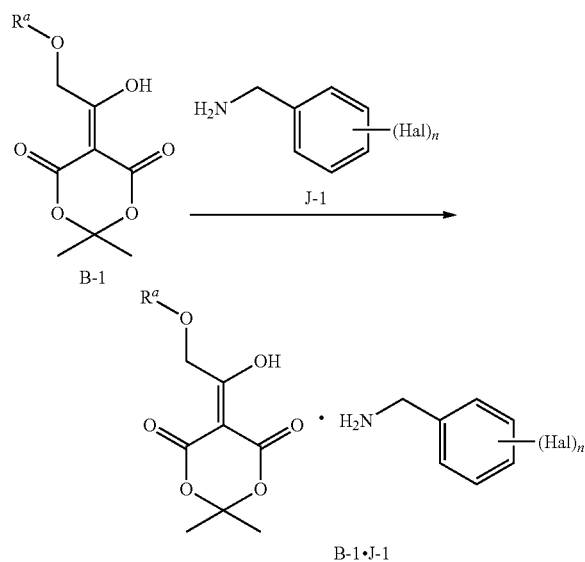

B-1·J-1

The free acid of B-1 (about 1 equivalent) is dissolved in a solvent, followed by addition of J-1 (about 1 to about 5 equivalents). In certain embodiments, the salt is aged for up to 12 hours, up to 10 hours, up to 8 hours, up to 6 hours, up to 4 hours, or up to 3 hours. The salt is obtained by any suitable methods known in the art, including but not limited to solvent filtration, extraction, crystallization, and silica gel chromatography.

In certain embodiments, the solvent for the above reaction is a polar non-protic solvent or an aromatic solvent. In certain embodiments, the solvent for the above reaction is a polar non-protic solvent. In certain embodiments, the solvent for the above reaction is an aromatic solvent. Exemplary polar non-protic solvents include, but are not limited to, acetonitrile, N,N-dimethylformamide, N,N-dimethylacetamide, 1,4-dioxane, or N-methyl-2-pyrrolidinone. Exemplary aromatic solvents for the above reaction include, but not limited to, pyridine, toluene, xylene, benzene, or chlorobenzene. In still further embodiments, the solvent is a mixture comprising at least one of the forgoing solvents. For example, in certain embodiments, the solvent is a mixture of up to three, or up to two, polar non-protic solvents selected from the group consisting of acetonitrile, N,N-dimethylformamide, N,N-dimethylacetamide, 1,4-dioxane, and N-methyl-2-pyrrolidinone. In other embodiments, the solvent is a mixture of up to three, or up to two, aromatic solvents selected from the group consisting of pyridine, toluene, xylene, benzene, and chlorobenzene. In one embodiment the solvent is a mixture of up to three, or up to two, solvents selected from the group consisting of acetonitrile, N,N-dimethylformamide, N,N-dimethylacetamide, 1,4-dioxane, N-methyl-2-pyrrolidinone, pyridine, toluene, xylene, benzene, and chlorobenzene. In a further embodiment, the solvent is acetonitrile.

In some embodiments, B-1.J-1 is:

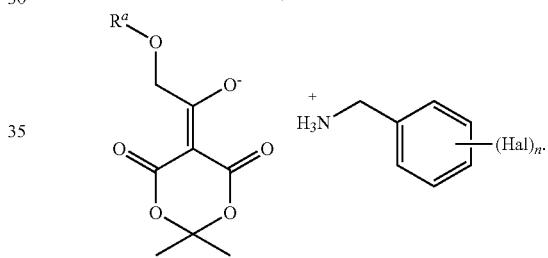

In certain embodiments, the reaction is stirred to about 15 to 30° C., about 20 to 70° C., about 20 to 60° C., about 20 to 50° C., about 20 to 40° C., about 20 to 30° C., about 30 to 80° C., about 30 to 70° C., about 30 to 60° C., about 30 to 50° C., about 30 to 40° C., about 40 to 80° C., about 40 to 70° C., about 40 to 60° C., about 40 to 50° C., about 50 to 80° C., about 50 to 70° C., about 50 to 60° C., about 60 to 80° C., about 60 to 70° C., about 70 to 80° C., or any subrange therebetween. In further embodiments, the reaction proceeds at about 15 to about 25° C.

In certain embodiments, the solvent is acetonitrile and the reaction proceeds at about 18 to about 25° C.

b. Formation of C-1 from salt B-1.J-1

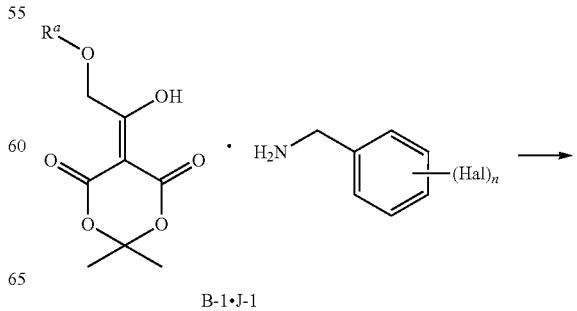

B-1·J-1

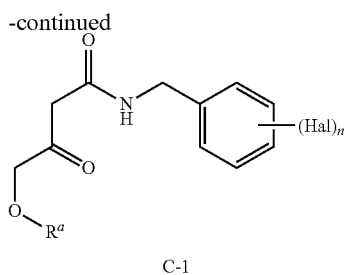

The salt B-1.J-1 (about 1 equivalent) is suspended in a suitable solvent. The resulting solution is treated with about 0.1 to 1 equivalents of a suitable acid. The reaction is allowed to continue for about 12 to about 24 hours at about 20 to 80° C., after which time the solvent is removed and C-1 is recovered and purified from the residue using any suitable technique known in the art, such as, but not limited to solvent extraction, silica gel chromatography, crystallization, and filtration.

In certain embodiments, the solvent for the above reaction is a polar non-protic solvent or an aromatic solvent. In certain embodiments, the solvent for the above reaction is a polar non-protic solvent. In certain embodiments, the solvent for the above reaction is an aromatic solvent. Exemplary polar non-protic solvents include, but are not limited to, acetonitrile, N,N-dimethylformamide, N,N-dimethylacetamide, 1,4-dioxane, or N-methyl-2-pyrrolidinone. Exemplary aromatic solvents for the above reaction include, but not limited to, pyridine, toluene, xylene, benzene, or chlorobenzene. In still further embodiments, the solvent is a mixture comprising at least one of the forgoing solvents. For example, in certain embodiments, the solvent is a mixture of up to three, or up to two, polar non-protic solvents selected from the group consisting of acetonitrile, N,N-dimethylformamide, N,N-dimethylacetamide, 1,4-dioxane, and N-methyl-2-pyrrolidinone. In other embodiments, the solvent is a mixture of up to three, or up to two, aromatic solvents selected from the group consisting of pyridine, toluene, xylene, benzene, and chlorobenzene. In one embodiment the solvent is a mixture of up to three, or up to two, solvents selected from the group consisting of acetonitrile, N,N-dimethylformamide, N,N-dimethylacetamide, 1,4-dioxane, N-methyl-2-pyrrolidinone, pyridine, toluene, xylene, benzene, and chlorobenzene. In a further embodiment, the solvent is acetonitrile.

In particular embodiments, the acid is an inorganic acid, an organic acid, or a halogenated organic acid. In certain embodiments, the acid is an inorganic acid. In certain embodiments, the acid is an organic acid. Exemplary inorganic acids, include, but are not limited to hydrochloric acid, hydrobromic acid, hydroiodic acid. Exemplary organic acids, include, but are not limited to, formic acid and acetic acid. In yet other embodiments the organic acid is a halogenated organic acid. Exemplary halogenated organic acids include, but are not limited to, trifluoromethanesulfonic acid, trifluoroacetic acid, trichloroacetic acid, and perfluoropropionic acid. In certain embodiments, the acid is trifluoroacetic acid. In still further embodiments, the acid is a mixture comprising one or more organic acids and one or more inorganic acids. In certain embodiments, the acid is a mixture comprising up to three, or up to two, organic acids. In certain embodiments, the acid is a mixture comprising up to three, or up to two, halogenated organic acids. In certain embodiments, the acid is a mixture comprising up to three, or up to two, inorganic acids. In a certain embodiment, the acid is a mixture of up to three, or up to two, acids selected from the group consisting of hydrochloric acid, hydrobromic acid, hydroiodic acid, formic acid, trifluoromethanesulfonic acid, trifluoroacetic acid, trichloroacetic acid, and perfluoropropionic acid. In a particular embodiment, the acid is trifluoroacetic acid.

In certain embodiments, after the addition is complete the reaction is heated to about 20 to 70° C., about 20 to 60° C., about 20 to 50° C., about 20 to 40° C., about 20 to 30° C., about 30 to 80° C., about 30 to 70° C., about 30 to 60° C., about 30 to 50° C., about 30 to 40° C., about 40 to 80° C., about 40 to 70° C., about 40 to 60° C., about 40 to 50° C., about 50 to 80° C., about 50 to 70° C., about 50 to 60° C., about 60 to 80° C., about 60 to 70° C., about 70 to 80° C., or any subrange therebetween. In further embodiments, the reaction proceeds at about 60° C.

In particular embodiments, the solvent is acetonitrile, the acid is trifluoroacetic acid and the reaction proceeds at about 60° C.

B. Alkylation of C-1 to Form E-1:

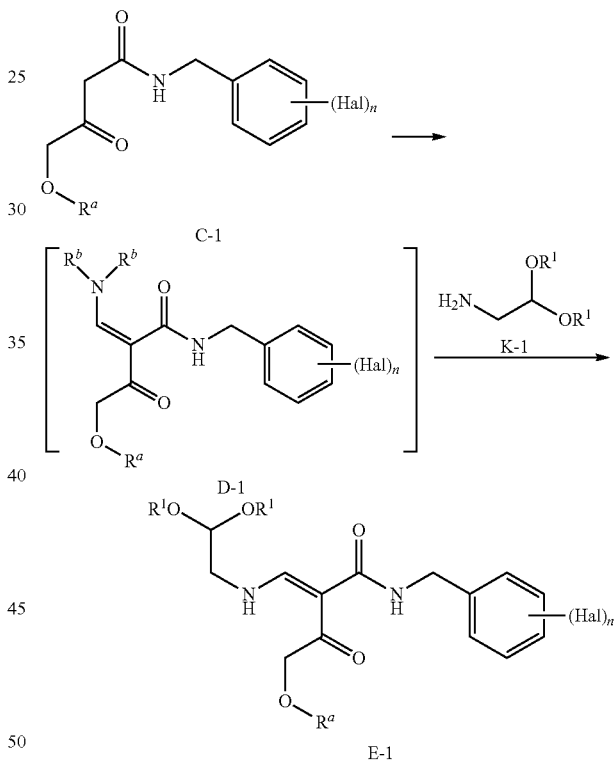

A solution of about one equivalent of C-1 in a suitable solvent is treated with about one to one and a half equivalents of an alkylated formamide acetal and is stirred at about 0 to 60° C. for about 10 hours to about 18 hours. The reaction is treated with about one equivalent of K-1, and is allowed to continue for about one to about four hours, and is then quenched via the addition of an acid. E-1 is then extracted and purified by any suitable methods known in the art, including but not limited to solvent extraction, crystallization, and silica gel chromatography.

In a particular embodiment, the solvent is a non-protic polar organic solvent such as, but not limited to, 2-methyl tetrahydrofuran, tetrahydrofuran, acetonitrile, diisopropyl ether, methyl tert-butyl ether, N,N-dimethylformamide, N,N-dimethylacetamide, 1,4-dioxane, N-methyl-2-pyrrolidinone, or mixtures thereof. In a further embodiment, the solvent is 2-methyl tetrahydrofuran.

In certain embodiments, the alkylated formamide acetal is selected from the group consisting of N,N-dimethylformamide dimethyl acetal, N,N-dimethylformamide diethyl acetal, N,N-dimethylformamide diisopropyl acetal, N,N-diethylformamide dimethyl acetal, and N,N-diisopropylformamide dimethyl acetal. In a particular embodiment, the alkylated formamide acetal is N,N-dimethylformamide dimethyl acetal.

In particular embodiments, one equivalent of C-1 is treated with about 1.1 equivalents of the alkylated formamide acetal.

In certain embodiments, $R^1$ is $(C_1-C_4)$alkyl, $(C_2-C_{10})$aryl, or $(C_2-C_{10})$aryl $(C_1-C_4)$alkyl. In certain embodiments, $R^1$ is $(C_1-C_4)$alkyl, $(C_6-C_{10})$aryl, or $(C_6-C_{10})$aryl $(C_1-C_4)$alkyl. In certain embodiments, $R^1$ is $C_1-C_4$alkyl. In further embodiments $R^1$ is —$CH_3$, that is, K-1 is aminoacetaldehyde dimethyl acetal.

In certain embodiments, the reaction is quenched with an inorganic acid, an organic acid, or a halogenated organic acid. In certain embodiments, the acid is an inorganic acid. In certain embodiments, the acid is an organic acid. In certain embodiments, the acid is a halogenated organic acid. Exemplary inorganic acids, include, but are not limited to hydrochloric acid, hydrobromic acid, hydroiodic acid. Exemplary organic acids, include, but are not limited to, formic acid and acetic acid. Exemplary halogenated organic acids include, but are not limited to, trifluoromethanesulfonic acid, trifluoroacetic acid, trichloroacetic acid, and perfluoropropionic acid. In still further embodiments, the acid is a mixture comprising one or more organic acids, one or more inorganic acids, and/or one or more halogenated organic acids. In certain embodiments, the acid is a mixture comprising up to three, or up to two, organic acids. In certain embodiments, the acid is a mixture comprising up to three, or up to two, halogenated organic acids. In certain embodiments, the acid is a mixture comprising up to three, or up to two, inorganic acids. In a certain embodiment, the acid is a mixture of up to three, or up to two, acids selected from the group consisting of hydrochloric acid, hydrobromic acid, hydroiodic acid, formic acid, trifluoromethanesulfonic acid, trifluoroacetic acid, trichloroacetic acid, and perfluoropropionic acid. In a particular embodiment, the acid is trifluoroacetic acid. In particular embodiments, the reaction is quenched with hydrochloric acid. In particular embodiments, the reaction is quenched with 2 N HCl. In certain embodiments, the reaction is not quenched.

In certain embodiments, the reaction proceeds at about 10 to 60° C., about 10 to 50° C., about 10 to 40° C., about 10 to 30° C., about 10 to 20° C., 20 to 60° C., about 20 to 50° C., about 20 to 40° C., about 20 to 30° C., about 30 to 60° C., about 30 to 50° C., about 30 to 40° C., about 40 to 60° C., about 40 to 50° C., about 50 to 60° C., or any subrange therebetween. In particular embodiments, the reaction proceeds at room temperature. In further embodiments, the reaction proceeds at about 15 to about 25° C.

In particular embodiments, the solvent is 2-methyl tetrahydrofuran, the alkylated formamide acetal is N,N-dimethylformamide dimethyl acetal, $R^1$ is —$CH_3$, and the reaction proceeds at about 18 to about 23° C.

C. Cyclization of E-1 to Form F-1:

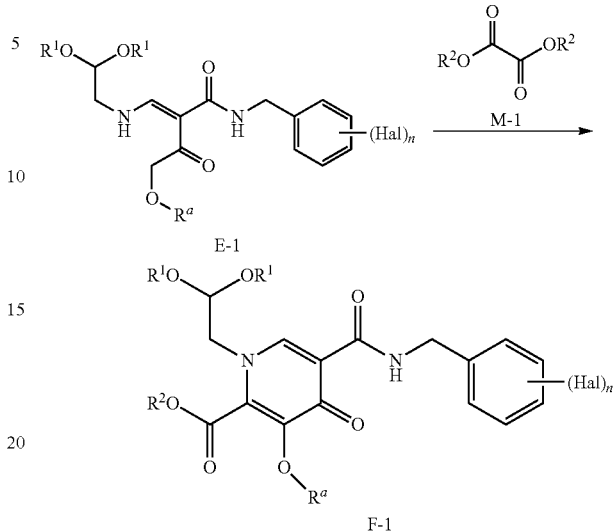

In particular embodiments, a solution of about one equivalent of E-1 and about one to five equivalents of M-1 in a first suitable solvent is combined and cooled to about 0 to 5° C. In certain embodiments, the base is slowly introduced to the reaction mixture while the internal temperature of the reaction is kept cool throughout the addition (e.g., below room temperature, or below about 25° C., or below about 20° C., or below about 15° C.). After the addition is complete the reaction is heated to about 20 to 80° C. for at least about 14 hours.

After this time has elapsed, the reaction may be diluted with an aqueous acidic solution and a further suitable organic solvent and the product extracted and purified by any suitable methods known in the art, including but not limited to solvent extraction, crystallization, and silica gel chromatography. In certain embodiments, the aqueous acidic solution is hydrochloric acid and acetic acid. For example, in certain embodiments, the aqueous acidic solution is glacial acetic acid.

In particular embodiments, the first solvent is one or more alcohols, one or more polar organic solvents, or a mixture of or more alcohols and one or more polar organic solvents. In certain embodiments, the first solvent is up to three alcohols, up to three polar organic solvents, or a mixture thereof (i.e., a mixture of up to three, or up to two, alcohols and up to three, or up to two, polar organic solvents). In certain embodiments, the first solvent is one or two alcohols, one or two polar organic solvents, or a mixture thereof (i.e., a mixture of one or two alcohols and one or two polar organic solvents). In certain embodiments, the first solvent is an alcohol. In certain embodiments, the first solvent is a polar organic solvent. Exemplary alcohols include, but are not limited to, methanol, ethanol, n-propanol, 2-propanol, butanol, and tert-butanol. Exemplary polar organic solvents include, but are not limited to, acetone, acetonitrile, N,N-dimethylformamide, N,N-dimethylacetamide, 1,4-dioxane, and N-methyl-2-pyrrolidinone. In certain embodiments, the first solvent is methanol, ethanol, n-propanol, 2-propanol, butanol, tert-butanol acetone, acetonitrile, N,N-dimethylformamide, N,N-dimethylacetamide, 1,4-dioxane, or N-methyl-2-pyrrolidinone. In a certain embodiment, the first solvent is methanol.

In particular embodiments, the base is a metal hydride, an alkoxide, or a bis(trialkylsilyl) amide. In certain embodiments, the base is a metal hydride. In certain embodiments, the base is an alkoxide. In certain embodiments, the base is a bis(trialkylsilyl) amide. Exemplary metal hydrides include, but are not limited to lithium hydride, sodium hydride, and potassium hydride. Exemplary alkoxides include, but are not limited to, sodium methoxide, sodium tert-butoxide, sodium ethoxide, potassium tert-butoxide, potassium ethoxide, sodium tert-pentoxide, and lithium tert-butoxide. Exemplary bis(trialkylsilyl) amide bases include, but are not limited to lithium bis(trimethylsilyl)amide, sodium bis(trimethylsilyl)amide, and potassium bis(trimethylsilyl)amide. In still further embodiments, the base is a mixture of at least one of the foregoing bases. In certain embodiments, the base is a mixture of up to three, or up to two, metal hydrides. In certain embodiments, the base is a mixture of up to three, or up to two, alkoxides. In certain embodiments, the base is a mixture of up to three, or up to two, metal bis(trialkylsilyl) amides. In certain embodiments, the base is a mixture of up to three, or up to two, of the following bases: lithium hydride, sodium hydride, potassium hydride, sodium methoxide, sodium tert-butoxide, sodium ethoxide, potassium tert-butoxide, potassium ethoxide, sodium tert-pentoxide, lithium tert-butoxide, lithium bis(trimethylsilyl)amide, sodium bis(trimethylsilyl)amide, or potassium bis(trimethylsilyl)amide. In particular embodiments, the base is sodium methoxide.

In certain embodiments, $R^2$ is $(C_1-C_4)$alkyl, $(C_2-C_{10})$aryl, or $(C_2-C_{10})$aryl $(C_1-C_4)$alkyl. In certain embodiments, $R^2$ is $(C_1-C_4)$alkyl, $(C_6-C_{10})$aryl, or $(C_6-C_{10})$aryl $(C_1-C_4)$alkyl. In certain embodiments, $R^2$ is $C_1-C_4$alkyl. In certain embodiments, $R^2$ is —$CH_3$.

In certain embodiments, after the addition is complete the reaction is heated to about 20 to 70° C., about 20 to 60° C., about 20 to 50° C., about 20 to 40° C., about 20 to 30° C., about 30 to 80° C., about 30 to 70° C., about 30 to 60° C., about 30 to 50° C., about 30 to 40° C., about 40 to 80° C., about 40 to 70° C., about 40 to 60° C., about 40 to 50° C., about 50 to 80° C., about 50 to 70° C., about 50 to 60° C., about 60 to 80° C., about 60 to 70° C., about 70 to 80° C., or any subrange therebetween.

In particular embodiments, the first solvent is an alcohol, the base is an alkoxide, after the addition is complete the reaction is heated to about 40 to about 50° C. and $R^2$ is $(C_1-C_4)$alkyl.

In particular embodiments, the first solvent is methanol, the base is sodium methoxide, after the addition is complete the reaction is heated to about 40 to about 50° C. and $R^2$ is —$CH_3$.

D. Alkylation and Cyclization of C-1 to Form F-1:

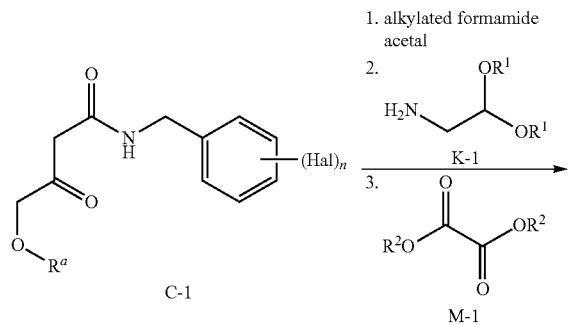

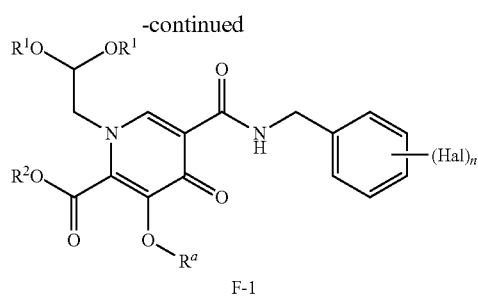

F-1

In certain embodiments, about one equivalent of C-1 and about 1 to about 5 equivalents of an alkylated formamide acetal are combined in a reaction vessel, and reaction mixture is agitated for approximately 30 minutes. In certain embodiments, about one equivalent of C-1 and about 1 to about 3 equivalents of an alkylated formamide acetal are combined in a reaction vessel. A first suitable solvent and about one equivalent of K-1 are added to the mixture, and the reaction is allowed to proceed for several hours, after which the first solvent is removed by any suitable means known in the art.

The resulting material is dissolved in a second suitable solvent and about 1 to about 5 equivalents of M-1 is added. The reaction mixture is cooled to about 0° C. to about 5° C., and then about one and a half to two equivalents of a base is slowly added to the reaction mixture. The internal temperature of the reaction is kept cool throughout the addition (e.g., below room temperature, or below about 25° C., or below about 20° C., or below about 15° C.). After the addition is complete the reaction is heated to about 20 to 80° C. for about 8 to about 16 hours.

After this time has elapsed, the reaction is cooled to room temperature, quenched via the addition of an acid and diluted with the addition of an organic solvent. The product, F-1, may then be extracted and purified by any suitable methods known in the art, including but not limited to solvent extraction, crystallization and silica gel chromatography.

In certain embodiments, $R^a$ is $(C_1-C_4)$alkyl, $(C_2-C_{10})$aryl, or $(C_2-C_{10})$aryl $(C_1-C_4)$alkyl. In certain embodiments, $R^a$ is $(C_1-C_4)$alkyl, $(C_6-C_{10})$aryl, or $(C_6-C_{10})$aryl $(C_1-C_4)$alkyl. In certain embodiments, $R^a$ is $C_1-C_4$alkyl. In certain embodiments, $R^a$ is —$CH_3$.

In a particular embodiment, the first solvent is a non-protic polar organic solvent such as, but not limited to, 2-methyl tetrahydrofuran, tetrahydrofuran, acetonitrile, diisopropyl ether, methyl tert-butyl ether, N,N-dimethylformamide, N,N-dimethylacetamide, 1,4-dioxane, N-methyl-2-pyrrolidinone, or mixtures thereof. In a further embodiment, the first solvent is 2-methyl tetrahydrofuran.

In certain embodiments, the alkylated formamide acetal is selected from the group consisting of N,N-dimethylformamide dimethyl acetal, N,N-dimethylformamide diethyl acetal, N,N-dimethylformamide diisopropyl acetal, N,N-diethylformamide dimethyl acetal, and N,N-diisopropylformamide dimethyl acetal. In a particular embodiment, the alkylated formamide acetal is N,N-dimethylformamide dimethyl acetal.

In certain embodiments, $R^1$ is $(C_1-C_4)$alkyl, $(C_2-C_{10})$aryl, or $(C_2-C_{10})$aryl $(C_1-C_4)$alkyl. In certain embodiments, $R^1$ is $(C_1-C_4)$alkyl, $(C_6-C_{10})$aryl, or $(C_6-C_{10})$aryl $(C_1-C_4)$alkyl. In certain embodiments, $R^1$ is $C_1-C_4$alkyl. In further embodiments $R^1$ is —$CH_3$, that is K-1 is aminoacetaldehyde dimethyl acetal.

In particular embodiments, the base is a metal hydride, a bis(trialkylsilyl) amide base, or an alkoxide. In certain embodiments, the base is a metal hydride. In particular embodiments, the base is a bis(trialkylsilyl) amide base. In particular embodiments, the base is an alkoxide. Exemplary metal hydrides include, but are not limited to lithium hydride, sodium hydride, and potassium hydride. Exemplary bis(trialkylsilyl) amide bases include, but are not limited to lithium bis(trimethylsilyl)amide, sodium bis(trimethylsilyl)amide, and potassium bis(trimethylsilyl)amide. Exemplary alkoxides include, but are not limited to, sodium methoxide, sodium tert-butoxide, sodium ethoxide, potassium tert-butoxide, potassium ethoxide, sodium tert-pentoxide, and lithium tert-butoxide. In still further embodiments, the base is a mixture of at least one of the foregoing bases. In certain embodiments, the base is a mixture of up to three, or up to two, metal hydrides. In certain embodiments, the base is a mixture of up to three, or up to two, bis(trialkylsilyl) amide base. In certain embodiments, the base is a mixture of up to three, or up to two, alkoxides. In certain embodiments, the base is a mixture of up to three, or up to two, bases selected from the group consisting of lithium hydride, sodium hydride, potassium hydride, lithium bis(trimethylsilyl)amide, sodium bis(trimethylsilyl)amide, potassium bis(trimethylsilyl)amide, sodium methoxide, sodium tert-butoxide, sodium ethoxide, potassium tert-butoxide, potassium ethoxide, sodium tert-pentoxide, and lithium tert-butoxide. In particular embodiments, the base is sodium methoxide. In particular embodiments, a solution of base in alcohol is added to the reaction. A suitable alcohol includes but is not limited to, methanol, ethanol, n-propanol, 2-propanol, butanol, or tert-butanol. In a certain embodiment, the base is sodium methoxide. In a certain embodiment, the base is added as 30% solution of sodium methoxide in methanol.

In particular embodiments, the second solvent is an alcohol or a polar solvent. In certain embodiments, the second solvent is an alcohol. In certain embodiments, the second solvent is a polar solvent. Exemplary alcohols include, but are not limited to, methanol, ethanol, n-propanol, 2-propanol, butanol, and tert-butanol. Exemplary polar organic solvents include, but are not limited to, acetone, acetonitrile, N,N-dimethylformamide, N,N-dimethylacetamide, 1,4-dioxane, or N-methyl-2-pyrrolidinone. In a certain embodiment, the second solvent is methanol.

In certain embodiments, $R^2$ is $(C_1-C_4)$alkyl, $(C_2-C_{10})$aryl, or $(C_2-C_{10})$aryl $(C_1-C_4)$alkyl. In certain embodiments, $R^2$ is $(C_1-C_4)$alkyl, $(C_6-C_{10})$aryl, or $(C_6-C_{10})$aryl $(C_1-C_4)$alkyl. In certain embodiments, $R^2$ is $C_1-C_4$alkyl. In certain embodiments, $R^2$ is —$CH_3$.

In certain embodiments, after the addition is complete the reaction is heated to about 20 to 70° C., about 20 to 60° C., about 20 to 50° C., about 20 to 40° C., about 20 to 30° C., about 30 to 80° C., about 30 to 70° C., about 30 to 60° C., about 30 to 50° C., about 30 to 40° C., about 40 to 80° C., about 40 to 70° C., about 40 to 60° C., about 40 to 50° C., about 50 to 80° C., about 50 to 70° C., about 50 to 60° C., about 60 to 80° C., about 60 to 70° C., about 70 to 80° C., or any subrange therebetween.

In particular embodiments, $R^a$ is $(C_1-C_4)$alkyl, the first solvent is 2-methyl tetrahydrofuran, the alkylated formamide acetal is N,N-dimethylformamide dimethyl acetal, $R^1$ is $(C_1-C_4)$alkyl, the base is an alkoxide, the second solvent is an alcohol, after the addition is complete the reaction is heated to about 40 to about 50° C., and $R^2$ is $(C_1-C_4)$alkyl.

In particular embodiments, $R^a$ is —$CH_3$, the first solvent is 2-methyl tetrahydrofuran, the alkylated formamide acetal is N,N-dimethylformamide dimethyl acetal, $R^1$ is —$CH_3$, the base is sodium methoxide, the second solvent is methanol, after the addition is complete the reaction is heated to about 40 to about 50° C., and $R^2$ is —$CH_3$.

E. Preparation of EE-1 from D-1

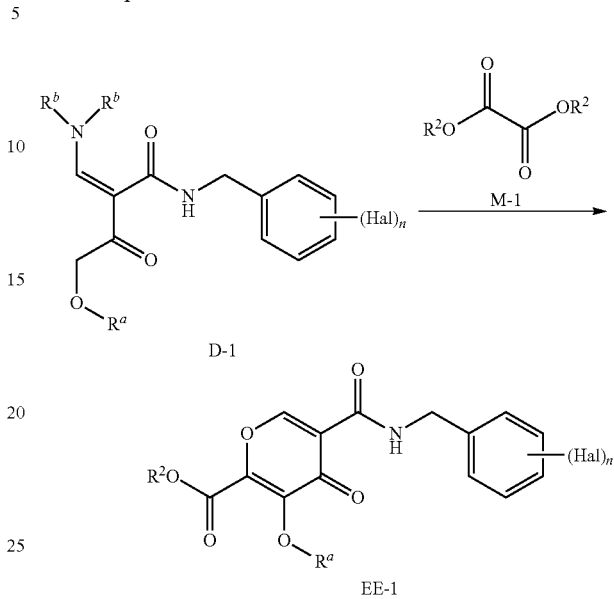

D-1 is reacted with M-1 to yield EE-1. For example. D-1 is dissolved in a suitable solvent and about 1 to about 5 equivalents of M-1 is added. The reaction mixture is cooled to about 0° C. to about 5° C., and then about one and a half to two equivalents of a base is slowly added to the reaction mixture. The internal temperature of the reaction is kept cool throughout the addition (e.g., below room temperature, or below about 25° C., or below about 20° C., or below about 15° C.). After the addition is complete the reaction is heated to about 20 to 80° C. for about 8 to about 16 hours.

After this time has elapsed, the reaction is cooled to room temperature, quenched via the addition of an acid and diluted with the addition of an organic solvent. The product, EE-1, may then be extracted and purified by any suitable methods known in the art, including but not limited to solvent extraction, crystallization and silica gel chromatography.

In certain embodiments, $R^a$ is $(C_1-C_4)$alkyl, $(C_2-C_{10})$aryl, or $(C_2-C_{10})$aryl $(C_1-C_4)$alkyl. In certain embodiments, $R^a$ is $(C_1-C_4)$alkyl, $(C_6-C_{10})$aryl, or $(C_6-C_{10})$aryl $(C_1-C_4)$alkyl. In certain embodiments, $R^a$ is $C_1-C_4$alkyl. In particular embodiments, $R^a$ is —$CH_3$.

In certain embodiments, $R^b$ is $(C_1-C_4)$alkyl, $(C_2-C_{10})$aryl, or $(C_2-C_{10})$aryl $(C_1-C_4)$alkyl. In certain embodiments, In certain embodiments, each $R^b$ is, independently $(C_1-C_4)$alkyl, $(C_6-C_{10})$aryl, or $(C_6-C_{10})$aryl $(C_1-C_4)$alkyl. In certain embodiments, $R^b$ is $C_1-C_4$alkyl. In further embodiments $R^b$ is —$CH_3$. In certain embodiments, In certain embodiments, each $R^b$ is —$CH_3$.

In particular embodiments, the base is an inorganic carbonate, a metal hydride, or an alkoxide, or a mixture thereof. In particular embodiments, the base is an inorganic carbonate. In particular embodiments, the base is a metal hydride. In particular embodiments, the base is an alkoxide. Exemplary inorganic carbonates include, without limitation, lithium carbonate, sodium carbonate, potassium carbonate and cesium carbonate. Exemplary metal hydrides include, without limitation, sodium hydride and potassium hydride. Exemplary alkoxides include, without limitation, sodium methoxide, sodium tert-butoxide, sodium ethoxide, potassium tert-butoxide, potassium ethoxide, sodium tert-pentoxide, and lithium tert-butoxide. In certain embodiments, the base is a mixture of up to three, or in other embodiments, up to two, inorganic carbonates. In certain embodiments, the base is a mixture of up to three, or in other embodiments, up to two, metal hydrides. In certain embodiments, the base is a mixture of up to three, or in other embodiments, up to two, alkoxides. In certain embodiments, the base is a mixture of up to three, or in other embodiments, up to two, bases selected from the group consisting of lithium carbonate, sodium carbonate, potassium carbonate, cesium carbonate, sodium hydride, potassium hydride, sodium tert-butoxide, sodium ethoxide, potassium tert-butoxide, potassium ethoxide, sodium tert-pentoxide, and lithium tert-butoxide. In particular embodiments, the base is sodium methoxide.

In particular embodiments, the solvent is an alcohol or a polar solvent. In certain embodiments, the solvent is an alcohol. In certain embodiments, the solvent is a polar solvent. Exemplary alcohols include, but are not limited to, methanol, ethanol, n-propanol, 2-propanol, butanol, and tert-butanol. Exemplary polar organic solvents include, but are not limited to, acetone, acetonitrile, N,N-dimethylformamide, N,N-dimethylacetamide, 1,4-dioxane, or N-methyl-2-pyrrolidinone. In a certain embodiment, the solvent is N-methyl-2-pyrrolidinone.

In certain embodiments, the reaction is quenched with an inorganic acid, an organic acid, or a halogenated organic acid. In certain embodiments, the acid is an inorganic acid. In certain embodiments, the acid is an organic acid. In certain embodiments, the acid is a halogenated organic acid. Exemplary inorganic acids, include, but are not limited to hydrochloric acid, hydrobromic acid, hydroiodic acid. Exemplary organic acids, include, but are not limited to, formic acid and acetic acid. Exemplary halogenated organic acids include, but are not limited to, trifluoromethanesulfonic acid, trifluoroacetic acid, trichloroacetic acid, and perfluoropropionic acid. In still further embodiments, the acid is a mixture comprising one or more organic acids, one or more inorganic acids, and/or one or more halogenated organic acids. In certain embodiments, the acid is a mixture comprising up to three, or up to two, organic acids. In certain embodiments, the acid is a mixture comprising up to three, or up to two, halogenated organic acids. In certain embodiments, the acid is a mixture comprising up to three, or up to two, inorganic acids. In a certain embodiment, the acid is a mixture of up to three, or up to two, acids selected from the group consisting of hydrochloric acid, hydrobromic acid, hydroiodic acid, formic acid, trifluoromethanesulfonic acid, trifluoroacetic acid, trichloroacetic acid, and perfluoropropionic acid. In a particular embodiment, the acid is trifluoroacetic acid. In particular embodiments, the reaction is quenched with hydrochloric acid. In particular embodiments, the reaction is quenched with 2 N HCl. In certain embodiments, the reaction is not quenched.

In certain embodiments, $R^2$ is $(C_1-C_4)$alkyl, $(C_2-C_{10})$aryl, or $(C_2-C_{10})$aryl $(C_1-C_4)$alkyl. In certain embodiments, $R^2$ is $(C_1-C_4)$alkyl, $(C_6-C_{10})$aryl, or $(C_6-C_{10})$aryl $(C_1-C_4)$alkyl. In certain embodiments, $R^2$ is $C_1-C_4$alkyl. In certain embodiments, $R^2$ is —$CH_3$.

In certain embodiments, after the addition is complete the reaction is heated to about 20 to 80° C., about 20 to 80° C., about 20 to 60° C., about 20 to 50° C., about 20 to 40° C., about 20 to 30° C., about 30 to 80° C., about 30 to 70° C., about 30 to 60° C., about 30 to 50° C., about 30 to 40° C., about 40 to 80° C., about 40 to 70° C., about 40 to 60° C., about 40 to 50° C., about 50 to 80° C., about 50 to 70° C., about 50 to 60° C., about 60 to 80° C., about 60 to 70° C., about 70 to 80° C., or any subrange therebetween.

In particular embodiments, $R^2$ is $(C_1-C_4)$alkyl, each $R^b$ is $(C_1-C_4)$alkyl which are the same or different, $R^a$ is $(C_1-C_4)$alkyl, the base is an alkoxide, and the solvent is an organic solvent.

In particular embodiments, $R^2$ is —$CH_3$, each $R^b$ is —$CH_3$, $R^a$ is —$CH_3$, the base is sodium methoxide, and the solvent is N-methyl-2-pyrrolidinone.

F. Condensation of F-1 with N-1 to form G-1:

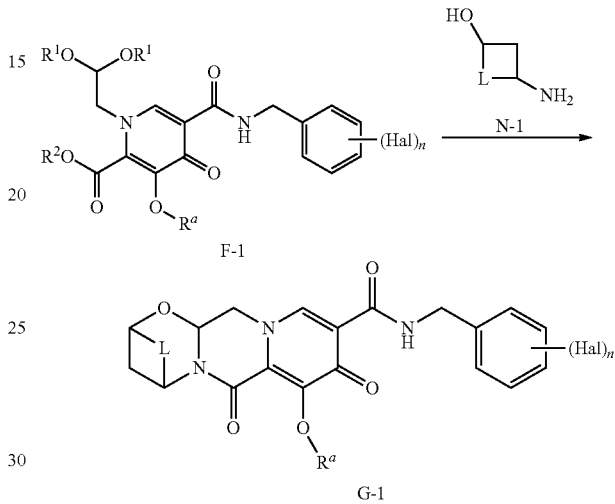

One equivalent of F-1 and a suitable solvent are combined in a reaction vessel, about 5 to 8 equivalents of a first acid and about 0.2 to about 0.5 equivalent of a second acid are added. The reaction may take place between about 20 to about 100° C.

The reaction is allowed to continue for about 2 to about 5 hours, after which about 1.5 equivalents of N-1 and about 2 to about 3 equivalents of a base are slowly introduced to the reaction vessel. After the addition is completed, the reaction is allowed to progress for at least about 1 hour.

Water and additional solvent are added to the reaction vessel and G-1 is extracted and purified by any suitable method known in the art, including but not limited to solvent extraction, silica gel chromatography and crystallization.

In particular embodiments, the solvent is a non-protic polar organic solvent, such as, but not limited to, tetrahydrofuran, acetonitrile, diisopropyl ether, methyl tert-butyl ether, N,N-dimethylformamide, N,N-dimethylacetamide, 1,4-dioxane, or N-methyl-2-pyrrolidinone, or mixtures thereof. In certain embodiments, the solvent is a mixture of one, two or three, or in certain embodiments, a mixture of one or two of the following solvents: tetrahydrofuran, acetonitrile, diisopropyl ether, methyl tert-butyl ether, N,N-dimethylformamide, N,N-dimethylacetamide, 1,4-dioxane, or N-methyl-2-pyrrolidinone. In further embodiments, the solvent is acetonitrile.

In certain embodiments, the first acid is an organic acid, an organic carboxylic acid, or an inorganic acid. In certain embodiments, the first acid is an organic acid. In certain embodiments, the first acid is an organic carboxylic acid. In certain embodiments, the first acid is an inorganic acid. Exemplary organic acids include, but are not limited to methane sulfonic acid, trifluoromethanesulfonic acid and trifluoroacetic acid. Exemplary organic carboxylic acids include, but are not limited to acetic acid, formic acid, butyric acid, propionic acid, and benzoic acid. Exemplary inorganic acids include, but are not limited to, hydrochloric acid, hydrobromic acid, nitric acid, phosphoric acid, or sulfuric acid. In yet further embodiments, the first acid is acetic acid.

In certain embodiments, the second acid is an organic acid, an organic carboxylic acid, or an inorganic acid. In certain embodiments, the second acid is an organic acid. In certain embodiments, the second acid is an organic carboxylic acid. In certain embodiments, the first acid is an inorganic acid. Exemplary organic acids include, but are not limited to methanesulfonic acid, trifluoromethanesulfonic acid and trifluoroacetic acid. Exemplary inorganic acids include, but are not limited to, hydrochloric acid, hydrobromic acid, and sulfuric acid. Exemplary organic carboxylic acids include, but are not limited to acetic acid, formic acid, butyric acid, propionic acid, or benzoic acid. In particular embodiments, the second acid is methanesulfonic acid or formic acid.

In certain embodiments, the first acid is acetic acid and the second acid is methanesulfonic acid.

In certain embodiments, the first acid and the second acid are the same acid. In yet other embodiments, the first acid and the second acid are formic acid or acetic acid.

In certain embodiments, N-1 is in solution when added to the reaction mixture.

In further embodiments, L is —CH₂—CH₂—, that is, N-1 is (1R,3S)-3-aminocyclopentan-1-ol:

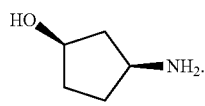

In some embodiments, N-1 is

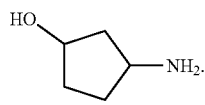

(3-aminocyclopentanol)

In particular embodiments, N-1 is a salt or co-crystal. Suitable salts or co-crystals of N-1 include, but are not limited to, oxalic acid, hydrochloric acid, mandelic acid, R-mandelic acid, and S-mandelic acid. Suitable salts or co-crystals of N-1 include, but are not limited to, benzoic acid, naproxen, S-naproxen and R-naproxen.

In still further embodiments, N-1 is

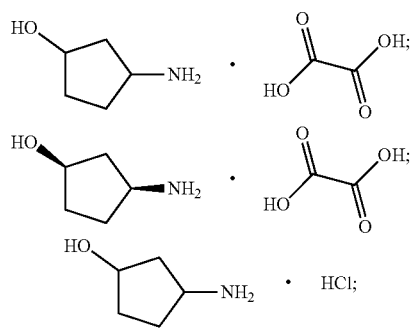

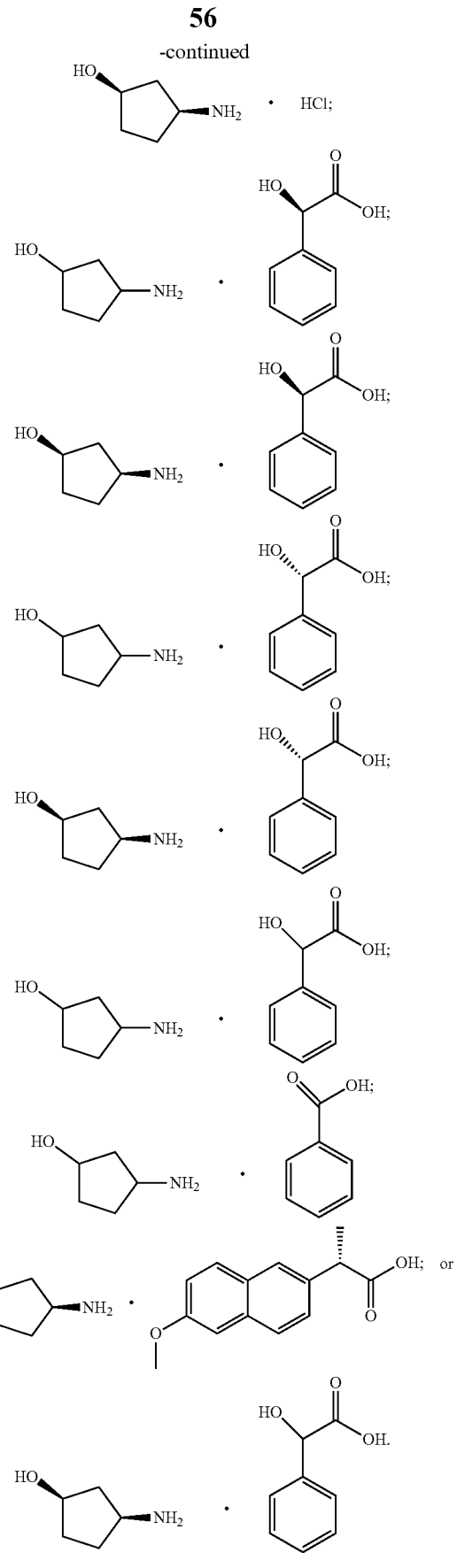

In still further embodiments, N-1 is;

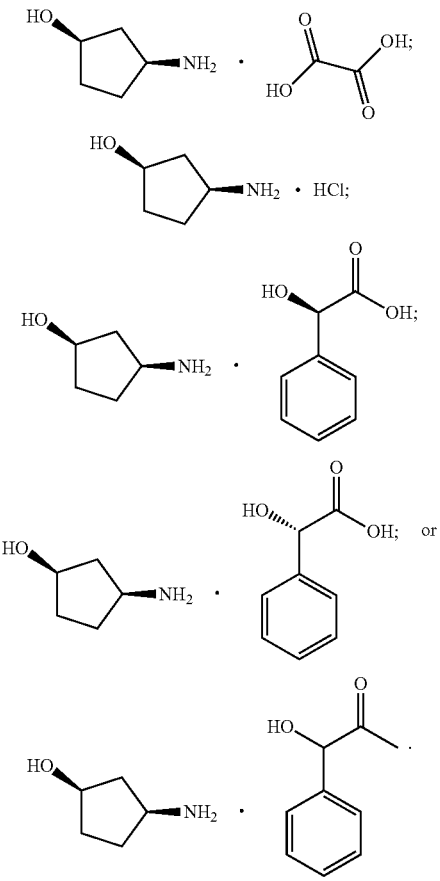

In certain embodiments, after the addition of the acid(s) the reaction is kept at about 20 to about 90° C., about 20 to about 80° C., about 20 to about 70° C., about 20 to about 60° C., about 20 to about 50° C., about 20 to about 40° C., about 20 to about 30° C., about 30 to about 100° C., about 30 to about 90° C., about 30 to about 80° C., about 30 to about 70° C., about 30 to about 60° C., about 30 to about 50° C., about 30 to about 40° C., about 40 to about 100° C., about 40 to about 90° C., about 40 to about 80° C., about 40 to about 70° C., about 40 to about 60° C., about 40 to about 50° C., about 50 to about 100° C., about 50 to about 90° C., about 50 to about 80° C., about 50 to about 70° C., about 50 to about 60° C., about 60 to about 100° C., about 60 to about 90° C., about 60 to about 80° C., about 60 to about 70° C., about 70 to about 80° C., or any subrange therebetween. In still further embodiments, after the addition of the acid(s) the reaction is kept at about 65 to about 70° C., about 70 to about 75° C., about 75 to about 80° C., or any subrange therebetween.

In particular embodiments, the solvent is acetonitrile, the first acid is an organic carboxylic acid, the second acid is an organic carboxylic acid, and after the addition of the acids the reaction is kept at about 70 to about 75° C.

In particular embodiments, the solvent is acetonitrile, the first acid is acetic acid, the second acid is methanesulfonic acid, after the addition of the acids the reaction is kept at about 70 to about 75° C., and N-1 is

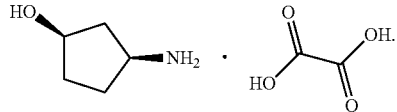 [SMILES: N[C@H]1CC[C@@H](O)C1 ; O=C(O)C(=O)O]

G. Deprotection of G-1 to Form a Compound of Formula I:

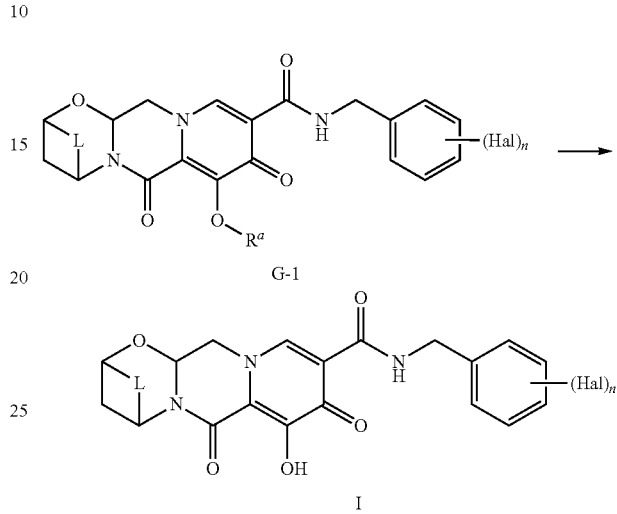

A reaction vessel is charged with approximately one equivalent of G-1 and a suitable solvent. About two to three equivalents of a metal salt, a Lewis acid, or other reagent is added to the solution. The resulting suspension is stirred at about 40 to about 100° C. for about ten minutes to about three hours. The reaction is quenched by the addition of an acid and a compound of Formula I is then extracted and purified by any suitable technique known in the art, such as, but not limited to, solvent extraction, preparative HPLC and crystallization.

In a particular embodiment, the solvent is a non-protic polar organic solvent such as, but not limited to, 2-methyl tetrahydrofuran, tetrahydrofuran, acetonitrile, diisopropyl ether, methyl tert-butyl ether, N,N-dimethylformamide, N,N-dimethylacetamide, 1,4-dioxane, N-methyl-2-pyrrolidinone, or mixtures thereof. In a further embodiment, the solvent is acetonitrile.

In certain embodiments, G-1 is reacted with at least one reagent selected from the group consisting of metal salts, Lewis acids, sodium ethanethiolate, sodium hexamethyldisiloxane, trifluoroacetic acid, and combinations thereof.

In further embodiments, the metal salt is selected from the group consisting of magnesium bromide, lithium chloride, lithium bromide, and lithium iodide. In still further embodiments, the metal salt is lithium chloride.

In particular embodiments, the Lewis acid is selected from the group consisting of boron trifluoride methyl etherate, boron trifluoride diethyl etherate, boron trifluoride dibutyl etherate, aluminium chloride, aluminum bromide, boron trichloride, boron tribromide, chlorotrimethylsilane, iodotrimethylsilane, palladium, and boron trifluoride diethyl etherate. In certain embodiments, the Lewis acid is selected from the group consisting of chlorotrimethylsilane, iodotrimethylsilane, sodium ethanethiolate, sodium hexamethyldisiloxane, palladium, boron trifluoride diethyl etherate, and trifluoroacetic acid.

In particular embodiments, other reagents suitable to facilitate the conversion are sodium ethanethiolate, sodium hexamethyldisiloxane, and trifluoroacetic acid In particular embodiments, the deprotection of G-1 to form a compound of Formula I takes place in the presence of about two to about three equivalents of a reagent selected from the group consisting of: magnesium bromide, lithium chloride, lithium bromide, lithium iodide, boron trifluoride methyl etherate, boron trifluoride diethyl etherate, boron trifluoride dibutyl etherate, aluminium chloride, aluminum bromide, boron trichloride, boron tribromide, chlorotrimethylsilane, iodotrimethylsilane, palladium, boron trifluoride diethyl etherate, chlorotrimethylsilane, iodotrimethylsilane, sodium ethanethiolate, sodium hexamethyldisiloxane, palladium, boron trifluoride diethyl etherate, and trifluoroacetic acid.

In certain embodiments, the reaction proceeds at about 40 to about 50° C., about 40 to about 60° C., about 40 to about 70° C., about 50 to about 60° C., about 50 to about 70° C., about 50 to about 80° C., about 60 to about 70° C., about 60 to about 80° C., or any subrange therebetween. In particular embodiments, the reaction proceeds at about 50° C.

In particular embodiments, the solvent is acetonitrile, the metal salt is magnesium bromide, and the reaction proceeds at about 50° C.

H. Hydrolysis of F-1 to Yield a Compound of Formula II:

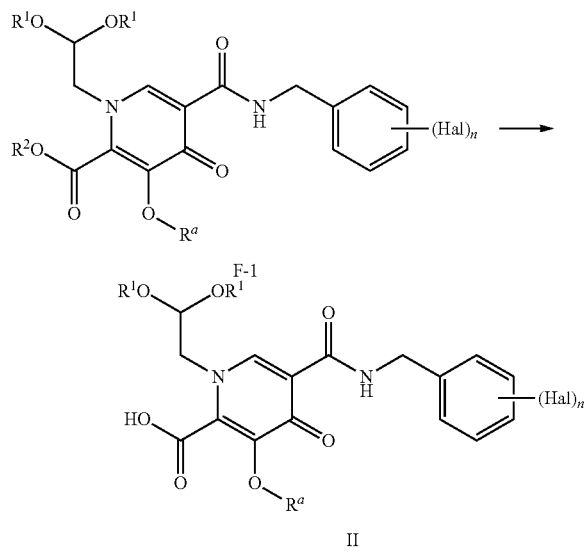

A reaction vessel is charged with approximately one equivalent of F-1 and a solution of about ten to fifteen parts of a first organic solvent and about 3 to 8 parts water is prepared. About two equivalents of a base are added to the solution. The resulting suspension is stirred at about 0 to about 50° C. for about 14 to about 17 hours. Conversion may be monitored by any suitable method known in the art, such as, but not limited to HPLC.

Water and a second organic solvent are added to the suspension and the pH adjusted to about pH 3 by the dropwise addition of a suitable acid. The product, a compound of Formula II, can then be extracted and optionally purified by any suitable technique known in the art, such as, but not limited to, solvent extraction, silica gel chromatography and crystallization.

In certain embodiments, the first organic solvent is an alcoholic solvent or a polar organic solvent. In certain embodiments, the first organic solvent is an alcoholic solvent. In certain embodiments, the first organic solvent is a polar organic solvent. Exemplary alcoholic solvents include, without limitation, methanol, ethanol, n-propanol, 2-propanol, butanol, and tert-butanol. Exemplary polar organic solvents include, but are not limited to, N,N-dimethylformamide, N,N-dimethylacetamide, 1,4-dioxane, and N-methyl-2-pyrrolidinone. In particular embodiments, the first organic solvent is methanol.

In further embodiments, the base is selected from the group consisting of lithium hydroxide, sodium hydroxide, potassium hydroxide, lithium carbonate, sodium carbonate and potassium carbonate. In still further embodiments, the base is lithium hydroxide monohydrate.

In certain embodiments, the reaction proceeds at about 10 to about 50° C., about 10 to about 40° C., about 10 to about 30° C., about 10 to about 20° C., about 20 to about 50° C., about 20 to about 40° C., about 20 to about 30° C., about 30 to about 50° C., about 30 to about 40° C., about 40 to about 50° C., or any subrange therebetween. In particular embodiments, the reaction proceeds at room temperature. In further embodiments, the reaction proceeds at about 18 to about 23° C.

In particular embodiments, the base is lithium hydroxide monohydrate, the reaction proceeds at about 10 to about 50° C. and the first organic solvent is methanol.

In particular embodiments, the base is lithium hydroxide monohydrate, the reaction proceeds at about 18 to about 23° C. and the first organic solvent is methanol.

I. Preparation of BB-1 from B-1 and Q-1:

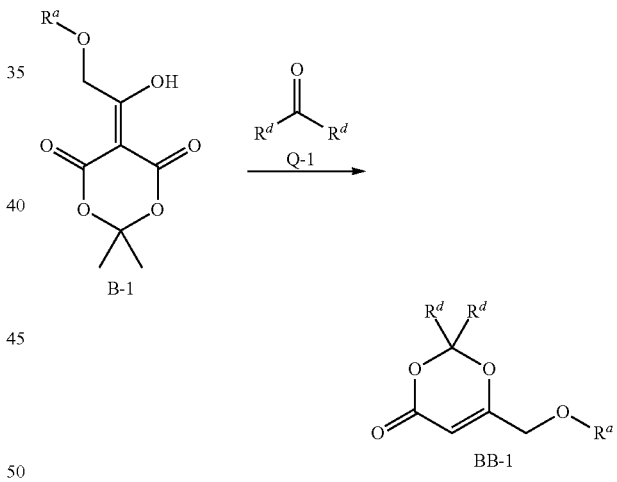

About one equivalent of B-1 and eight to twelve equivalents of Q-1 are added to a reaction vessel and dissolved in a suitable organic solvent. The solution is then heated to about 85 to about 115° C. and allowed to proceed for about two to six hours, after which time the reaction is cooled to room temperature. BB-1 is then purified using techniques known in the art, such as, but not limited to silica gel chromatography.

In certain embodiments, the solvent is a non-polar aromatic solvent or a polar aprotic solvent. In certain embodiments, the solvent is a non-polar aromatic solvent. In certain embodiments, the solvent is a polar aprotic solvent. Exemplary non-polar aromatic include, but are not limited to, toluene, xylene, chlorobenzene, and dichlorobenzene. Exemplary polar aprotic solvents include, but are not limited to, N,N-dimethylformamide, N,N-dimethylacetamide, 1,4- dioxane, and N-methylpyrrolidinone. In still further embodiments, the reaction can occur without additional solvent. In particular embodiments, the solvent is toluene.

In certain embodiments, the reaction proceeds at about 85 to about 105° C., about 85 to about 95° C., about 95 to about 105° C., about 95 to about 115° C., about 105 to about 115° C., about 100 to about 105° C., about 105 to about 110° C., about 110 to about 115° C., or any subrange therebetween.

In particular embodiments, the reaction proceeds at about 95 to about 115° C., and the solvent is toluene.

In particular embodiments, the reaction proceeds at about 110 to about 115° C., and the solvent is toluene.

J. Preparation of C-1 from BB-1:

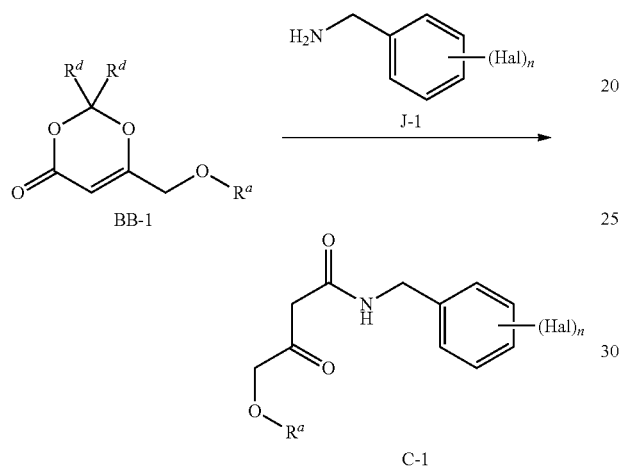

About 1 equivalent of BB-1 and about 1 to about 3 equivalents of J-1 are combined in a reaction vessel. The compounds are dissolved in a polar non-protic solvent or an aromatic solvent. In certain embodiments, the compounds are dissolved is suspended in a polar non-protic solvent. In certain embodiments, the compounds are dissolved in an aromatic solvent. Exemplary polar non-protic solvent include, but are not limited to, acetonitrile, N,N-dimethylformamide, N,N-dimethylacetamide, 1,4-dioxane, and N-methyl-2-pyrrolidinone. Exemplary aromatic solvents include, but are not limited to, pyridine, toluene, xylene, benzene, and chlorobenzene. In still further embodiments, the compounds are dissolved in a solvent mixture comprising one or more polar non-protic solvents and/or one or more aromatic solvents. In certain embodiments, the compounds are dissolved in a solvent mixture comprising up to three, or up to two, polar non-protic solvents. In certain embodiments, the compounds are dissolved in a solvent mixture comprising up to three, or up to two, aromatic solvents. In certain embodiments, the compounds are dissolved in a solvent mixture comprising up to three, or up to two, solvents from the group consisting of acetonitrile, N,N-dimethylformamide, N,N-dimethylacetamide, 1,4-dioxane, N-methyl-2-pyrrolidinone, pyridine, toluene, xylene, benzene, and chlorobenzene. In a further embodiment the compounds are dissolved in toluene.

In particular embodiments, each Hal is independently —F or —Cl. In a particular embodiment, Hal is —F In certain embodiments, n=1-3. In certain embodiments, n=2. In certain embodiments, n=3. In further embodiments, J-1 is

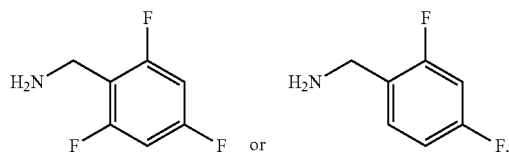 [SMILES: NCc1c(F)cc(F)cc1F ; "or" ; NCc1ccc(F)cc1F]

In certain embodiments, J-1 is

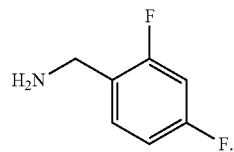

In further embodiments, J-1 is

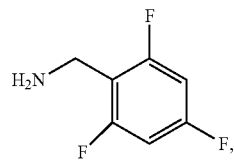

In still further embodiments, J-1 is in the form of a salt or co-crystal, such as, but not limited to a salt or co-crystal of hydrochloric acid or trifluoroacetic acid. In certain embodiments, J-1 is a salt or co-crystal of methane sulfonic acid.

In certain embodiments, the reaction proceeds at about 65 to about 115° C., about 75 to about 115° C., about 85 to about 115° C., about 95 to about 115° C., about 105 to about 115° C., about 65 to about 70° C., about 70 to about 80° C., about 80 to about 90° C., about 90 to about 100° C., about 100 to about 110° C., about 110 to about 115° C., or any subrange therebetween.

In certain embodiments, the solvent is removed under reduced pressure. In particular embodiments, C-1 is extracted from the crude residue by solvent extraction. The resulting crude material is purified using any suitable technique, such as silica gel chromatography or crystallization to yield C-1.

In particular embodiments, the compounds are dissolved in an aromatic solvent, J-1 is and the reaction proceeds at about 65 to about 115° C.

In particular embodiments, the compounds are dissolved in toluene, J-1 is

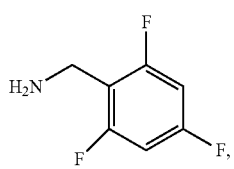

and the reaction proceeds at about 100 to about 110° C.

K. Preparation of C-1 from B-1.J-1

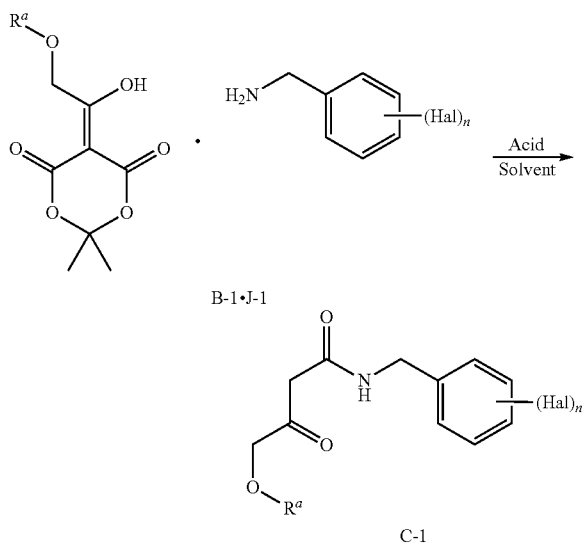

B-1.J-1, a solvent and an acid are combined in a reactor under conditions effective to produce C-1.

In certain embodiments, the acid is absent. In certain embodiments, the acid is a protic acid or a Lewis acid. In certain embodiments, protic acids include but are not limited to trifluoroacetic acid, trichloroacetic acid, dichloroacetic acid, chloroacetic acid, acetic acid, formic acid, hydrochloric acid, hydrobromic acid, para-toluenesulfonic acid and methane sulfonic acid. In certain embodiments, Lewis acids include but are not limited to zinc chloride, magnesium bromide, magnesium triflate, copper triflate, and scandium triflate. In particular embodiments, the acid is trifluoroacetic acid.

In certain embodiments, about 10 equivalents, about 5 equivalents, about 1 equivalents, or about 0.1 equivalent of acid is used in the reaction of B-1.J-1 to form C-1.

In certain embodiments, the solvent is toluene, heptane, water, 2-methyltetrahydrofuran, iso-propylacetate, N,N-dimethylformamide, N-methyl-2-pyrrolidinone, methyl-tert-butyl ether, dimethylsulfoxide, n-butanol, acetonitrile, acetone, or a mixture thereof. In a particular embodiment, the solvent is acetonitrile.

In certain embodiments, B-1.J-1 is at a concentration ranging from about 2 to 40 mL/g, about 2 to 20 mL/g, about 5 to 15 mL/g. In a particular embodiment, B-1.J-1 is at a concentration of about 10 mL/g.

In certain embodiments, the reaction mixture is heated to a temperature between about 20 and 110° C., about 30 and 90° C., about 40 and 80° C., about 50 and 70° C., about 55 and 65° C., or about 58 and 61° C. In a particular embodiment, the reaction mixture is heated to about 60° C.

In certain embodiments, other additives are added to the reaction. In certain embodiments, the additives include but are not limited to lithium chloride, sodium chloride, and potassium chloride.

In certain embodiments, B-1.J-1 is charged to the reactor in a single portion at about 20° C. followed by heating. In certain embodiments, B-1.J-1 is charged to the reactor in portions over 1 hour during heating.

In certain embodiments, the reaction is heated for about 1 to 24 hours, for about 2 to 12 hours, or for about 3 to 6 hours. In a particular embodiment, the reaction is heated for about 2.5 hours.

In certain embodiments, the product formed is extracted and optionally purified by any suitable technique known in the art, such as, but not limited to solvent extraction, chromatography, crystallization or a combination thereof.

In certain embodiments, the reaction is cooled down and the reactor contents are partially distilled.

In certain embodiments, the organic phase is washed at least once with an aqueous solution. In certain embodiments, the aqueous solution contains about 23% NaCl, about 1.5% $H_2SO_4$, and about 76% water. In certain embodiments, the aqueous solution contains about 20% NaCl.

In certain embodiments, a solution of the product is seeded with seeds of C-1 which had been previously isolated. In certain embodiments, solid C-1 is isolated by filtration.

In particular embodiments, each Hal is independently —F or —Cl. In a particular embodiment, each Hal is —F In certain embodiments, n=1-3. In certain embodiments, n=2. In certain embodiments, n=3. In further embodiments, J-1 is

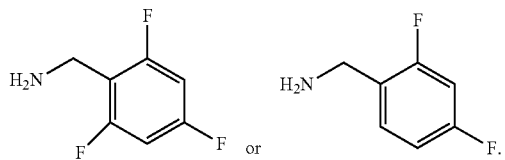

In certain embodiments, J-1 is

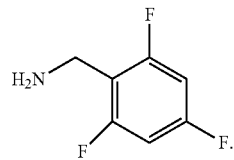 [SMILES: NCc1c(F)cc(F)cc1F]

In further embodiments, J-1 is

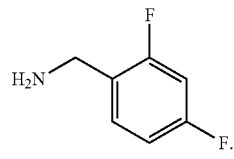

In certain embodiments, $R^a$ is $(C_1-C_4)$alkyl, $(C_6-C_{10})$aryl, or $(C_6-C_{10})$aryl$(C_1C_4)$alkyl. In certain embodiments, $R^a$ is $(C_1-C_4)$alkyl. In certain embodiments, $R^a$ is methyl.

In particular embodiments, $R^a$ is $(C_1-C_4)$alkyl, the solvent is acetonitrile, the reaction mixture is heated to about 60° C., and J-1 is

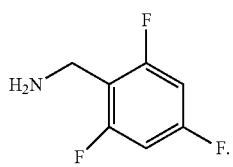

In particular embodiments, $R^a$ is methyl, the solvent is acetonitrile, the reaction mixture is heated to about 60° C., and J-1 is

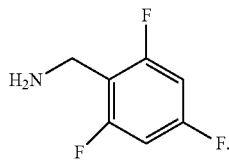 [SMILES: NCc1c(F)cc(F)cc1F]

L. Enamine Formation from C-1 to Provide D-1

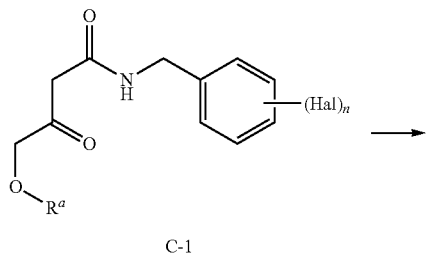

C-1

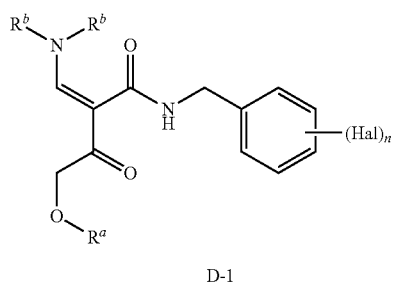

D-1

To a solution of C-1 and an acid in a solvent, about 0.5 to about 1.5 equivalent of an alkylated formamide acetal is added under conditions effective to produce D-1.

In particular embodiments, one equivalent of C-1 is combined with about 1.1 equivalents of the alkylated formamide acetal.

In certain embodiments, the alkylated formamide acetal is selected from the group consisting of N,N-dimethylformamide dimethyl acetal, N,N-dimethylformamide diethyl acetal, N, N-dimethylformamide diisopropyl acetal, N, N-diethylformamide dimethyl acetal, and N,N-diisopropylformamide dimethyl acetal. In a particular embodiment, the alkylated formamide acetal is N,N-dimethylformamide dimethyl acetal.

In certain embodiments, the solvent is dichloromethane, tetrahydrofuran, acetone, acetonitrile, ethyl acetate, isopropyl acetate, toluene, N,N-dimethylformamide, N,N-dimethylacetamide, 2-methyltetrahydrofuran or N-methyl-2-pyrrolidone. In a particular embodiment, the solvent is 2-methyltetrahydrofuran.

In certain embodiments, the acid is an organic acid. In certain embodiments, the organic acid includes, but is not limited to trifluoroacetic acid, formic acid, acetic acid, sulfuric acid, trifluoroacetic acid, trichloroacetic acid, and perfluoropropionic acid. In certain embodiments, the acid is a mixture comprising up to three, or up to two, organic acids. In a particular embodiment, the acid is trifluoroacetic acid.

In certain embodiments, the reaction mixture is heated to an internal temperature of about 40° C. before adding the alkylated formamide acetal.

In certain embodiments, the reaction proceeds at about 0 to 75° C., about 10 to 60° C., about 20 to 50° C., about 40 to 50° C., or about 30 to 40° C. In particular embodiments, the reaction proceeds at room temperature. In further embodiments, the reaction proceeds at about 40° C.

In certain embodiments, the reaction proceeds for about 0.1 hours to about 12 hours, for about 0.1 hours to about 6 hours, for about 0.1 hour to about 3 hours, for about 0.1 hour to about 1 hour, or for about 0.2 hour to about 0.5 hour.

In certain embodiments, D-1 is extracted and purified by any suitable methods known in the art, including but not limited to solvent extraction, crystallization, and chromatography.

In certain embodiments, seeds of D-1 are added and the mixture is stirred. In certain embodiments, the mixture is stirred at about 40° C. for at least 1 hour.

In certain embodiments, about 0.2 to 0.6 equivalent of alkylated formamide acetal is added and the reaction mixture is agitated for at least about 25 minutes. The reaction mixture is cooled to room temperature and allowed to stir for about 12 hours.

In certain embodiments, the contents of the reactor are filtered, and the filter cake is rinsed with a solvent and dried to yield D-1. In certain embodiments, the solvent is a combination of 2-methyltetrahydrofuran and heptanes.

In particular embodiments, each Hal is independently —F or —Cl. In a particular embodiment, each Hal is —F In certain embodiments, n=1-3. In certain embodiments, n=2. In certain embodiments, n=3.

In certain embodiments, $R^a$ is $(C_1$-$C_4)$alkyl, $(C_6$-$C_{10})$aryl, or $(C_6$-$C_{10})$aryl$(C_1C_4)$alkyl. In certain embodiments, $R^a$ is $(C_1$-$C_4)$alkyl. In certain embodiments, $R^a$ is methyl.

In certain embodiments, each $R^b$ is independently $(C_1$-$C_4)$alkyl, $(C_6$-$C_{10})$aryl, or $(C_6$-$C_{10})$aryl$(C_1C_4)$alkyl. In certain embodiments, each $R^b$ is independently $(C_1$-$C_4)$alkyl. In certain embodiments, $R^b$ is methyl.

In particular embodiments, $R^b$ is $(C_1$-$C_4)$alkyl, $R^a$ is $(C_1$-$C_4)$alkyl, the alkylated formamide acetal is N,N-dimethylformamide dimethyl acetal, the solvent is 2-methyltetrahydrofuran, the reaction proceeds at about 10 to about 60° C., the acid is trifluoroacetic acid, each Hal is —F and n=3.

In particular embodiments, $R^b$ is methyl, $R^a$ is methyl, the alkylated formamide acetal is N,N-dimethylformamide dimethyl acetal, the solvent is 2-methyltetrahydrofuran, the reaction proceeds at about 40° C., the acid is trifluoroacetic acid, Hal is —F and n=3.

M. Formation of F-1 from D-1 Through E-1

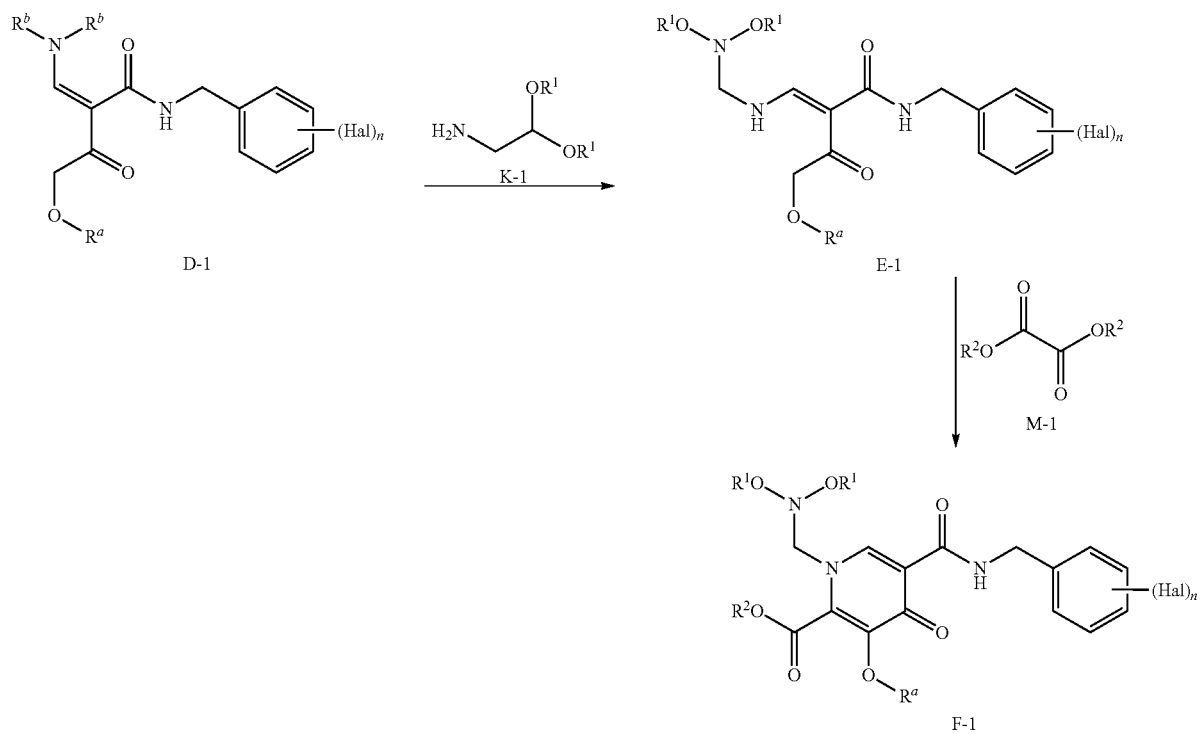

To a solution of D-1 in a solvent, is added about 1.1 equivalent of K-1 under conditions effective to produce E-1.

In certain embodiments, the solvent is an alcoholic solvent such as, but not limited to ethanol, n-propanol, 2-propanol, butanol, methanol and tert-butanol, or an aprotic polar organic solvents such as, but not limited to 2-methyl tetrahydrofuran, tetrahydrofuran, acetone, acetonitrile, N,N-dimethylformamide, N,N-dimethylacetamide, 1,4-dioxane, and N-methyl-2-pyrrolidinone. In particular embodiments, the solvent is methanol.

In certain embodiments, K-1 is an aminoacetaldehyde acetal such as, but not limited to, aminoacetaldehyde diethylacetal, aminoacetaldehyde dipropylacetal, Aminoacetaldehyde dimethylacetal, and aminoacetaldehyde dibutalacetal. In certain embodiments, K-1 is aminoacetaldehyde dimethylacetal.

In certain embodiments, the reaction proceeds at about 10 to 60° C., about 10 to 50° C., about 10 to 40° C., about 10 to 30° C., about 10 to 20° C., 20 to 60° C., about 20 to 50° C., about 20 to 40° C., about 20 to 30° C., about 30 to 60° C., about 30 to 50° C., about 30 to 40° C., about 40 to 60° C., about 40 to 50° C., about 50 to 60° C., or any subrange therebetween. In particular embodiments, the reaction proceeds at room temperature. In further embodiments, the reaction proceeds at about 16° C. to about 23° C.

In certain embodiments, the reaction is stirred for about 0.1 to about 12 hours, about 0.5 to about 4 hours, about 1 to about 2 hours.

Once the reaction has progressed sufficiently to produce E-1, M-1 is added to the reaction mixture.

In certain embodiments, about 1 to about 10 or about 1 to about 5 equivalents of M-1 is added. In a particular embodiment, about 5 equivalents of M-1 is added.

In certain embodiments, M-1 is dimethyl oxalate, diethyl oxalate, dipropyl oxalate, or dibutyl oxalate. In a particular embodiment, M-1 is dimethyl oxalate.

The reaction mixture is stirred at a temperature sufficient to achieve dissolution of M-1. In certain embodiments, the reaction mixture is stirred at about 20-80° C., at about 20-70° C., at about 20-60° C., at about 30-60° C., at about 40-50° C. or at about 45° C.

In certain embodiments, a base is added to the reaction mixture following the addition of M-1.

In certain embodiments, the base is a metal hydride, an alkoxide, an inorganic carbonate, or a bis(trialkylsilyl) amide. In certain embodiments, the base is a metal hydride. In certain embodiments, the base is an alkoxide. In certain embodiments, the base is an inorganic carbonate. In certain embodiments, the base is a bis(trialkylsilyl) amide. Exemplary metal hydrides include, but are not limited to lithium hydride, sodium hydride, and potassium hydride. Exemplary alkoxides include, but are not limited to, sodium methoxide, sodium tert-butoxide, sodium ethoxide, potassium tert-butoxide, potassium ethoxide, sodium tert-pentoxide, and lithium tert-butoxide. Exemplary bis(trialkylsilyl) amide bases include, but are not limited to lithium bis(trimethylsilyl)amide, sodium bis(trimethylsilyl)amide, and potassium bis(trimethylsilyl)amide. Exemplary carbonates include, but are not limited to lithium, sodium, potassium, and cesium carbonate.

In still further embodiments, the base is a mixture of at least one of the foregoing bases. In certain embodiments, the base is a mixture of up to three, or up to two, metal hydrides. In certain embodiments, the base is a mixture of up to three, or up to two, alkoxides. In certain embodiments, the base is a mixture of up to three, or up to two, metal bis(trialkylsilyl) amides. In certain embodiments, the base is a mixture of up to three, or up to two, of the following bases: lithium hydride, sodium hydride, potassium hydride, sodium methoxide, sodium tert-butoxide, sodium ethoxide, potassium tert-butoxide, potassium ethoxide, sodium tert-pentoxide, lithium tert-butoxide, lithium bis(trimethylsilyl)amide, sodium bis(trimethylsilyl)amide, and potassium bis(trimethylsilyl)amide.

In particular embodiments, the base is sodium methoxide. In particular embodiments, the base is sodium methoxide in solution in methanol.

In certain embodiments, after the addition of the base, the reaction is heated to about 20 to 80° C., 20 to 70° C., about 20 to 60° C., about 20 to 50° C., about 20 to 40° C., about 20 to 30° C., about 30 to 80° C., about 30 to 70° C., about 30 to 60° C., about 30 to 50° C., about 30 to 40° C., about 40 to 80° C., about 40 to 70° C., about 40 to 60° C., about 40 to 50° C., about 50 to 80° C., about 50 to 70° C., about 50 to 60° C., about 60 to 80° C., about 60 to 70° C., about 70 to 80° C., or any subrange therebetween. In a particular embodiment, the reaction is heated to about 42 to 48° C. In a particular embodiment, the reaction is heated to about 45° C.

In certain embodiments, the reaction is stirred for about 1 to about 24 hours, about 6 to about 24 hours, about 12 to about 20 hours, about 14 to about 18 hours.

In certain embodiments, the reaction is diluted with an aqueous solution and F-1 is extracted and purified by any suitable methods known in the art, including but not limited to solvent extraction, crystallization, and silica gel chromatography.

In certain embodiments, the temperature is reduced to about 34-37° C. over the course of about 1 hour, optionally charged with F-1 seed crystals and allowed to age for about 1-2 hours. At this point, water is added and temperature is reduced to about 18-22° C. over 1 hour. The resulting slurry is filtered.

In certain embodiments, liquors are recycled to displace solids remaining in the reactor. The collected solids on the filter are then washed with a 1:1 mixture of water and methanol, followed by water. The collected wet cake is dried in a vacuum oven at about 36-42° C. for about 16 hours, providing F-1.

In certain embodiments, $R^1$ is $(C_1-C_4)$alkyl, $(C_6-C_{10})$aryl, or $(C_6-C_{10})$aryl $(C_1-C_4)$alkyl. In certain embodiments, $R^1$ is $C_1-C_4$alkyl. In further embodiments $R^1$ is —$CH_3$, that is, K-1 is aminoacetaldehyde dimethyl acetal.

In certain embodiments, $R^2$ is $(C_1-C_4)$alkyl, $(C_6-C_{10})$aryl, or $(C_0-C_{10})$aryl $(C_1-C_4)$alkyl. In certain embodiments, $R^2$ is $C_1-C_4$alkyl. In certain embodiments, $R^2$ is —$CH_3$.

In particular embodiments, each Hal is independently —F or —Cl. In a particular embodiment, Hal is —F In certain embodiments, n=1-3. In certain embodiments, n=2. In certain embodiments, n=3.

In certain embodiments, $R^a$ is $(C_1-C_4)$alkyl, $(C_6-C_{10})$aryl, or $(C_6-C_{10})$aryl$(C_1C_4)$alkyl. In certain embodiments, $R^a$ is $(C_1-C_4)$alkyl. In certain embodiments, $R^a$ is methyl.

In certain embodiments, each $R^b$ is independently $(C_1-C_4)$alkyl, $(C_6-C_{10})$aryl, or $(C_6-C_{10})$aryl$(C_1C_4)$alkyl. In certain embodiments, each $R^b$ is independently $(C_1-C_4)$alkyl. In certain embodiments, $R^b$ is methyl.

In particular embodiments, $R^b$ is methyl, $R^a$ is $(C_1-C_4)$ alkyl, each Hal is —F, n=3, $R^2$ is $(C_1-C_4)$alkyl, $R^1$ is $(C_1-C_4)$alkyl, the solvent is an alcoholic solvent, K-1 is aminoacetaldehyde dimethylacetal, the first reaction proceeds at about 2 to about 40° C., the second reaction is heated to about 20 to about 80° C., the base is n alkoxide, and M-1 is dimethyl oxalate In particular embodiments, $R^b$ is methyl, $R^a$ is methyl, Hal is —F, n=3, $R^2$ is —$CH_3$, $R^1$ is —$CH_3$, the solvent is methanol, K-1 is aminoacetaldehyde dimethylacetal, the first reaction proceeds at about 16 to about 23° C., the second reaction is heated to about 45° C., the base is sodium methoxide, and M-1 is dimethyl oxalate N. Acetal Hydrolysis of F-1 to Form FF-1

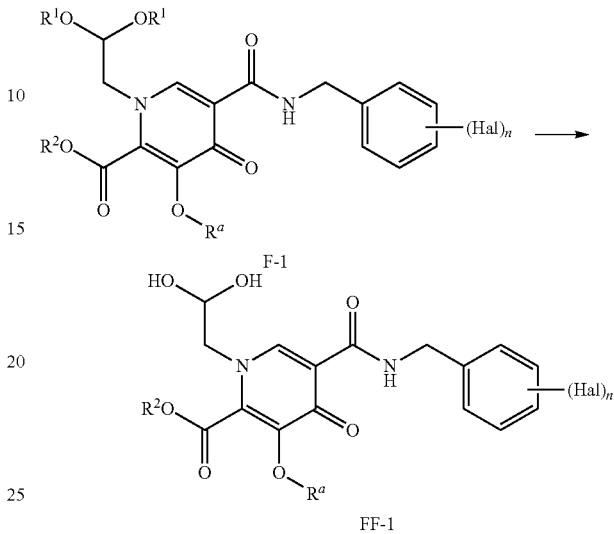

To a solution of F-1 in a solvent, is added about 0.1 to 1 equivalent of a first acid and about 2 to 20 equivalents of a second acid under conditions effective to produce FF-1.

In some embodiments, about 0.1 to 0.5 equivalent of the first acid is added. In particular embodiments, about 0.1 equivalent of the first acid is added.

In some embodiments, the solvent is a polar organic solvent or a weak protic acid. In some embodiments, the polar organic solvent include, but is not limited to propionitrile, tetrahydroduran, 1,4-dioxane, acetonitrile and ethyl acetate. In some embodiments, the weak protic acid include, but is not limited to formic acid, propionic acid and butyric acid. In a particular embodiment, the solvent is acetonitrile.

In some embodiments, the first acid is a strong protic acid including, but not limited to methanesulfonic acid, sulfuric acid, hydrochloric acid, trifluoroacetic acid, p-Toluenesulfonic acid and camphorsulfonic acid.

In a particular embodiment, the first acid is p-Toluenesulfonic acid. In a particular embodiment, the first acid is p-Toluenesulfonic acid monohydrate.

In some embodiments, the second acid is a weak protic acid including, but not limited to acetic acid, formic acid, propionic acid and butyric acid. In a particular embodiment, the second acid is acetic acid.

The reaction is then heated to about 20 to 120° C., about 40 to 100° C., about 60 to 80° C., or about 70 to 80° C. In a particular embodiment, the reaction is heated to about 75° C.

In certain embodiments, the reaction is stirred for about 1 to about 24 hours, for about 4 to about 14 hours, for about 8 to about 10 hours.

In certain embodiments, water is added to the reaction mixture.

In certain embodiments, the product formed is extracted and optionally purified by any suitable technique known in the art, such as, but not limited to solvent extraction, chromatography, crystallization or a combination thereof.

In certain embodiments, the mixture is concentrated under reduced pressure to remove the solvent. The resultant slurry is then aged at room temperature for about 2 hours, filtered and washed with water. The cake is dried in a vacuum oven at 50° C. for at least 10 hours to give FF-1.

In certain embodiments, $R^1$ is $(C_1-C_4)$alkyl, $(C_6-C_{10})$aryl, or $(C_6-C_{10})$aryl $(C_1-C_4)$alkyl. In certain embodiments, $R^1$ is $C_1-C_4$alkyl. In further embodiments $R^1$ is —$CH_3$.

In certain embodiments, $R^2$ is $(C_1-C_4)$alkyl, $(C_6-C_{10})$aryl, or $(C_6-C_{10})$aryl $(C_1-C_4)$alkyl. In certain embodiments, $R^2$ is $C_1-C_4$alkyl. In certain embodiments, $R^2$ is —$CH_3$.

In particular embodiments, each Hal is independently —F or —Cl. In a particular embodiment, Hal is —F In certain embodiments, n=1-3. In certain embodiments, n=2. In certain embodiments, n=3.

In certain embodiments, $R^a$ is $(C_1-C_4)$alkyl, $(C_6-C_{10})$aryl, or $(C_6-C_{10})$aryl$(C_1C_4)$alkyl. In certain embodiments, $R^a$ is $(C_1-C_4)$alkyl. In certain embodiments, $R^a$ is methyl.

In particular embodiments, $R^a$ is $(C_1-C_4)$alkyl, each Hal is —F, n=3, $R^2$ is $(C_1-C_4)$alkyl, $R^1$ is $(C_1-C_4)$alkyl, the reaction is heated to about 20 to about 120° C., the first acid is p-Toluenesulfonic acid, the second acid is acetic acid, and the solvent is acetonitrile.

In particular embodiments, $R^a$ is methyl, Hal is —F, n=3, $R^2$ is —$CH_3$, $R^1$ is —$CH_3$, the reaction is heated to about 75° C., the first acid is p-Toluenesulfonic acid, the second acid is acetic acid, and the solvent is acetonitrile.

O. Cyclization of FF-1 and N-1 to Form G-1

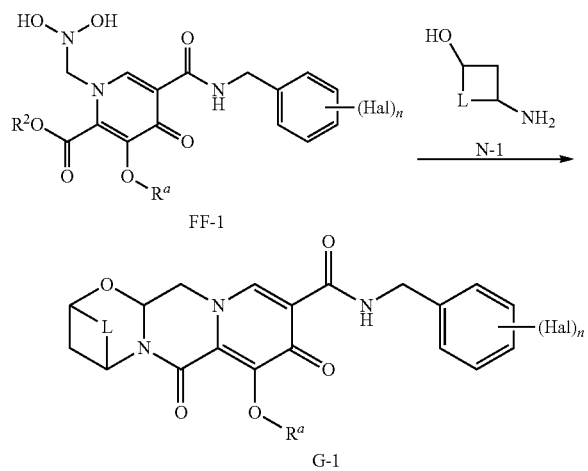

The starting material FF-1, N-1, or a salt or co-crystal thereof, and an additive are combined with a solvent under conditions effective to produce G-1.

In certain embodiments, the additive is a carboxylate salt such as, but not limited to sodium acetate, potassium acetate, lithium acetate, sodium propionate, and potassium propionate. In certain embodiments, the additive is a carbonate such as, but not limited to sodium carbonate, potassium carbonate, lithium carbonate, and cesium carbonate. In certain embodiments, the additive is a water scavenger such as but not limited to molecular sieves, trimethyl orthoacetate, and trimethyl orthoformate. In particular embodiments, the additive is potassium acetate.

In certain embodiments, about 1 to about 2 or about 1 to about 1.5 equivalents of N-1 or a salt or co-crystal thereof, is used.

In certain embodiments, about 1 to about 5 equivalents of additive are used. In particular embodiments, about 2.5 equivalents of additive is added.

In certain embodiments, the solvent is acetonitrile, ethyl acetate, toluene, 2-methyl tetrahydrofuran, isopropyl acetate, dichloromethane, or a mixture thereof. In particular embodiments, the solvent is dichloromethane.

In certain embodiments, the reaction is stirred at about 0 to about 40° C., about 10 to about 30° C., about 15 to about 25° C., about 20° C.

In certain embodiments, G-1 is extracted and optionally purified by any suitable technique known in the art, such as, but not limited to solvent extraction, chromatography, crystallization or a combination thereof.

In particular embodiments, the reaction mixture is washed with an aqueous solution and evaporated to dryness. In particular embodiments, the residue is dissolved in dimethylformamide and the resulting solution is added to water over about 2 hours, while agitating. The product slurry is aged at about 20° C. for about 12 hours and filtered. The product cake is washed with water and dried to afford G-1.

In certain embodiments, N-1 is in solution when added to the reaction mixture.

In further embodiments, L is —$CH_2$—$CH_2$—.

In particular embodiments, N-1 is (1R,3S)-3-aminocyclopentan-1-ol:

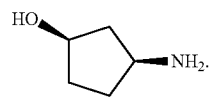

In particular embodiments, N-1 is a free base or is synthesized and used without isolation.

In particular embodiments, N-1 is a salt or co-crystal. Suitable salts or co-crystals of N-1 include, but are not limited to, benzoic acid, acetic acid, fumaric acid, methanesulfonic acid, p-toluenesulfonic acid, oxalic acid, hydrochloric acid, naproxen, S-naproxen, R-naproxen, mandelic acid, R-mandelic acid, and S-mandelic acid.

In still further embodiments, N-1 is

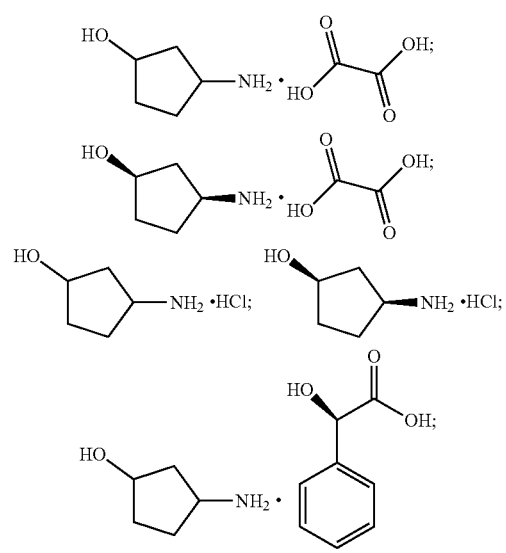

-continued

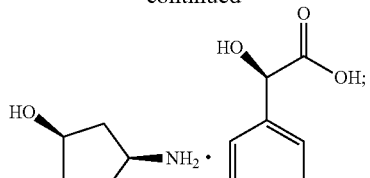

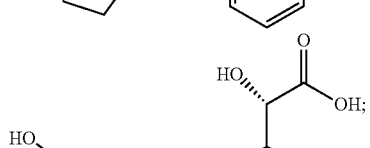

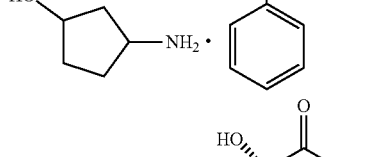

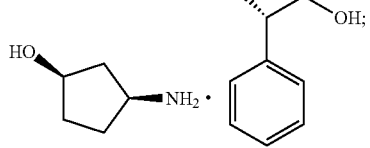

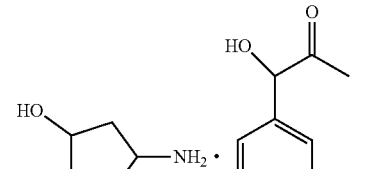

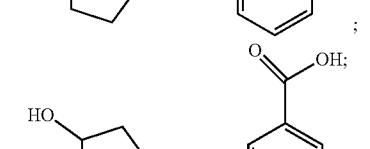

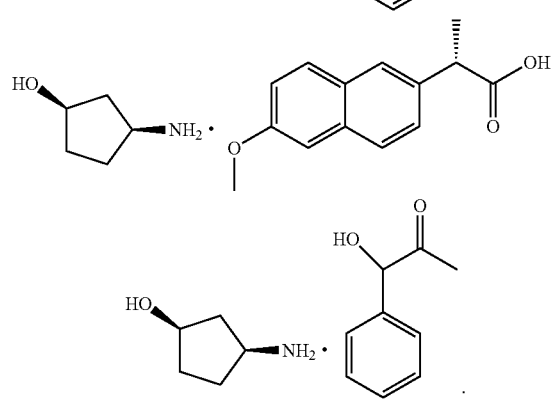

In particular embodiments, N-1 is a salt or co-crystal with benzoic acid.

In particular embodiments, N-1 is

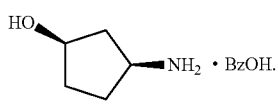

In particular embodiments, each Hal is independently —F or —Cl. In a particular embodiment, each Hal is —F In certain embodiments, n=1-3. In certain embodiments, n=2. In certain embodiments, n=3.

In certain embodiments, $R^2$ is $(C_1-C_4)$alkyl, $(C_6-C_{10})$aryl, or $(C_6-C_{10})$aryl $(C_1-C_4)$alkyl. In certain embodiments, $R^2$ is $C_1-C_4$alkyl. In certain embodiments, $R^2$ is —$CH_3$.

In certain embodiments, $R^a$ is $(C_1-C_4)$alkyl, $(C_6-C_{10})$aryl, or $(C_6-C_{10})$aryl$(C_1C_4)$alkyl. In certain embodiments, $R^a$ is $(C_1-C_4)$alkyl. In certain embodiments, $R^a$ is methyl.

In particular embodiments, $R^a$ is $(C_1-C_4)$alkyl, each Hal is —F, n=3, $R^2$ is —$CH_3$, N-1 is

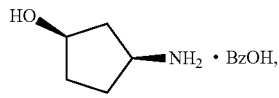

the solvent is dichloromethane, the reaction is stirred at about 0 to about 40° C. and the additive is potassium acetate.

In particular embodiments, $R^a$ is methyl, Hal is —F, n=3, $R^2$ is —$CH_3$, N-1 is

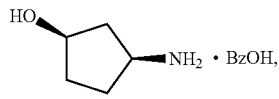

the solvent is dichloromethane, the reaction is stirred at about 20° C. and the additive is potassium acetate.

P. Conversion of (−)-Vince Lactam to b-1 Through a-1

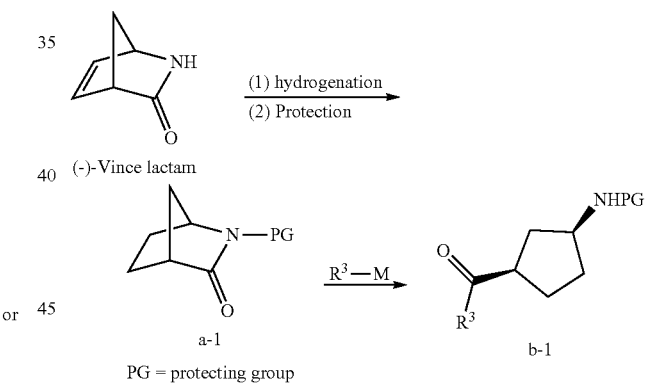

PG = protecting group

A catalyst, a solvent and (−)-Vince lactam are stirred in a reactor, which is purged with an inert gas. A source of hydrogen is added.

In certain embodiments, the hydrogen source is formic acid, hydrazine, dihydronapthalene, dihydroanthracene, hydrogen gas, or Hantzch ester and isopropanol. In particular embodiments, the hydrogen source is hydrogen gas.

In certain embodiments, the catalyst is a platinum catalyst such as $PtO_2$, a nickel catalyst such as Raney Nickel, a rhodium catalyst such as $RhCl(PPh_3)_3$, a palladium catalyst, a ruthenium catalyst such as Nyori's catalyst or an iridium catalyst such as Crabtree's catalyst. In some embodiments, the catalyst is selected form the group consisting of Pd/C, $PtO_2$, Raney Nickel, $RhCl(PPh_3)_3$, Nyori's catalyst, and Crabtree's catalyst. In particular embodiments, the catalyst is Pd/C.

In certain embodiments, the solvent is a polar aprotic solvent such as THF, 2-MeTHF, dioxane, diethyl ether, diisopropyl ether, DME, MTBE, CPME, EtOAc, and DCM. In certain embodiments, the solvent is a polar protic solvent such as methanol, ethanol, n-butanol, and isopropanol. In particular embodiments, the solvent is 2-methyltetrahydrofuran.

In certain embodiments, the reaction is stirred at about 0 to 65° C., about 10 to 55° C., about 15 to 45° C., about 20 to 40° C., about 25 to 35° C.

In certain embodiments, the reactor is maintained at about 0.30 to about 0.35 MPa.

In certain embodiments, the reaction takes place over about 1 to about 24 hours, about 1 to about 12 hours, about 3 to about 9 hours, about 6.5 hours.

In certain embodiments, the product formed is extracted and optionally purified by any suitable technique known in the art, such as, but not limited to solvent extraction, chromatography, crystallization or a combination thereof.

In certain embodiments, the reaction is filtered through celite washed with 2-MeTHF to yield the hydrogenated product in solution.

In certain embodiments, to a solution of the hydrogenated product, a second catalyst is added, as well as an activated source for a protecting group.

In certain embodiments, the second catalyst is a nucleophilic amine-containing compound such as imidazole, derivatives of 4-dimethylaminopyridine, 1,4-diazabicyclo[2.2.2]octane, 1,8-diazabicyclo[5.4.0]undec-7-ene, and pyridine, or a nucleophilic phosphine containing compound such as triphenylphosphine. In particular embodiments, the second catalyst is 4-dimethylaminopyridine (DMAP).

In certain embodiments, the activated source of protecting group is $Boc_2O$. In particular embodiments, $Boc_2O$ is prepared in solution in 2-MeTHF.

In certain embodiments, the protecting group is Boc.

In certain embodiments, the reaction occurs in a polar aprotic solvent such as THF, EtOAc, DCM, acetonitrile or 2-MeTHF. In particular embodiments, the reaction occurs in 2-MeTHF.

In certain embodiments, the reaction occurs at temperatures in the range from about 20 to 80° C., about 25 to 70° C., about 35 to 60° C., about 45 to 50° C.

In certain embodiments, the reaction occurs for about 0.5 to about 12 hours, about 1 to about 6 hours, about 1 to about 3 hours, about 2 hours.

In certain embodiments, the product formed is extracted and optionally purified by any suitable technique known in the art, such as, but not limited to solvent extraction, chromatography, crystallization or a combination thereof.

In certain embodiments, the solution is concentrated and a second solvent is added.

In certain embodiments, the second solvent is a polar aprotic solvent such as THF, Dioxane, DME, diisopropyl ether, diethyl ether, MTBE, CPME, 2-MeTHF and toluene. In particular embodiments, the second solvent is 2-MeTHF.

In certain embodiments, the solution is maintained at about −50 to 30° C., about −50 to 30° C., about −30 to 20° C., about −20 to 10° C., about −10 to 0° C.

Following hydrogenation and addition of the protecting group PG, a nucleophile $R^3M$ is added to the reaction mixture.

In certain embodiments, nucleophile $R^3M$ is a n-alkyl Grignard reagent such as ethylmagnesium halides, n-propylmagnesium halides, and n-butylmagnesium halides or an organolithium reagent such as methyl lithium, n-butyllithium, and n-hexyllithium. In particular embodiments, the nucleophile is methyl magnesium bromide.

In certain embodiments, nucleophile $R^3M$ is added, while maintaining the reaction within the desired temperature range, over about 1 to about 12 hours, about 3 to about 9 hours, about 5 to about 7 hours, about 6 hours. After the addition is complete, the mixture is stirred for an additional about 0.5 to about 12 hours, about 0.5 to about 6 hours, about 0.5 to about 4 hours, about 1 to about 2 hours.

In certain embodiments, the product formed is extracted and optionally purified by any suitable technique known in the art, such as, but not limited to solvent extraction, chromatography, crystallization or a combination thereof.

In certain embodiments, following addition of nucleophile $R^3M$, 15% aqueous AcOH is added while maintaining the temperature at about 0 to 5° C. to adjust the pH to approximately 7. The layers are separated and the organic layer is washed with water twice. The organic layer is concentrated to 4 to 5 Volumes under reduced pressure at about ≤45° C. The solution is azeotroped with 2-MeTHF. The final solution is concentrated under reduced pressure to about 2.5 to 3 Volumes and n-Heptane is slowly added while maintaining the temperature at 30 to 35° C. In certain embodiments, b-1 seeds are added and the mixture is stirred at about 30 to 35° C. for about 5 to 10 hours.

In certain embodiments, additional n-heptane is added while maintaining the temperature at 30 to 35° C. over approximately 5 h. The contents are cooled to −5 to 0° C. and held for approximately 1 to 2 hours. The product is collected by filtration, washed with n-heptane at −5 to 0° C., and dried under reduced pressure at 40 to 45° C. to afford b-1.

In particular embodiments, the hydrogen source is hydrogen gas, the catalyst is a palladium catalyst, the solvent for the hydrogenation is 2-methyltetrahydrofuran, the hydrogenation reaction is stirred at about 0 to about 65° C., the second catalyst is a nucleophilic amine-containing compound, the activated source of protecting group is $Boc_2O$, the protection reaction occurs in 2-MeTHF at about 25 to 70° C., the second solvent is 2-MeTHF, and the nucleophile is methyl magnesium bromide.

In particular embodiments, the hydrogen source is hydrogen gas, the catalyst is Pd/C, the solvent for the hydrogenation is 2-methyltetrahydrofuran, the hydrogenation reaction is stirred at about 25 to 35° C., the second catalyst is 4-Dimethylaminopyridine, the activated source of protecting group is $Boc_2O$, the protection reaction occurs in 2-MeTHF at about 45 to 50° C., the second solvent is 2-MeTHF, and the nucleophile is methyl magnesium bromide.

Q. Conversion of b-1 to c-1

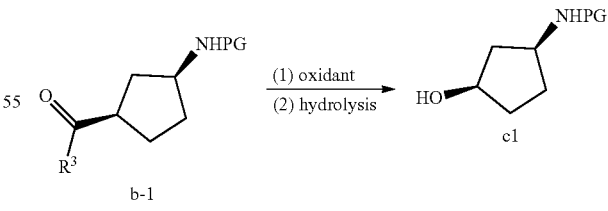

To a solution of b-1 in a solvent, an oxidant is added and the reaction is stirred.

In certain embodiments, PG is a protecting group. In certain embodiments, the protecting group PG is Boc.

In certain embodiments, the solvent is a polar aprotic solvent such as DCM, 1,2-dichloroethane, toluene, chlorobenzene, dichlorobenzene, chloroform, carbon tetrachloride and DMF, or a polar protic solvent such as water, acetic acid, methanol, and ethanol. In particular embodiments, the solvent is toluene.

In certain embodiments, the oxidant is hydrogen peroxide, oxone, t-butyl hydrogen peroxide, trifluoroperacetic acid (TFPAA), nitroperbenzoic acid, monopermaleic acid (MPMA), monoperphthalic acid, monoperphthalic acid magnesium salt, persulfuric acid, performic acid, peracetic acid, perbenzoic acid, a silylated peracid, benzeneperoxyseleninic acid, sodium perborate, meta-chloroperoxybenzoic acid, or a resin-bound peracid. In particular embodiments, the oxidant is meta-chloroperoxybenzoic acid (mCPBA).

In certain embodiments, mCPBA is added in several portions every 4 to 6 h.

In certain embodiments, the reaction is stirred within the temperature range of −10 to 50° C., 0 to 40° C., 10 to 45° C., 15 to 40° C., 20 to 35° C., 25 to 30° C.

In certain embodiments, the reaction is stirred for 1 to 48 h, 6 to 36 h, 10 to 20 h.

In certain embodiments, the product formed is extracted and optionally purified by any suitable technique known in the art, such as, but not limited to solvent extraction, chromatography, crystallization or a combination thereof.

In particular embodiments, 20% $NaHSO_3$ is added, then 10% NaOH is added. The organic layer is washed with water and concentrated to afford the oxidized product in solution.

To a solution of the oxidized product, is added water, a solvent and a base or an acid.

In certain embodiments, the solvent is a polar protic solvent such as methanol, ethanol, isopropanol or water, or a combination of at least one polar aprotic solvent with a polar aprotic solvent such as THF, Dioxane, DME, disopropylether, diethyl ether, MTBE, CPME, or toluene. In particular embodiments, the solvent is a combination of toluene, methanol, and water.

In certain embodiments, the base is an hydroxide base such as lithium hydroxide, sodium hydroxide and potassium hydroxide or a silanolate base such as sodium trimethylsilanolate and potassium trimethylsilanolate. In particular embodiments, the base is lithium hydroxide.

In certain embodiments, the acid is a concentrated strong acid such as sulfuric and hydrochloric acid.

In certain embodiments, the reaction is stirred at about 0 to 80° C., about 5 to 70° C., about 10 to 60° C., about 15 to 50° C., about 20 to 40° C., about 25 to 30° C.

In certain embodiments, the product formed is extracted and optionally purified by any suitable technique known in the art, such as, but not limited to solvent extraction, chromatography, crystallization or a combination thereof.

In particular embodiments, toluene and 25% NaCl are added and the layers separated. The organic layer is washed with a solution of 20% NaCl adjusted to about pH 7 to about pH 8 with 1 N HCl. The organic layer is filtered and concentrated. Toluene is added and the distillation continued. Toluene and active carbon are added. The mixture is warmed to about 30 to about 40° C. and stirred for about 2 to 6 h. The contents are cooled, filtered through celite and washed with toluene. The filtrate is concentrated. n-heptane is added over about 1 to 2 hours and the mixture is optionally seeded with c-1 and stirred for an additional approximately 2 to 3 hours. n-heptane is added and the mixture is stirred for about 2 to 3 h. The mixture is cooled to about 10 to 15° C. and stirred for an additional approximately 3 to 5 h. The product is collected by filtration and washed with n-heptane at about 10 to 15° C. The product is dried to afford c-1.

In particular embodiments, the protecting group PG is Boc, the solvent is a polar aprotic solvent, the oxidant is mCPBA, the reaction is stirred at 10 to 45° C., the hydrolysis occurs in a combination of toluene, methanol, and water at about 10 to 60° C., and the base is an hydroxide base.

In particular embodiments, the protecting group PG is Boc, the solvent is toluene, the oxidant is mCPBA, the reaction is stirred at 25 to 30° C., the hydrolysis occurs in a combination of toluene, methanol, and water at about 25 to 30° C., and the base is lithium hydroxide.

R. Resolution of c-1a—Selective Acylation

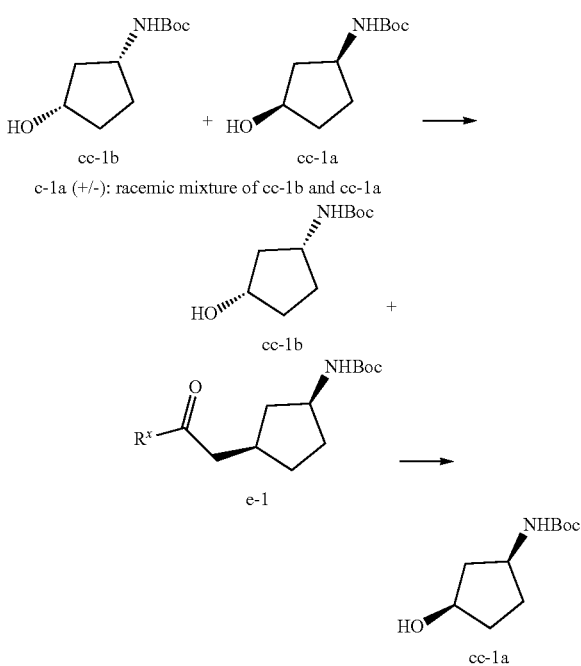

In certain embodiments, enantioenriched cc-1a is obtained through enzymatically catalyzed selective acylation.

In this process, the racemic starting material c-1a is a mixture of cc-1b and cc-1a (i.e., c-1a (+/−) and is dissolved in a solvent.

In certain embodiments, the solvent is a polar aprotic solvent, a non-polar solvent, a polar protic solvent, a mixture of organic solvents with aqueous buffers or a mixture thereof. Exemplary polar aprotic solvents include but are not limited to diethyl ether, diisopropyl ether, methyl t-butyl ether, 2-methyltetrahydrofuran, tetrahydrofuran, dichloromethane and chloroform. Exemplary non-polar solvents include but are not limited to toluene, hexane and heptane. Exemplary polar protic solvents include but are not limited to t-butanol. In particular embodiments, the solvent used is toluene.

Once the racemic starting material c-1a is dissolved in the solvent, about 1 equivalent of an acyl donor is added. In certain embodiments, the acyl donor is an anhydride or an ester. In certain embodiments, the anhydride include but is not limited to glutaric anhydride and acetic anhydride. In certain embodiments, the ester include but is not limited to vinyl acetate, isopropenyl acetate, 4-chlorophenyl acetate and ethyl methoxy acetate. In particular embodiments, the acyl donor is glutaric anhydride.

In certain embodiments, $R^x$ is $(C_1-C_6)$alkyl-$R^y$ and $R^y$ is selected from the group consisting of H, CN, —$NR^{z1}R^{z2}$, $C(O)R^{z1}$, —$C(O)OR^{z1}$, —$C(O)NR^{z1}R^{z2}$, —$OC(O)NR^{z1}R^{z2}$, —NR$^{z1}$C(O)R$^{z2}$, —NR$^{z1}$C(O)NR$^{z2}$, —NR$^{z1}$C(O)OR$^{z2}$, —S(O)$_{1-2}$R$^{z1}$, —S(O)$_2$NR$^{z1}$R$^{z2}$, —NR$^{z1}$S(O)$_2$R$^{z2}$, NR$^{z1}$S(O)$_2$R$^{z2}$, and OR$^{z1}$.

In certain embodiments, R$^{z1}$ and R$^{z2}$ are independently selected from the group consisting of H, C$_{1-6}$alkyl, C$_{2-6}$ alkenyl, C$_{2-6}$ alkynyl, C$_{1-6}$heteroalkyl, C$_{3-10}$ cycloalkyl, 3 to 12 membered heterocyclyl, C$_{6-10}$ aryl and 5 to 10 membered heteroaryl.

In certain embodiments, R$^x$ is (C$_1$-C$_4$)alkyl-R$^y$ and R$^y$ is selected from the group consisting of H and CO$_2$H.

In certain embodiments, R$^x$ is methyl or (CH$_2$)$_3$—CO$_2$H. In certain embodiments, R$^x$ is (CH$_2$)$_3$—CO$_2$H.

About 15% by weight of an enzyme is added. In certain embodiments, the enzyme is a lipase. In certain embodiments, the lipase includes but is not limited to Novozyme 435, CAL-A, CAL-B, PPL, PSL-C, PSL, CRL and MML. In certain embodiments, the lipase includes but is not limited to CAL-A, CAL-B, PPL, PSL-C, PSL, CRL and MML. In particular embodiments, the enzyme used is Novozyme 435.

In certain embodiments, the reaction is allowed to stir for about 1 to 48 h for about 6 to 48 h, for about 12 to 30 h, for about 20 to 26 h, for about 23 h.

In certain embodiments, the reaction is allowed to stir at about 0 to 60° C. at about 5 to 30° C., at about 10 to 15° C.

In certain embodiments, additional enzyme is added and the reaction is allowed to proceed for about 1 to 48 h at about 0 to 60° C. In certain embodiments, about 5% by weight of additional enzyme is added and the reaction is allowed to proceed for about 6 to 24 h at about 5 to 30° C. In particular embodiments, additional enzyme is added and the reaction is allowed to proceed for about 12 h at about 10 to 15° C.

In certain embodiments, the ester formed e-1 is extracted and optionally purified by any suitable technique known in the art, such as, but not limited to solvent extraction, chromatography, crystallization or a combination thereof.

In certain embodiments, precipitated enzyme solids are removed by filtration and rinsed with solvent. The desired e-1 is extracted into a basic aqueous layer such as aqueous Na$_2$CO$_3$. The aqueous is washed with an organic solvent (such as MTBE) to remove undesired material. A solvent (such as THF) is then added to the aqueous layer, which contains e-1, followed by hydroxide.

In certain embodiments, the solvent is a polar aprotic solvent. Exemplary polar aprotic solvent include but are not limited to diethyl ether, diisopropyl ether, methyl t-butyl ether, 2-methyltetrahydrofuran, tetrahydrofuran, dichloromethane and chloroform. In particular embodiments, the solvent is THF.

Exemplary sources of hydroxide include but are not limited to sodium hydroxide, potassium hydroxide and lithium hydroxide. In particular embodiments, the source of hydroxide is sodium hydroxide.

In certain embodiments, the mixture is allowed to stir for about 1 to 24 h at about 0 to 60° C. In certain embodiments, the mixture is allowed to stir for about 1 to 12 h at about 5 to 30° C. In particular embodiments, the mixture is allowed to stir for about 4 h at about 15 to 20° C.

In certain embodiments, the product cc-1a is extracted and optionally purified by any suitable technique known in the art, such as, but not limited to solvent extraction, chromatography, crystallization or a combination thereof.

In particular embodiments, the layers are separated, and the organic layer is concentrated.

In certain embodiments, the organic phase is concentrated and cc-1a is recrystallized in a solvent with the addition of seeds of cc-1a. In certain embodiments, the solvent is a mixture of THF, dichloromethane and water, and the recrystallization is conducted at about 40 to 50° C.

In certain embodiments, the enantiomeric excess (% ee) of the product is about 50 to 100, about 75 to 100, about 90 to 100, about 95 to 100, about 98 to 100, about 98.5 to 100, about 98.5 to 99, about 99 to 100, about 99.5 to 100, about 99.9 to 100.

In particular embodiments, c-1a is dissolved in a nonpolar solvent, the acyl donor is glutaric anhydride, R$^x$ is (CH$_2$)$_3$—CO$_2$H, the enzyme used is a lipase, the reaction is stirred at about 10 to 15° C., cc-1 b is removed by filtration, the hydrolysis occurs in THF at about 5 to 30° C., and the source of hydroxide is sodium hydroxide.

In particular embodiments, c-1a is dissolved in toluene, the acyl donor is glutaric anhydride, R$^x$ is (CH$_2$)$_3$—CO$_2$H, the enzyme used is Novozyme 435, the reaction is stirred at about 10 to 15° C., cc-1b is removed by filtration, the hydrolysis occurs in THF at about 15 to 20° C., and the source of hydroxide is sodium hydroxide.

S. Resolution of c-1a—Selective Hydrolysis

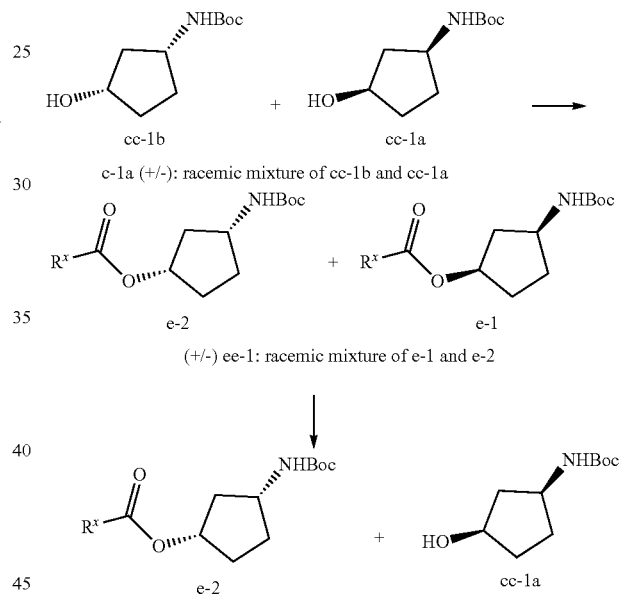

In certain embodiments, enantioenriched cc-1a is obtained through enzymatically catalyzed selective hydrolysis.

A mixture of the starting material, c-1a, an acyl donor, a base and a catalyst in a solvent, is stirred.

In certain embodiments, the acyl donor includes but is not limited to an anhydride or an acid chloride. In certain embodiments, the anhydride includes but is not limited to succinic anhydride and acetic anhydride. In certain embodiments, the acid chloride include but is not limited to acetyl chloride and benzoyl chloride. In particular embodiments, the acyl donor is glutaric anhydride.

In certain embodiments, R$^x$ is (C$_1$-C$_6$)alkyl-R$^y$ and R$^y$ is selected from the group consisting of H, CN, —NR$^{z1}$R$^{z2}$C(O)R$^{z1}$, —C(O)OR$^{z1}$, —C(O)NR$^{z1}$R$^{z2}$, —OC(O)NR$^{z1}$R$^{z2}$, —NR$^{z1}$C(O)R$^{z2}$, —NR$^{z1}$C(O)NR$^{z2}$, —NR$^{z1}$C(O)OR$^{z2}$, —SR$^{z1}$, —S(O)$_{1-2}$R$^{z1}$, —S(O)$_2$NR$^{z1}$R$^{7-2}$, —NR$^{z1}$S(O)$_2$R$^{z2}$, NR$^{z1}$S(O)$_2$R$^{z2}$, and OR$^{z1}$.

In certain embodiments, R$^{z1}$ and R$^{z2}$ are independently selected from the group consisting of H, C$_{2-6}$ alkenyl, C$_{2-6}$ alkynyl, $C_{1-6}$heteroalkyl, $C_{3-10}$cycloalkyl, 3 to 12 membered heterocyclyl, $C_{6-10}$aryl and 5 to 10 membered heteroaryl.

In certain embodiments, $R^x$ is $(C_1-C_4)$alkyl-$R^y$ and $R^y$ is selected from the group consisting of H and $CO_2H$.

In certain embodiments, $R^x$ is methyl or $(CH_2)_3$—$CO_2H$. In certain embodiments, $R^x$ is $(CH_2)_3$—$CO_2H$.

In certain embodiments, the catalyst includes but is not limited to nucleophilic amine-containing compounds and nucleophilic phosphine containing compounds. In certain embodiments, the nucleophilic amine-containing compounds include but are not limited to imidazole, derivatives of 4-dimethylaminopyridine, 1,4-diazabicyclo[2.2.2]octane, 1,8-diazabicyclo[5.4.0]undec-7-ene, and pyridine. In certain embodiments, the nucleophilic phosphine containing compounds include but are not limited to triphenylphosphine. In particular embodiments, the catalyst is 4-dimethylaminopyridine.

In certain embodiments, the base includes but is not limited to amine bases, aromatic amine bases, inorganic carbonates, metal hydrides and alkoxides. In certain embodiments, the amine bases include but are not limited to N,N-diisopropylethylamine, quinuclidine, 1,4-diazabicyclo[2.2.2]octane, 1,8-diazabicyclo[5.4.0]undec-7-ene, tripropylamine, and tributylamine. In certain embodiments, the aromatic amine bases include but are not limited to pyridine. In certain embodiments, the inorganic carbonate bases include but are not limited to lithium carbonate, sodium carbonate, potassium carbonate, and cesium carbonate. In certain embodiments, the metal hydride bases include but are not limited to sodium hydride, and potassium hydride. In certain embodiments, the alkoxide bases include but are not limited to sodium methoxide, sodium tert-butoxide and lithium tert-butoxide. In particular embodiments, the base is pyridine.

In certain embodiments, the solvent is an aromatic solvent or a polar non-protic solvent. In certain embodiments, the aromatic solvent includes but is not limited to pyridine, toluene, xylene, benzene, and chlorobenzene. In certain embodiments, the polar non-protic solvent includes but is not limited to N,N-dimethylformamide, N,N-dimethylacetamide, 1,4-dioxane, N-methyl-2-pyrrolidinone, and dichloromethane. In particular embodiments, the solvent is Pyridine.

In certain embodiments, the reaction mixture is stirred for about 1 to 48 h, for about 6 to 24 h, for about 12 h.

In certain embodiments, the reaction mixture is stirred at about 0 to 120° C., at about 20 to 100° C., at about 40 to 80° C., or at about 60° C.

In certain embodiments, the product ee-1 is extracted and optionally purified by any suitable technique known in the art, such as, but not limited to solvent extraction, chromatography, crystallization or a combination thereof.

In particular embodiments, the reaction mixture is evaporated to dryness, dissolved in DCM and washed with a 0.2 M HCl aqueous solution. The organic layer is evaporated to dryness. The residue is stirred with water and the pH adjusted to about 7.8 with a 2 M NaOH solution. The water layer is washed with DCM. The water layer is then acidified to pH 4 with 3 N HCl aqueous solution and extracted DCM. The combined organic layers are dried over $Na_2SO_4$, filtered and evaporated. Trituration with pentane followed by filtration and drying under vacuum yields ee-1.

ee-1 is suspended in a solvent, an enzyme is added.

In certain embodiments, the solvent is a polar aprotic solvent, a non-polar solvent or a mixtures of organic solvents with aqueous buffers. In certain embodiments, the polar aprotic solvent includes but is not limited to diethyl ether, diisopropyl ether, methyl t-butyl ether, 2-methyltetrahydrofuran, tetrahydrofuran, dichloromethane, and chloroform. In certain embodiments, non-polar solvents include but are not limited to hexane and heptane. In particular embodiments, the solvent is diisopropyl ether:phosphate buffer 1:2.

In certain embodiments, the enzyme is a lipase such as but are not limited to CAL-A, CAL-B, PPL, PSL-C, PSL, CRL, and MML. In particular embodiments, the enzyme is CAL-B.

In certain embodiments, the reaction is stirred at 0 to 60° C., at 10 to 50° C., at 20 to 40° C., at about 30° C.

In certain embodiments, the reaction is stirred for 24 to 200 h, 50 to 150 h, about 100 h.

In certain embodiments, the product cc-1a is extracted and optionally purified by any suitable technique known in the art, such as, but not limited to solvent extraction, chromatography, crystallization or a combination thereof.

In certain embodiments, e-2 is removed by extraction with an aqueous layer. In certain embodiments, the product e-2 is removed by extraction in a basic aqueous layer.

In particular embodiments, the reaction mixture is filtered and the layers of the filtrate are separated. The solid is washed with DCM and the filtrate is used to extract the aqueous layer. The combined organic layers are washed with 5% $Na_2CO_3$, brine and dried. Filtration and evaporation of the volatiles under reduced pressure affords cc-1a.

In particular embodiments, the acyl donor is an anhydride, $R^x$ is $(C_1-C_4)$alkyl-$R^y$.$R^y$ is selected from the group consisting of H and $CO_2H$, the catalyst is 4-dimethylaminopyridine, the base for the first step is pyridine, the solvent for the first step is an aromatic solvent, the reaction mixture in the first step is stirred at about 0 to about 60° C., the solvent for the hydrolysis is diisopropyl ether:phosphate buffer 1:2, the enzyme is CAL-B, and hydrolysis reaction is stirred at about 0 to about 30° C.

In particular embodiments, the acyl donor is glutaric anhydride, R" is $(CH_2)_3$—$CO_2H$, the catalyst is 4-dimethylaminopyridine, the base for the first step is pyridine, the solvent for the first step is pyridine, the reaction mixture in the first step is stirred at about 60° C., the solvent for the hydrolysis is diisopropyl ether:phosphate buffer 1:2, the enzyme is CAL-B, the hydrolysis reaction is stirred at about 30° C., and e-2 is removed by extraction in a basic aqueous layer.

In certain embodiments, the enantiomeric excess (% ee) of the product is about 50 to 100, about 75 to 100, about 90 to 100, about 95 to 100, about 98 to 100, about 98.5 to 100, about 98.5 to 99, about 99 to 100, about 99.5 to 100, about 99.9 to 100.

T. Classical Resolution of c-1a

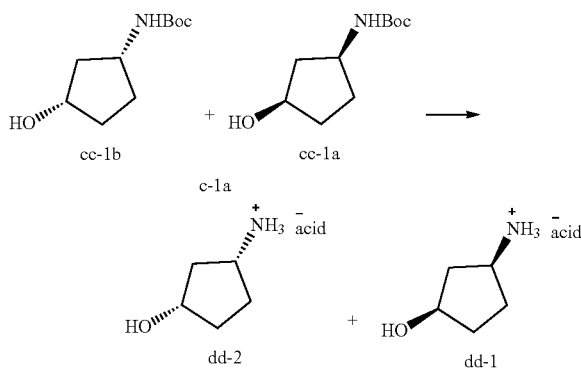

In certain embodiments, c-1a is resolved via a classical resolution process. In this process, c-1a, an acid, and a solvent are combined.

In certain embodiments, the acid is selected from the group consisting of:
single enantiomers of carboxylic acids including but not limited to: naproxen, phenyl succinic acid, malic acid, 2-phenylpropionic acid, alpha-methoxyphenyl acetic acid, tartranilic acid, 3-phenyllactic acid, α-hydroxyisovaleric acid, 2'-methoxy-tartranilic acid, (alpha-methylbenzyl)phthalamic acid, 2'-chloro-tartranilic acid, pyroglutamic acid;
single enantiomers of mandelic acid derivatives including but not limited to: mandelic acid, 2-chloromandelic acid, 4-bromo-mandelic acid, 0-acetyl mandelic acid, 4-methyl-mandelic acid;
single enantiomers of sulfonic acids including but not limited to: camphor sulfonic acid;
single enantiomers of tartaric acid derivatives including but not limited to: tartaric acid, dibenzoyl tartaric acid hydrate, di-p-anisoyltartaric acid, di-toluyltartaric acid, dibenzoyl tartaric acid hydrate;
single enantiomers of phosphoric acid derivatives including but not limited to: phencyphos hydrate, chlocyphos, anisyphos, BINAP phosphate; and
single enantiomers of amino acids including but not limited to: N-acetyl-phenylalanine, N-acetyl-leucine, N-acetyl-proline, boc-phenylalanine, and boc-homophenylalanine.

In some embodiments, the acid is (S)-Naproxen or S-(+)-mandelic acid. In particular embodiments, the acid is (S)-Naproxen. In particular embodiments, the acid is S-(+)-mandelic acid.

In certain embodiments, the solvent is water, acetonitrile, ethanol, isopropanol, methyl ethyl ketone, isopropyl acetate, dioxane, a mixture of water and a water-miscible organic solvents such as ethanol and isopropanol, an halogenated solvent such as dichloromethane and chloroform. In particular embodiments, the solvent is water or isopropanol or a mixture thereof. In particular embodiments, the solvent is water. In particular embodiments, the solvent is isopropanol.

In certain embodiments, the reaction is stirred at 0 to 120° C., 2 to 120° C., 50 to 120° C., 80 to 120° C., about 100° C. In certain embodiments, the reaction is stirred at about 20° C.

In certain embodiments, the product is extracted and optionally purified by any suitable technique known in the art, such as, but not limited to solvent extraction, chromatography, crystallization or a combination thereof.

In certain embodiments, dd-1 precipitates out of solution and is filtered. The solid may be further recrystallized in a solvent such as isopropanol.

In particular embodiments, removal of the solvent by evaporation yields a mixture of dd-1 and dd-2. The mixture is suspended in a solvent.

In certain embodiments, dd-1 is selectively recrystallized.

In certain embodiments, the solvent is water, acetonitrile, ethanol, isopropanol, methyl ethyl ketone, isopropyl acetate, dioxane; a mixture of water and water-miscible organic solvents such as ethanol and isopropanol, or a halogenated solvent such as dichloromethane or chloroform. In particular embodiments, the solvent is a mixture of methyl ethyl ketone and water.

In certain embodiments, the mixture is stirred at about 0 to 100° C., about 20 to 80° C., about 40 to 60° C.

In certain embodiments, the mixture is allowed to cool to room temperature and the solid is isolated by filtration, dried and recrystallized from 10% water in methyl ethyl ketone to provide enantioenriched dd-1.

In particular embodiments, the acid is S-(+)-mandelic acid or (S)-Naproxen, the solvent is water or isopropanol, the reaction is stirred at about 0 to about 20° C., and dd-1 the product is isolated by solvent extraction, chromatography, crystallization or a combination thereof.

In particular embodiments, the acid is S-(+)-mandelic acid, the solvent is isopropanol, the reaction is stirred at about 20° C., and dd-1 precipitates out of solution.

In particular embodiments, the acid is the acid is (S)-Naproxen, the solvent is water, the reaction is stirred at about 20° C., and dd-1 is selectively recrystallized in a mixture of methyl ethyl ketone and water.

In certain embodiments, the enantiomeric excess (% ee) of the product is about 50 to 100, about 75 to 100, about 90 to 100, about 95 to 100, about 98 to 100, about 98.5 to 100, about 98.5 to 99, about 99 to 100, about 99.5 to 100, about 99.9 to 100.

U. Allylic Amination

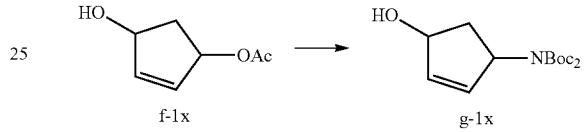

f-1x    g-1x

In certain embodiments, an allylic amination process for obtaining g-1x is provided. In this process, a ligand and a catalyst are mixed in degassed solvent, followed by addition of f-1x, a base and a nucleophile.

In certain embodiments, the ligand is absent, tricyclohexylphosphine, 1,3-bis(diphenylphosphino)propane; 1,2-bis(diphenylphosphino)ethane, triphenylphosphine or 1,1'-bis(diphenylphosphino)ferrocene. In particular embodiments, the ligand is triphenylphosphine.

In certain embodiments, the catalyst is a Palladium catalyst such as $Pd(OAc)_2$, $PdCl_2(PPh_3)$, $Pd(tBu_2Ph)_2Cl_2$, Tris(dibenzylideneacetone)dipalladium(0) and $Pd(amphos)_2Cl_2$. In particular embodiments, the catalyst is Tris(dibenzylideneacetone)dipalladium(0).

In certain embodiments, the solvent is an ether such as dimethoxyethane, THF or MeTHF, an aromatic solvent such as toluene and benzene. In particular embodiments, the solvent is THF.

In certain embodiments, the base is potassium isopropoxide, cesium hydroxide, Hunig's base or a carbonate base such as cesium carbonate, potassium carbonate and sodium carbonate. In particular embodiments, the base is cesium carbonate.

In certain embodiments, the nucleophile is a phthalamide such as potassium phthalamide, an azide such as sodium azide or TMS-azide, an amine such as benzylamine or dibenzylamine, a carboxylate such as di-tert-butyl iminodicarboxylate. In particular embodiments, the nucleophile is di-tert-butyl iminodicarboxylate.

In certain embodiments, about 1 equivalent of nucleophile is added.

In certain embodiments, the reaction is stirred at about 20 to 80° C., about 30 to 70° C., about 40 to 60° C., about 50° C.

In certain embodiments, the mixture is heated to about 50° C. for approximately 18 h.

In certain embodiments, the product formed is extracted and optionally purified by any suitable technique known in the art, such as, but not limited to solvent extraction, chromatography, crystallization or a combination thereof.

In certain embodiments, the mixture is cooled and water and ethyl acetate are added. The layers are separated and the organic phase is washed with ethyl acetate. The combined organics are concentrated to dryness. The residue is purified by silica gel column chromatography (0 to 40% ethyl acetate in hexane). The isolated material is dissolved in MeTHF, washed with 5% aq. KOH, concentrated, and purified by silica gel column chromatography (0 to 10% methanol in dichloromethane) to provide g-1x.

In particular embodiments, the ligand is triphenylphosphine, the catalyst is a palladium cataloyst, the solvent is an ether, the base is a carbonate base, the nucleophile is di-tert-butyl iminodicarboxylate, and the reaction is stirred at about 20 to about 80° C.

In particular embodiments, the ligand is triphenylphosphine, the catalyst is Tris(dibenzylideneacetone)dipalladium (0), the solvent is THF, the base is cesium carbonate, the nucleophile is di-tert-butyl iminodicarboxylate, and the reaction is stirred at about 50° C.

V. Hydrogenation

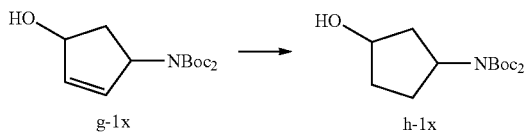

In certain embodiments, a hydrogenation process for obtaining h-1x is provided. In this process, g-1x and a catalyst are combined in a solvent, followed by addition of a source of hydrogen.

In certain embodiments, the catalyst is a platinum catalyst such as $PtO_2$, a palladium catalyst, a nickel catalyst such as Raney Nickel, a rhodium catalyst such as $RhCl(PPh_3)_3$, a ruthenium catalyst such as Nyori's catalyst, or an iridium catalyst such as Crabtree's catalyst. In some embodiments, the catalyst is selected form the group consisting of Pd/C, $PtO_2$, Raney Nickel, $RhCl(PPh_3)_3$, Nyori's catalyst, and Crabtree's catalyst. In particular embodiments, the catalyst is $PtO_2$.

In certain embodiments, the solvent is a polar aprotic solvent such as THF, 2-MeTHF, dioxane, diethyl ether, diisopropyl ether, DME, MTBE, CPME, EtOAc and DCM or a polar protic solvent such as methanol, isopropanol, ethanol, and n-butanol. In particular embodiments, the solvent is isopropanol.

In certain embodiments, the reaction is stirred at about 0 to 65° C., about 5 to 55° C., about 10 to 45° C., about 10 to 35° C., or about 15 to 25° C.

In certain embodiments, the source of hydrogen is formic acid, hydrazine, dihydronapthalene, dihydroanthracene, $H_2$ gas or Hantzch ester and isopropanol. In particular embodiments, the source of hydrogen is $H_2$ gas. In particular embodiments, the source of hydrogen is an atmosphere of hydrogen.

In certain embodiments, the reaction is stirred for 1 to 48 h, 6 to 24 h, 10 to 20 h, 16 to 20 h, or about 18 h.

In certain embodiments, h-1x is extracted and optionally purified by any suitable technique known in the art, such as, but not limited to solvent extraction, chromatography, crystallization or a combination thereof.

In certain embodiments, the mixture is filtered through celite and used without further purification in the subsequent deprotection.

In particular embodiments, the catalyst is a platinum catalyst, the solvent is a polar protic solvent, the reaction is stirred at about 5 to 55° C., and the source of hydrogen is $H_2$ gas.

In particular embodiments, the catalyst is $PtO_2$, the solvent is isopropanol, the reaction is stirred at about 15 to 25° C., and the source of hydrogen is $H_2$ gas.

W. Deprotection

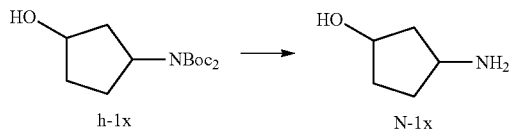

In certain embodiments, a deprotection process for obtaining N-1x is provided. In this process, h-1x is added to an acid in a solvent.

In certain embodiments, the acid is a sulfonic acid such as methanesulfonic acid, p-toluenesulfonic acid and camphorsulfonic acid, an inorganic acid such as phosphoric acid, hydrochloric acid and sulfuric acid, a carboxylic acid such as trifluoroacetic acid, oxalic acid and benzoic acid. In particular embodiments, the acid is anhydrous hydrochloric acid.

In certain embodiments, the solvent is an alcoholic solvent such as methanol, isopropanol and ethanol, or a polar aprotic solvent such as dioxane, acetonitrile and dichloromethane, or water. In certain embodiments, the solvent is an alcoholic solvent. In certain embodiments, the solvent is a polar aprotic solvent. In certain embodiments, the solvent is water. In certain embodiments, the solvent is methanol, isopropanol, ethanol, dioxane, acetonitrile, dichloromethane, or water. In particular embodiments, the solvent is isopropanol.

In certain embodiments, the reaction is stirred at about 0 to 80° C., about 0 to 60° C., about 5 to 45° C., about 10 to 35° C., or about 15 to 25° C.

In certain embodiments, about 1 to 10 equivalents, about 5 to 10 equivalents, or about 7 equivalents of acid is used.

In certain embodiments, the reaction is stirred for about 1 to 48 h, about 6 to 24 h, about 12 to 24 h, or about 18 h.

In certain embodiments, the product formed, N-1x, is extracted and optionally purified by any suitable technique known in the art, such as, but not limited to solvent extraction, chromatography, crystallization or a combination thereof.

In particular embodiments, the reaction is cooled to approximately 0° C. and the product N-1x is collected by filtration.

In particular embodiments, the acid is an inorganic acid, the solvent is an alcoholic solvent, and the reaction is stirred at 5 to 45° C.

In particular embodiments, the acid is anhydrous hydrochloric acid, the solvent is isopropanol, and the reaction is stirred at 15 to 25° C.

EXAMPLES

In order for this invention to be more fully understood, the following examples are set forth. These examples are for the purpose of illustrating embodiments, and are not to be construed as limiting the scope of this disclosure in any way. The reactants used in the examples below may be obtained either as described herein, or if not described herein, are themselves either commercially available or may be prepared from commercially available materials by methods known in the art.

In one embodiment, a multi-step synthetic method for preparing a compound of Formula I is provided, as set forth below. In certain embodiments, each of the individual steps of the Schemes set forth below is provided. Examples and any combination of two or more successive steps of the below Examples are provided.

A. Acylation and Amidation of Meldrum's Acid to Form C-1a:

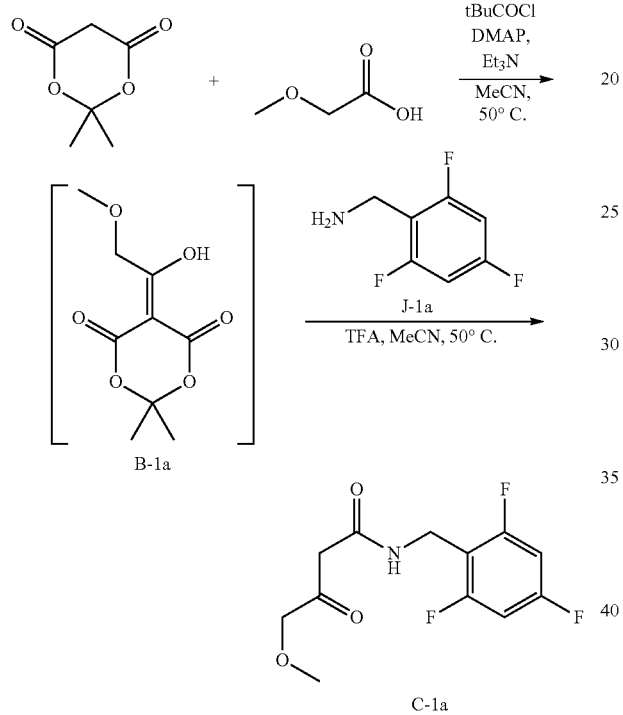

In a reaction vessel, Meldrum's acid (101 g, 1.0 equivalent) and 4-dimethylaminopyridine (1.8 g, 0.2 equivalents) were combined with acetonitrile (300 mL). The resulting solution was treated with methoxyacetic acid (6.2 mL, 1.2 equivalents). Triethylamine (19.4 mL, 2.0 equivalents) was added slowly to the resulting solution, followed by pivaloyl chloride (9.4 mL, 1.1 equivalents). The reaction was then heated to about 45 to about 50° C. and aged until consumption of Meldrum's acid was deemed complete.

A separate reaction vessel was charged with acetonitrile (50 mL) and J-1a (13.4 g, 1.2 equivalents). The resulting solution was treated with trifluoroacetic acid (8.0 mL, 1.5 equivalents), and then this acidic solution was added to the acylation reaction in progress at about 45 to about 50° C.

The reaction was allowed to age for at least 18 hours at about 45 to about 50° C., after which time the solvent was removed under reduced pressure. The crude residue was dissolved in ethyl acetate (150 mL), and the organic layer was washed with water. The combined aqueous layers were extracted with ethyl acetate. The combined organic layers were washed with saturated sodium bicarbonate solution, and the combined bicarbonate washes were back extracted with ethyl acetate. The combined organic layers were dried over magnesium sulfate, filtered, and concentrated under reduced pressure. The resulting crude material was purified twice via silica gel chromatography to yield C-1a.

$^1$H NMR (400 MHz, CDCl$_3$): δ 7.12 (br, 1H), 6.66 (app t, J=8.1 Hz, 2H), 4.50 (app d, J=5.7 Hz, 2H), 4.08 (s, 2H), 3.44 (s, 2H), 3.40 (s, 3H). $^{13}$C NMR (100 MHz, CDCl$_3$): δ 203.96, 164.90, 162.37 (ddd, J=250.0, 15.7, 15.7 Hz), 161.71 (ddd, J=250.3, 14.9, 10.9 Hz), 110.05 (ddd, J=19.7, 19.7, 4.7 Hz), 100.42 (m), 77.58, 59.41, 45.71, 31.17 (t, J=3.5 Hz). LCMS, Calculated: 275.23, Found: 275.97 (M).

B. Alkylation of C-1a to Form E-1a:

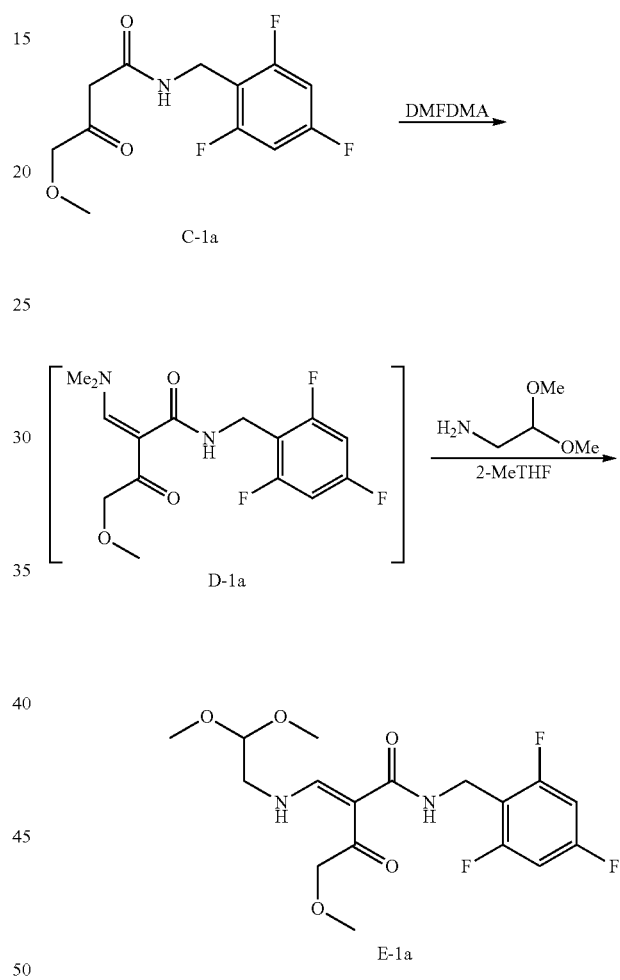

A solution of C-1a (248 mg, 1.0 equivalent) and 2-methyl tetrahydrofuran (1.3 mL) was treated with N,N-dimethylformamide dimethylacetal (0.1 mL, 1.1 equivalent) and stirred at room temperature overnight (~14 hours). The reaction was treated with aminoacetaldehyde dimethyl acetal (0.1 mL, 1.0 equivalents), and was allowed to age for about 2 hours, and then was quenched via the addition of 2 N HCl (1.5 mL).

The reaction was diluted via the addition of ethyl acetate, and phases were separated. The aqueous layer was extracted with ethyl acetate. The combined organic layers were washed with brine, dried over magnesium sulfate, filtered, and concentrated under reduced pressure. The crude residue was purified via silica gel chromatography to yield E-1a.

$^1$H NMR (400 MHz, CDCl$_3$): δ 10.85 (s, 1H), 9.86 (s, 1H), 8.02 (d, J=13.1 Hz, 1H), 6.65 (dd, J=8.7, 7.7 Hz, 2H), 4.53 (d, J=3.9 Hz, 2H), 4.40 (t, J=5.1 Hz, 1H), 4.18 (s, 2H), 3.42 (s, 6H), 3.39 (m, 2H), 3.37 (s, 3H). $^{13}$C NMR (100 MHz, CDCl$_3$): δ 193.30, 169.15, 162.10 (ddd, J=248.9, 15.5, 15.5 Hz), 161.7 (ddd, J=250.0, 14.9, 11.1 Hz), 161.66, 111.08 (ddd J=19.9, 19.9, 4.7 Hz) 103.12, 100.29 (ddd, 0.1=28.1, 17.7, 2.3 Hz), 76.30, 58.83, 54.98, 53.53, 51.57, 29.89 (t, J=3.3 Hz). LCMS, Calculated: 390.36, Found: 390.92 (M).

C. Cyclization of E-1a to Form F-1a:

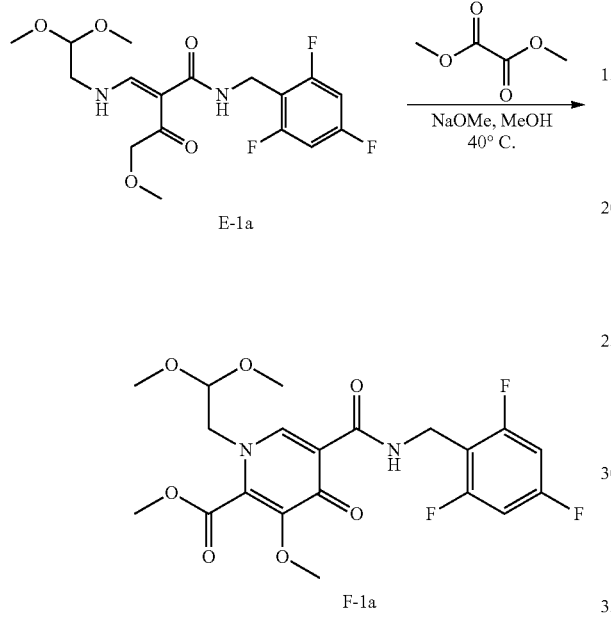

E-1a (0.2 g, 1.0 equivalent), dimethyl oxalate (0.1 g, 2.5 equivalents) and methanol (1.5 mL) were combined and cooled to about 0 to about 5° C. Sodium methoxide (0.2 mL, 30% solution in methanol, 1.75 equivalents) was introduced to the reaction slowly while keeping the internal temperature of the reaction below about 10° C. throughout the addition. After the addition was completed the reaction was heated to about 40 to about 50° C. for at least 18 hours.

After this time had elapsed, the reaction was diluted with 2 N HCl (1.5 mL) and ethyl acetate (2 mL). The phases were separated, and the aqueous phase was extracted with ethyl acetate. The combined organic layers were washed with brine, dried over magnesium sulfate, filtered, and solvent was removed under reduced pressure. The resulting crude oil was purified via silica gel chromatography to afford F-1a.

$^1$H NMR (400 MHz, CDCl$_3$): δ 10.28 (t, J=5.5 Hz, 1H), 8.38 (s, 1H), 6.66-6.53 (m, 2H), 4.58 (d, J=5.6 Hz, 2H), 4.43 (t, J=4.7 Hz, 1H), 4.00 (d, J=4.7 Hz, 2H), 3.92 (s, 3H), 3.88 (s, 3H), 3.32 (s, 6H). $^{13}$C NMR (100 MHz, CDCl$_3$): δ 173.08, 163.81, 162.17, 162.14 (ddd, J=249.2, 15.6, 15.6 Hz), 161.72 (ddd, J=250.5, 15.0, 10.9 Hz), 149.37, 144.64, 134.98, 119.21, 110.53 (ddd, J=19.8, 4.7, 4.7 Hz), 102.70, 100.22 (m), 60.68, 56.75, 55.61, 53.35, 30.64. LCMS, Calculated: 458.39, Found: 459.15 (M+H).

D. Alkylation and Cyclization of C-1a to Form F-1a:

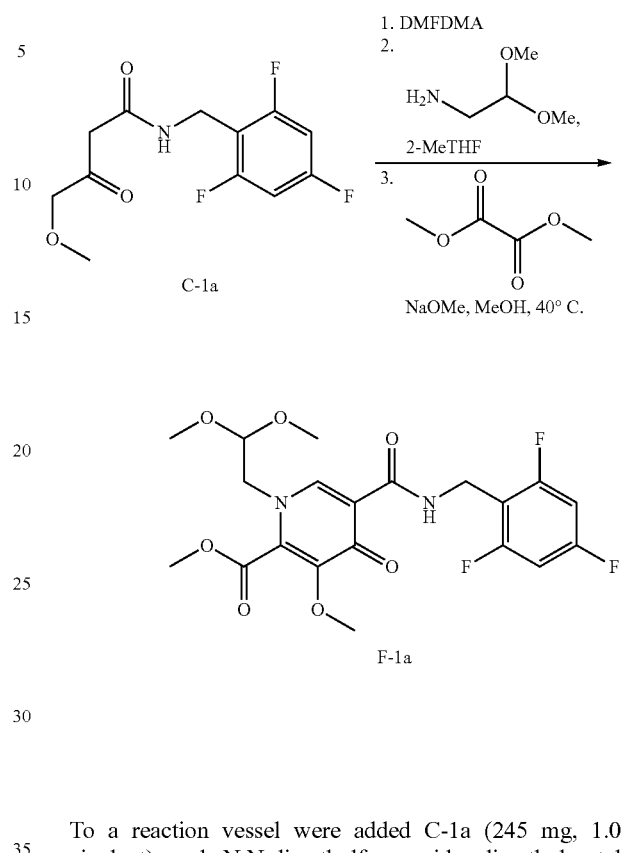

To a reaction vessel were added C-1a (245 mg, 1.0 equivalent) and N,N-dimethylformamide dimethylacetal (0.5 mL, 4.3 equivalent). The reaction mixture was agitated for approximately 30 minutes. The reaction was then treated with 2-methyl tetrahydrofuran (2.0 mL) and aminoacetaldehyde dimethyl acetal (0.1 mL, 1.0 equivalent). The reaction was allowed to age for several hours and then solvent was removed under reduced pressure.

The resulting material was dissolved in methanol and dimethyl oxalate was added (0.3 g, 2.5 equivalents). The reaction mixture was cooled to about 0 to about 5° C., and then sodium methoxide (0.4 mL, 30% solution in methanol, 1.75 equivalents) was introduced to the reaction slowly. After the addition was completed the reaction was heated to about 40 to about 50° C.

After this time had elapsed, the reaction was cooled to room temperature and quenched via the addition of 2 N HCl (1.5 mL). The reaction was then diluted with ethyl acetate, and the resulting phases were separated. The aqueous layer was extracted with ethyl acetate. The combined organic layers were dried over magnesium sulfate, filtered, and concentrated under reduced pressure. The crude residue was purified via silica gel chromatography to yield F-1a.

$^1$H NMR (400 MHz, CDCl$_3$): δ 10.28 (t, J=5.5 Hz, 1H), 8.38 (s, 1H), 6.66-6.53 (m, 2H), 4.58 (d, J=5.6 Hz, 2H), 4.43 (t, J=4.7 Hz, 1H), 4.00 (d, J=4.7 Hz, 2H), 3.92 (s, 3H), 3.88 (s, 3H), 3.32 (s, 6H). $^{13}$C NMR (100 MHz, CDCl$_3$): δ 173.08, 163.81, 162.17, 162.14 (ddd, J=249.2, 15.6, 15.6 Hz), 161.72 (ddd, J=250.5, 15.0, 10.9 Hz), 149.37, 144.64, 134.98, 119.21, 110.53 (ddd, J=19.8, 4.7, 4.7 Hz), 102.70, 100.22 (m), 60.68, 56.75, 55.61, 53.35, 30.64. LCMS, Calculated: 458.39, Found: 459.15 (M+H).

E. Condensation of F-1a with N-1a to form G-1a:

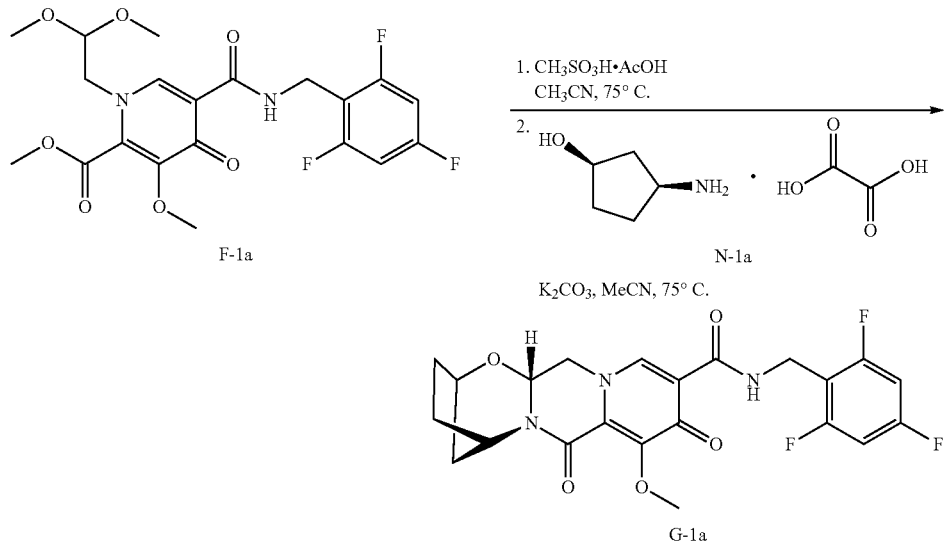

To a reaction vessel were added F-1a (202 mg, 1.0 equivalent) and acetonitrile (1.4 mL). The resulting solution was treated with glacial acetic acid (0.2 mL, 6.0 equivalents) and methane sulfonic acid (0.01 mL, 0.3 equivalents). The reaction was then heated to about 70 to about 75° C.

After 3 hours, a solid mixture of N-1a (0.128 g, 1.5 equivalents) and potassium carbonate (0.2 g, 2.7 equivalents) was introduced to the reaction at about 70 to about 75° C. After the addition was completed, the reaction was allowed to progress for at least about 1 hour.

After this time had elapsed, water (1.4 mL) and dichloromethane (1.4 mL) were introduced to the reaction. The phases were separated, and the aqueous layer was extracted with dichloromethane. The combined organic layers were dried over magnesium sulfate, then were filtered and concentrated under reduced pressure. The resulting crude material was purified via silica gel chromatography to obtain G-1a.

$^1$H NMR (400 MHz, CDCl$_3$): δ 10.23 (t, J=5.5 Hz, 1H), 8.39 (s, 1H), 6.60 (t, J=8.1 Hz, 2H), 5.29 (dd, J=9.5, 3.7 Hz, 2H), 4.57 (d, J=5.4 Hz, 3H), 4.33 (dd, J=12.8, 3.8 Hz, 1H), 4.02-3.87 (m, 1H), 3.94 (s, 3H), 2.06-1.88 (m, 4H), 1.78 (dd, J=17.2, 7.5 Hz, 1H), 1.55-1.46 (m, 1H). $^{13}$C NMR (100 MHz, CDCl$_3$): δ 174.53, 163.75, 162.33 (dd, J=249.4, 15.7, 15.7 Hz), 161.86 (ddd, J=250.4, 14.9, 10.9 Hz), 154.18, 154.15, 142.44, 129.75, 118.88, 110.58 (ddd, J=19.8, 4.7, 4.7 Hz), 100.42 (m), 77.64, 74.40, 61.23, 54.79, 51.13, 38.31, 30.73, 29.55, 28.04. LCMS, Calculated: 463.14, Found: 464.15 (M+H).

F. Deprotection of G-1a to Form a Compound of Formula Ia:

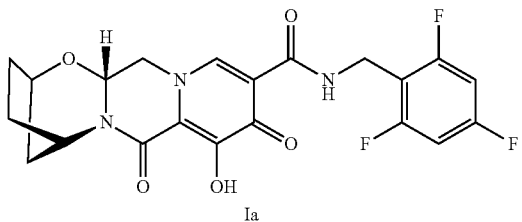

G-1a (14 g) was suspended in acetonitrile (150 mL) and dichloromethane (150 mL). MgBr$_2$ (12 g) was added. The reaction was heated to 40 to 50° C. for approximately 10 min before being cooled to room temperature. The reaction was poured into 0.5M HCl (140 mL) and the layers separated. The organic layer was washed with water (70 mL), and the organic layer was then concentrated. The crude product was purified by silica gel chromatography (100% dichloromethane up to 6% ethanol/dichloromethane) to afford Ia.

G. Hydrolysis of F-1a to Form II-a:

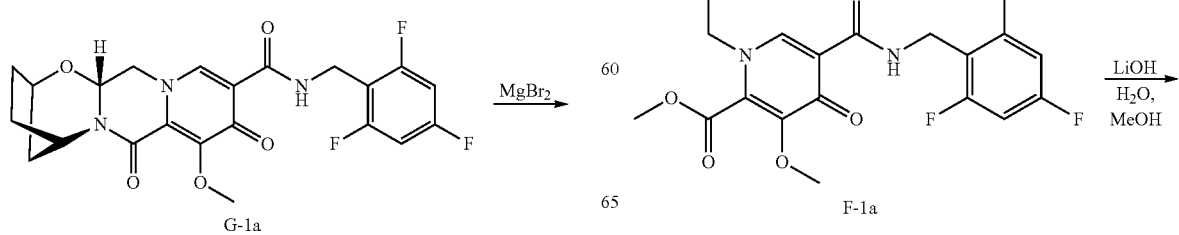

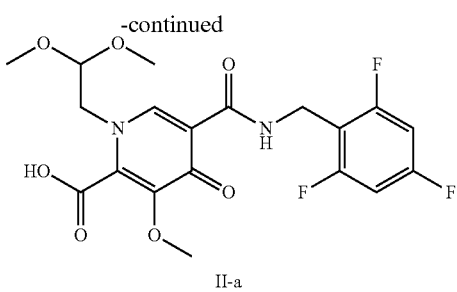

II-a

To a reaction vessel were added F-1a (480 mg, 1.0 equiv.), methanol (5.8 mL) and water (2.4 mL). To the resulting homogeneous solution, lithium hydroxide monohydrate (88 mg, 2.0 equiv.) is added. The resulting suspension was stirred at room temperature for about 17 hours.

Water (15 mL) and ethyl acetate were added, then 1N HCl was added dropwise until the pH was about 3. The layers were mixed and separated, the aqueous layer extracted with ethyl acetate (15 mL), and the combined organic layers dried over Na$_2$SO$_4$. The organic layer was removed by evaporation. The aqueous layer was then brought to pH<2, and extracted twice with ethyl acetate (2×15 mL). The combined organic layers were dried over Na$_2$SO$_4$, mixed with the residue from the previous extraction and the solvent was removed by evaporation. The residue was taken up in MTBE (2.4 mL), to form a slurry, which was filtered and washed with MTBE to provide 1002.

$^1$H NMR (400 MHz, CDCl$_3$): δ 10.43 (t, J=5.2 Hz, 1H), 9.65 (bs, 1H), 8.52 (s, 1H), 6.67 (t, J=8.0 Hz, 2H), 4.67 (d, J=6.0 Hz, 2H), 4.58 (t, J=4.8 Hz, 1H), 4.16 (d, J=4.8 Hz, 1H), 3.91 (s, 3H), 3.37 (s, 6H). $^{13}$C NMR (100 MHz, CDCl$_3$): δ 173.04, 164.15, 162.10, 148.63, 145.28, 137.25, 118.66, 102.46, 100.35 (t, J=30.7 Hz), 87.42, 61.30, 57.09, 55.55, 30.94.

H. Preparation of BB-1a from B-1a:

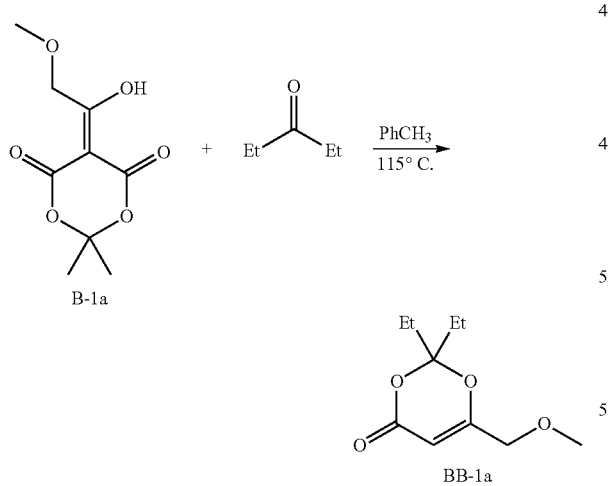

To a reaction vessel was added B-1a (0.2 g, 1.0 equivalent) and 3-pentanone (1.0 mL, 10.0 equivalents). These compounds were then dissolved in toluene (1.0 mL) and heated to about 110 to about 115° C. The reaction was maintained at this temperature for about 4 hours, after which time the reaction was cooled to room temperature and solvent was removed. The resulting crude material was purified over silica gel to afford BB-1a.

$^1$H NMR (400 MHz, CDCl$_3$): δ 5.46 (t, J=1.1 Hz, 1H), 3.97 (d, J=1.0 Hz, 2H), 3.42 (s, 3H), 1.99 (m, 4H), 0.98 (t, J=7.5 Hz, 6H). $^{13}$C NMR (100 MHz, CDCl$_3$): δ 167.63, 160.94, 111.05, 93.04, 70.07, 59.27, 28.08, 7.40. LCMS, Calculated: 200.10, Found 200.79 (M+).

I. Preparation of C-1a from BB-1a:

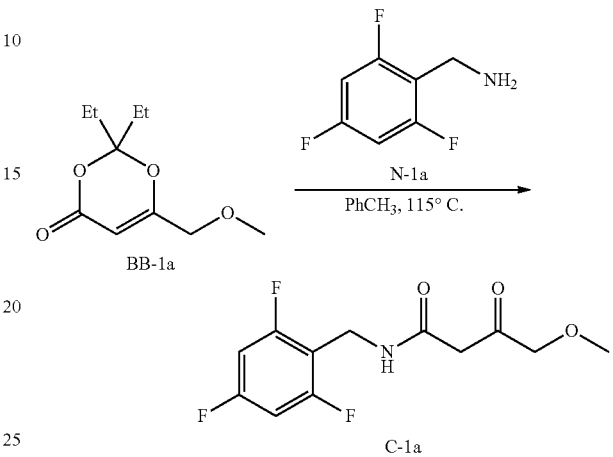

To a reaction vessel was added BB-1a (0.08 g, 1.0 equivalent) and N-1a (0.08 g, 1.1 equivalents). These compounds were then dissolved in toluene (1.5 mL) and heated to about 115° C. After about 1 h, the reaction was cooled and solvent was removed. The resulting crude material was purified via silica gel chromatography to obtain C-1a.

All spectral data collected for C-1a matched that provided above.

J. Formation of B-1a.J-1a Salt:

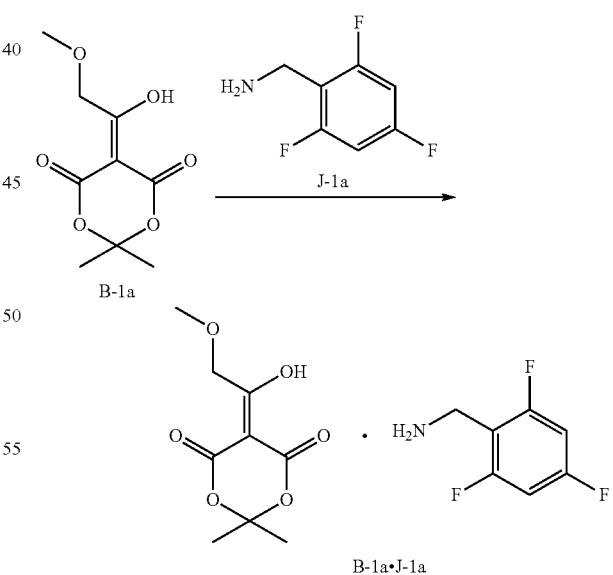

The free acid of B-1a (4.4 g) was dissolved in 50 mL acetonitrile and J-1a (3.3 g, 1.0 equivalent) in 30 mL acetonitrile was added. The desired salt was obtained and was aged for about one hour at room temperature. The solids were filtered and the cake was rinsed with 2×10 mL acetonitrile to afford the product.

NMR (400 MHz, DMSO-d$^6$) δ 7.40 (bs, 3H), 6.11 (t, J=7.7 Hz, 2H), 3.12 (s, 2H), 2.92 (s, 2H), 2.08 (s, 3H), 0.35 (s, 6H). $^{13}$C NMR (101 MHz, DMSO-d$^6$) δ 191.98, 164.66, 163.06 (dt, J=248.6, 16.2 Hz), 161.82 (ddd, J=250.4, 15.8, 10.4 Hz), 107.39 (td, J=20.0, 4.7 Hz), 101.16 (m), 100.01, 87.01, 77.71, 58.39, 30.45, 26.37.

K. Formation of B-1a.J-1a Salt:

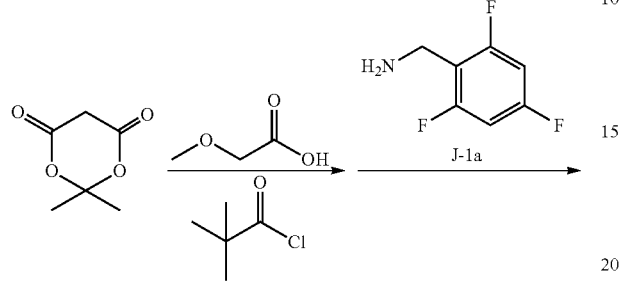

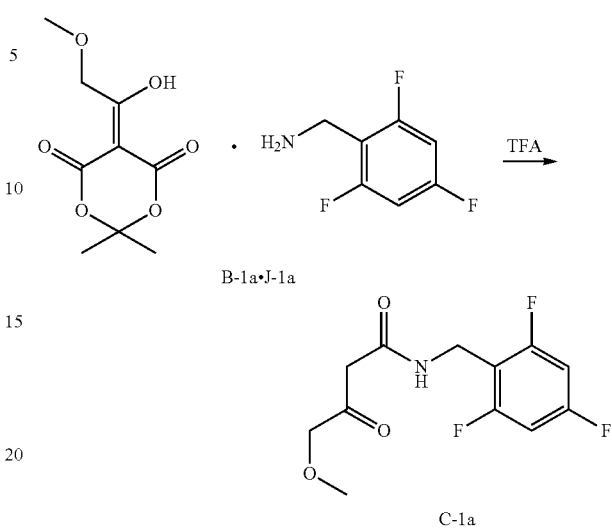

Meldrum's acid (10.1 g, 1.1 equivalents) and DMAP (0.6 g, 0.08 equivalents) were dissolved in 300 mL acetonitrile. Methoxyacetic acid (5.8 g, 1 equivalents) and 17.6 g (2.1 equivalents) Hunig's base were added. The solution was warmed to about 45° C. and 8.4 g (1.1 equivalents) of pivaloyl chloride in 30 mL of acetonitrile was added over about 1 hour.

After about 2.5 hours at about 45° C., the solution was cooled to room temperature and was concentrated under vacuum. The resulting oil was dissolved in 110 mL dichloromethane, cooled over ice bath, and extracted with 50 mL 1N HCl. The layers were separated, and the aqueous layer was extracted with 40 mL dichloromethane. The combined organic layer was concentrated and diluted in acetonitrile and evaporated again. The material was dissolved in 220 mL acetonitrile.

After cooling over an ice bath, trifluorobenzylamine (11.4 g, 1.1 equivalents) and the mixture at about 9° C. was allowed to warm up to room temperature and agitated as the slurry thickened. After about 2 hours, 220 mL MTBE was added slowly and the slurry was aged overnight. The slurry was cooled over ice bath for about 3 hours and was filtered, rinsed with 50 mL cold 1:1 acetonitrile/MTBE, and dried overnight in a vacuum oven to afford the product.

L. Amidation Using the B-1a.J-1a Salt to Form C-1a

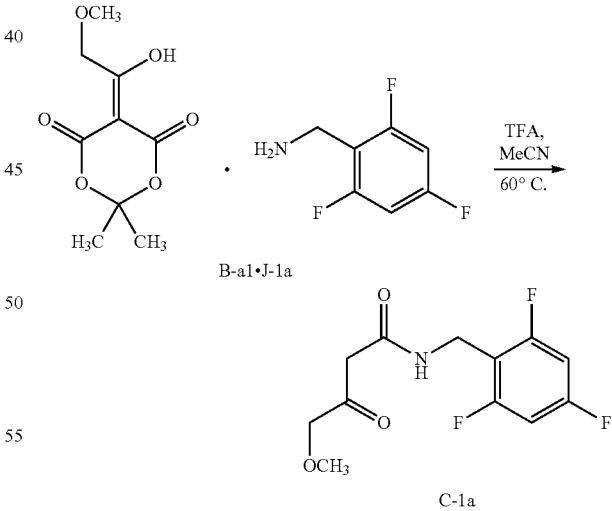

The salt B-1a.J-1a (3.7 g, 1.0 equivalent) was suspended in 50 mL of acetonitrile, and then was treated with trifluoroacetic acid (0.1 mL, 0.1 equivalent). The reaction was heated to about 40 to about 50° C. for approximately 18 hours, and then cooled to room temperature. Solvent was removed under reduced pressure, and the resulting residue was suspended in 5 volumes of 2-methyl tetrahydrofuran and 5 volumes of hexanes were added dropwise over 1 h. The resulting mixture was allowed to stir for at least 24 hours, and then the resulting slurry was filtered to afford the product.

M. Amidation of B-1a.J-1a to C-1a:

B-1a.J-1a (75.077 g, 198.97 mmol, 1.0 equivalent), acetonitrile (750 mL), and trifluoroacetic acid (1.5 mL, 20 mmol, 0.1 equiv) were combined in a reactor. The reactor was heated until the internal temperature reached about 58° C., and the reactor contents were aged between about 58-61° C. for about 3.5 hours. The jacket temperature was then adjusted to about 45° C. and vacuum was applied. The reactor contents were distilled until about 150 mL remained.

iso-Propylacetate (300 mL) was then charged to the reactor, and distillation was continued until the volume reached about 150 mL. iso-Propylacetate (150 mL) was then charged to the reactor, the jacket temperature was adjusted to about 20° C., and contents were allowed to reach an internal temperature of <25° C. A wash solution (22.8% NaCl, 1.5% $H_2SO_4$, 75.7% water, 300 mL) was charged to the reactor, and the contents were agitated for about 30 minutes. The bottom phase was separated, and a second wash solution (22.8% NaCl, 1.5% $H_2SO_4$, 75.7% water, 300 mL) was charged to the reactor. After agitating for about 15 minutes, the bottom phase was separated, and 20% aqueous NaCl (300 mL) was charged to the reactor and agitated for about 15 minutes. The bottom phase was separated. Heptane (150 mL) was charged to the reactor, followed by seed (51 mg, 0.1 wt %). The mixture was aged for about 30 minutes, during which a slurry formed. Additional heptane (450 mL) was then charged over no less than 30 minutes. The jacket temperature was then adjusted to about 29° C., and solvent was distilled under vacuum until the reactor contents reached a volume of about 450 mL. The slurry was then cooled to an internal temperature of about 5° C. over no less than 1 hour. The reactor contents were discharged and solids were collected by filtration. The mother liquors were recycled twice in order to displace solids from the reactor, each time allowing the internal temperature to reach about <6° C. before discharging. A solution of heptane/iso-propylacetate (75% v/v, 225 mL) was then charged to the reactor, and when the internal temperature reached <6° C., the slurry was rinsed forward through the filter cake. The wet cake was then dried under vacuum at about 40° C. for about 18 hours, providing C-1a.

$^1$H NMR (400 MHz, $CDCl_3$): δ 7.12 (br, 1H), 6.66 (app t, J=8.1 Hz, 2H), 4.50 (app d, J=5.7 Hz, 2H), 4.08 (s, 2H), 3.44 (s, 2H), 3.40 (s, 3H). $^{13}$C NMR (100 MHz, $CDCl_3$): δ 203.96, 164.90, 162.37 (ddd, J=250.0, 15.7, 15.7 Hz), 161.71 (ddd, J=250.3, 14.9, 10.9 Hz), 110.05 (ddd, J=19.7, 19.7, 4.7 Hz), 100.42 (m), 77.58, 59.41, 45.71, 31.17 (t, J=3.5 Hz). LCMS, Calculated: 275.23, Found: 275.97 (M).

N. Enamine Formation of D-1a from C-1a

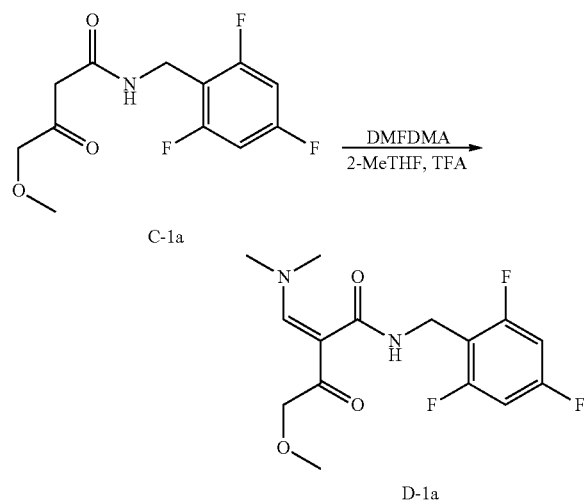

C-1a (8.4 g, 1.0 equiv) was charged to a reactor, followed by the addition of 2-methyltetrahydrofuran (166.7 mL, 20 volumes, 0.18 M) and trifluoroacetic acid (231.9 uL, 0.1 equiv). The reaction mixture was heated to an internal temperature of about 40° C., and DMF-DMA (3.0 mL, 0.75 equiv) was quickly added. The reaction mixture is agitated for a few minutes, followed by the addition of D-1a seeds (20 mgs, 0.002 equivalent) at about 40° C. The heterogenous mixture was aged at 40° C. for about one hour. An additional portion of DMF-DMA was added (1.5 mL, 0.37 equivalent), and the reaction mixture was agitated for about 25 minutes. One final portion of DMF-DMA (1.5 mL, 0.37 equiv) was added, and the reaction mixture was cooled from about 40° C. to room temperature and allowed to agitate overnight.

The contents of the reactor were filtered, and the filter cake was rinsed with a solvent combination of 2-methyltetrahydrofuran and heptanes (67.1 mL, 8 volumes) to provide D-1a. $^1$H NMR (400 MHz, $CDCl_3$): δ 8.34 (br, 1H), 7.83 (s, 1H), 6.63 (m, 2H), 4.53 (s, 2H), 4.12 (s, 2H), 3.34 (s, 3H), 3.10 (s, 6H). $^{13}$C NMR (100 MHz, $CDCl_3$): δ 192.33, 165.85, 163.03, 160.54, 158.00, 110.89, 103.50, 100.05, 76.11, 58.77, 44.74, 30.61. LCMS, Calculated: 330.12, Found: 330.91 (M).

O. Condensation and Cyclization of D-1a to Form F-1a Via E-1a

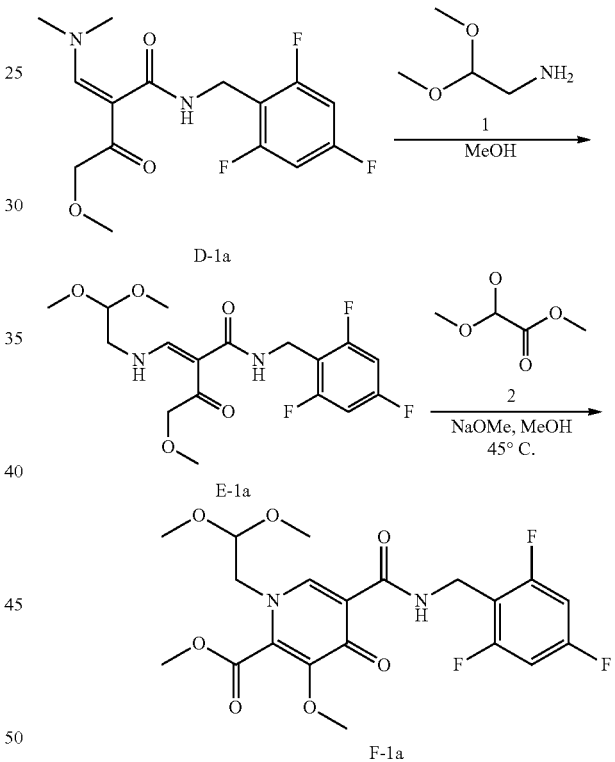

D-1a (70.0 g, 212 mmol, 1.0 equivalent) was charged to an inerted 1 L reactor. To this reactor was then charged methanol (420 mL, 6 volumes) and aminoacetaldehyde dimethylacetal (1, 28.8 mL, 233 mmol, 1.1 equivalent). The reactor jacket temperature was maintained between about 16 and 23° C.

After aging the reaction for about 1-2 hours, dimethyl oxalate (2, 125 g, 1.06 mol, 5.0 equivalents) was charged to the reactor and the reactor jacket temperature was increased to between about 42-48° C. Upon achieving complete dissolution of dimethyl oxalate, the reactor was charged with sodium methoxide as a solution in methanol (84.7 g, 25 wt %, 197 mmol, 1.85 equivalents). The reactor jacket temperature was maintained between about 42-48° C. for about 14-18 h.

Reactor jacket temperature was reduced to about 34-37° C. over the course of about 1 h. Upon reaching a stable temperature in this range, the reactor was charged with F-1a seed crystals (0.350 g, ca. 0.5 wt %) and allowed to age for about 1-2 h. At this point, water (420 mL, 6 volumes) was charged to the reactor over the course of about 2-3 hours. The reactor jacket temperature was reduced to about 18-22° C. over about 1 h.

The resulting slurry was discharged from the reactor, and the solids collected by filtration. Liquors were recycled to displace solids remaining in the reactor. The collected solids on the filter were then washed with a 1:1 mixture of water and methanol (420 mL, 6 volumes), followed by water (420 mL, 6 V). The collected wet cake was dried in a vacuum oven at about 36-42° C. for about 16 h, providing F-1a.

$^1$H NMR (400 MHz, CDCl$_3$): δ 10.28 (t, J=5.5 Hz, 1H), 8.38 (s, 1H), 6.66-6.53 (m, 2H), 4.58 (d, J=5.6 Hz, 2H), 4.43 (t, J=4.7 Hz, 1H), 4.00 (d, J=4.7 Hz, 2H), 3.92 (s, 3H), 3.88 (s, 3H), 3.32 (s, 6H). $^{13}$C NMR (100 MHz, CDCl$_3$): δ 173.08, 163.81, 162.17, 162.14 (ddd, J=249.2, 15.6, 15.6 Hz), 161.72 (ddd, J=250.5, 15.0, 10.9 Hz), 149.37, 144.64, 134.98, 119.21, 110.53 (ddd, J=19.8, 4.7, 4.7 Hz), 102.70, 100.22 (m), 60.68, 56.75, 55.61, 53.35, 30.64. LCMS, Calculated: 458.39, Found: 459.15 (M+H).

P. Acetal Hydrolysis of F-1a to Form FF-1a:

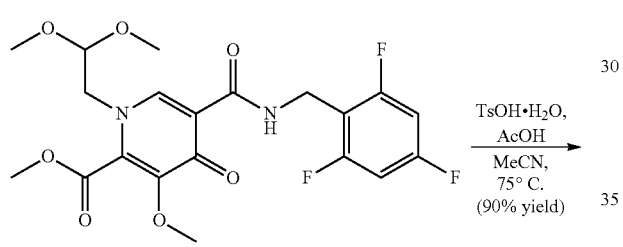

To a solution of F-1a (10.0 g, 1.0 equivalent) and acetonitrile (50 mL) was added p-Toluenesulfonic acid monohydrate (0.414 g, 0.10 equivalent) and acetic acid (16.3 mL, 12 equivalent). The reaction was then heated to about 75° C. and aged for about 8-10 hours. Once the reaction completion was confirmed by HPLC, the reaction was cooled to room temperature and water (60 mL) was added. The mixture was then concentrated under reduced pressure to remove acetonitrile. The resultant slurry was then aged at room temperature for about 2 hours, filtered, washed with water (2×30 mL). The cake was dried in vacuum oven at about 50° C. for about 10 hours to give FF-1a.

$^1$H NMR (400 MHz, DMSO-d$_6$): δ 10.34 (t, J=8.0 Hz, 1H), 8.45 (s, 1H), 7.19 (m, 2H), 6.37 (m, 2H), 4.96 (m, 1H), 4.55 (d, J=4.0 Hz, 2H), 3.95 (m, 2H), 3.93 (s, 3H), 3.79 (s, 3H). $^{13}$C NMR (100 MHz, DMSO-d$_6$): δ 172.32, 163.47, 162.10, 161.93 (dt, J=246, 15.0 Hz), 161.41 (ddd, J=247, 15.0, 11.0 Hz), 148.01, 145.57, 135.84, 118.32, 111.48 (td, J=20.0, 5.0 Hz), 101.17 (m), 87.99, 60.55, 60.50, 53.98, 30.37. LCMS, Calculated: 431.1061, Found: 431.1062 (M+H).

Q. Cyclization of FF-1a and N-1a.BzOH to Form G-1a

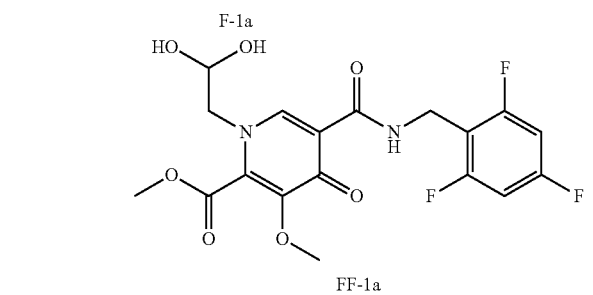

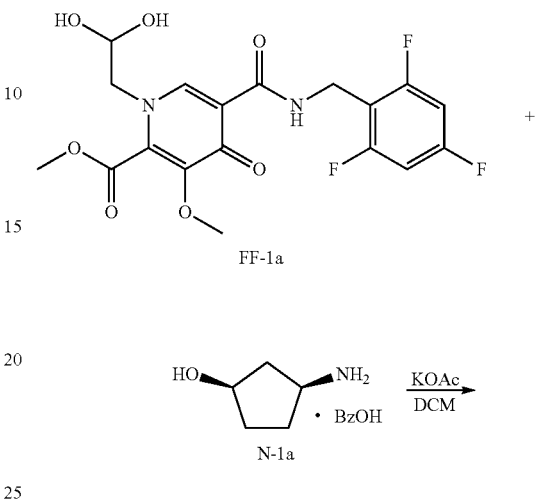

FF-1a (90.0 g, 1.0 equiv), N-1a.BzOH (60.7 g, 1.3 equiv), and potassium acetate (51.3 g, 2.5 equiv) were charged to a reactor. Dichloromethane (DCM, 1.1 L) was charged and the mixture was agitated at about 20° C. until the reaction is complete. A 5% aqueous NaHCO$_3$ solution (540 mL) was charged to the reactor and the mixture was agitated until the solids completely dissolve. The phases were separated and the bottom organic phase was charged back to the reactor. Water (450 mL) was charged to the reactor and the mixture was agitated for about 15 minutes. The phases were separated and the organic phase was distilled to dryness.

The crude G-1a was dissolved in dimethylformamide (DMF, 180 mL) and the resulting solution was charged to a reactor containing water (1.1 L) over about 2 hours, while agitating the water. The product slurry was aged at about 20° C. for about 12 hours and then filtered. The product cake was washed with water (360 mL) and dried to afford G-1a.

$^1$H NMR (400 MHz, CDCl$_3$): δ 10.23 (t, J=5.5 Hz, 1H), 8.39 (s, 1H), 6.60 (t, J=8.1 Hz, 2H), 5.29 (dd, J=9.5, 3.7 Hz, 2H), 4.57 (d, J=5.4 Hz, 3H), 4.33 (dd, J=12.8, 3.8 Hz, 1H), 4.02-3.87 (m, 1H), 3.94 (s, 3H), 2.06-1.88 (m, 4H), 1.78 (dd, J=17.2, 7.5 Hz, 1H), 1.55-1.46 (m, 1H). $^{13}$C NMR (100 MHz, CDCl$_3$): δ 174.53, 163.75, 162.33 (dd, J=249.4, 15.7, 15.7 Hz), 161.86 (ddd, J=250.4, 14.9, 10.9 Hz), 154.18, 154.15, 142.44, 129.75, 118.88, 110.58 (ddd, J=19.8, 4.7, 4.7 Hz), 100.42 (m), 77.64, 74.40, 61.23, 54.79, 51.13, 38.31, 30.73, 29.55, 28.04. LCMS, Calculated: 463.14, Found: 464.15 (M+H).

R. Conversion of (−)-Vince Lactam to b-1a

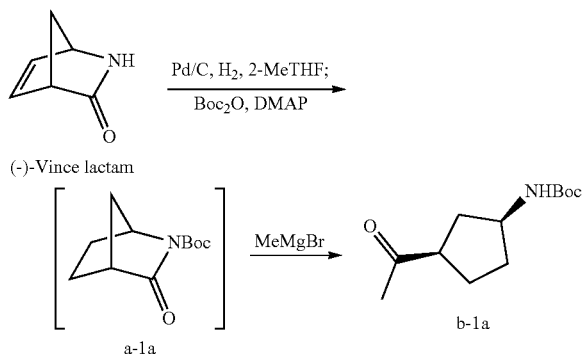

Wet Pd/C (0.138 kg) was charged to a reactor followed by 2-MeTHF (421 kg) and (−)-Vince lactam (55 kg). The vessel was purged with nitrogen followed by hydrogen. The contents were adjusted to about 25 to 35° C. and the hydrogen maintained at about 0.30 to 0.35 MPa. After about 6.5 h, the reaction was deemed complete by HPLC. The contents were filtered through celite (11 kg) and washed with 2-MeTHF (102 kg). The product was obtained in solution.

A solution of Boc$_2$O in 2-MeTHF was prepared as follows: Boc$_2$O (123 kg) was charged to a reactor followed by 2-MeTHF (60 kg). After a solution was achieved, it was discharged into a container and rinsed forward with 2-MeTHF (44.6 kg) and held until further use.

The solution of the product of the hydrogenation was charged to a reactor and concentrated under reduced pressure to about 5 to 6 V at ≤45° C. DMAP (0.34 kg) was charged and the mixture warmed to about 45 to 50° C. The solution of Boc$_2$O was added over approximately 2 h and the mixture allowed to stir for an additional 2 h at the target temperature. After this time, the reaction was deemed complete by HPLC. 2-MeTHF was charged (480 kg) and the solution concentrated under reduced pressure to about 4 to 5 V at about ≤45° C. This process was repeated twice more to remove t-BuOH. 2-MeTHF was charged (278.8 kg) to afford a-1a in solution.

The solution of a-1a was diluted with 2-MeTHF (405.8 kg) and cooled to −10 to 0° C. MeMgBr (35% in 2-MeTHF, 201.3 kg) was added over approximately 6 h to maintain the temperature at about −10 to 0° C. After the addition was complete, the mixture was stirred for an additional approximately 1 to 2 h at which time the reaction was complete as determined by HPLC. 15% aqueous AcOH (350 kg) was added maintaining the temperature at about 0 to 5° C. to adjust the pH to approximately 7. The layers were separated and the organic layer was washed with water twice (726 kg total water used). The organic layer was concentrated to about 4 to 5 V under reduced pressure at about ≤45° C. The solution was azeotroped with 2-MeTHF three times to about 4 to 5 V each time (2810 kg 2-MeTHF used). The final solution was concentrated under reduced pressure to about 2.5 to 3 V. n-Heptane (126 kg) was slowly added maintaining the temperature at 30 to 35° C. b-1a seeds were added (0.7 kg) and the mixture stirred at about 30 to 35° C. for 5 to 10 h. Additional n-heptane was added (200.4 kg) maintaining the temperature at about 30 to 35° C. over approximately 5 h. The contents were distilled under reduced pressure at about ≤45° C. to about 6 to 7 V. Additional n-heptane was added (243.2 kg) maintaining the temperature at about 30 to 35° C. over approximately 1 to 2 h. The contents were distilled under reduced pressure at about ≤45° C. to about 6 to 7 V. Additional n-heptane was added (241.4 kg) maintaining the temperature at about 30 to 35° C. over approximately 1 to 2 h. The contents were distilled under reduced pressure at about ≤45° C. to about 6 to 7 V. Additional n-heptane was added (253.6 kg) maintaining the temperature at about 30 to 35° C. over approximately 1 to 2 h. The contents were cooled to about −5 to 0° C. and held for approximately 1 to 2 h. Product was collected by filtration, washed with n-heptane (187 kg) at about −5 to 0° C., and dried under reduced pressure at about 40 to 45° C. to afford single enantiomer b-1a.

S. Conversion of b-1a to cc-1a

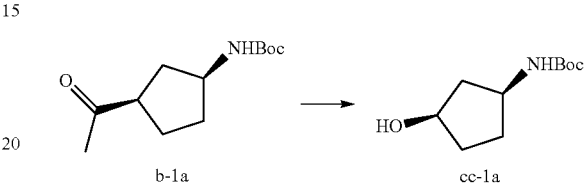

b-1a (90.9 kg) and toluene (822 kg) were charged to a reactor and stirred at 25 to 30° C. to achieve a solution. m-CPBA (174 kg) was charged into the reactor in 5 portions (4 to 6 h between additions). The reaction was allowed to stir at about 25 to 30° C. until the reaction was deemed complete by HPLC (approximately 10 to 20 h). 20% NaHSO$_3$ (428 kg) was added maintaining the temperature about below 30° C. and the mixture stirred until negative with starch potassium iodide paper. 10% NaOH (698 kg) was added maintaining the temperature about below 30° C. The mixture was stirred for approximately 30 to 60 min. The organic layer was washed with water (500 kg) and the organic layer concentrated under reduced pressure at about ≤45° C. to 5 to 6 V. The temperature was adjusted to 15 to 25° C. to afford the oxidized product in solution.

Water (90 kg), methanol (70 kg), and LiOH.H$_2$O (29.5 kg) were added to the solution of the oxidized product and the mixture stirred at 25 to 30° C. for 3 to 6 h at which time the reaction was deemed complete by HPLC. Toluene (390 kg) and 25% NaCl (278 kg) were added to the mixture and stirred for about 30 to 60 min. The layers were separated and 20% NaCl (259 kg) were added to the organic layer. The pH of the solution was adjusted to about 7 to 8 with 1 N HCl (7.6 kg) and the layers separated. The organic layer was washed with 20% NaCl (259.4 kg). The organic layer was filtered and concentrated under reduced pressure at about ≤45° C. to about 4.5 to 5.5 V. Toluene (385.6 kg) was charged and the distillation/toluene addition were repeated until KF≤0.05%. Toluene (385.3 kg) was charged followed by active carbon (6.5 kg). The mixture was warmed to about 30 to 40° C. and stirred for about 2 to 6 h. The contents were cooled, filtered through celite (6.3 kg), and washed with toluene (146 kg). The filtrate was concentrated under reduced pressure at about ≤45° C. to about 1.5 to 1.6 V. The mixture was stirred for about 30 to 60 min at about 30 to 35° C. n-Heptane (87 kg) was charged over about 1 to 2 h and the mixture seeded with cc-1a (0.516 kg) and stirred for an additional 2 to 3 h. n-Heptane (286.4 kg) was slowly charged and stirred for about 2 to 3 h. The mixture was cooled to about 10 to 15° C. and stirred for an additional about 3 to 5 h. The product was collected by filtration and washed with n-heptane (40 kg) at about 10 to 15° C. The product was dried under reduced pressure at about 35 to 45° C. to afford single enantiomer cc-1a.

T. Classical Resolution of c-1a

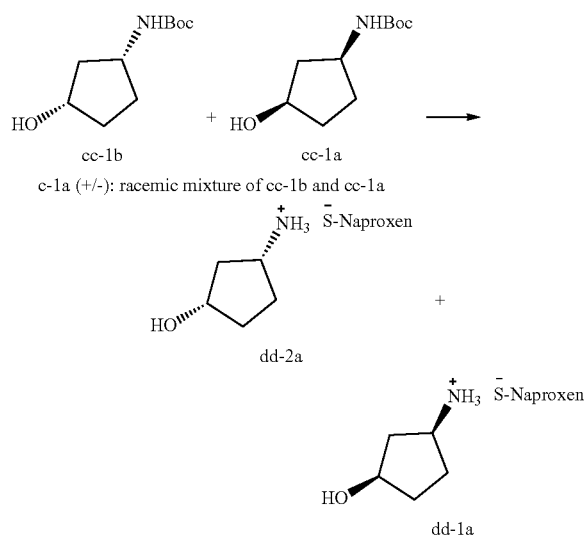

A vessel was charged with c-1a (10.0 g, 1 equivalent), (S)-Naproxen (11.5 g, 1.03 mmol) and water (200 mL). The mixture was refluxed overnight, after which the mixture had turned dark. Removal of the solvent by rotary evaporation yielded the desired salt as a brown solid. The mixture of dd-2a and dd-1a (3.0 g) was suspended in MEK (50 mL) and the mixture was heated to reflux. Water was added (4 mL). The mixture was allowed to cool to room temperature. The solid was isolated by filtration, dried and recrystallized from 10% water in MEK (30 mL) to afford dd-1a which showed an optical purity >90% ee.

U. Classical Resolution of c-1a

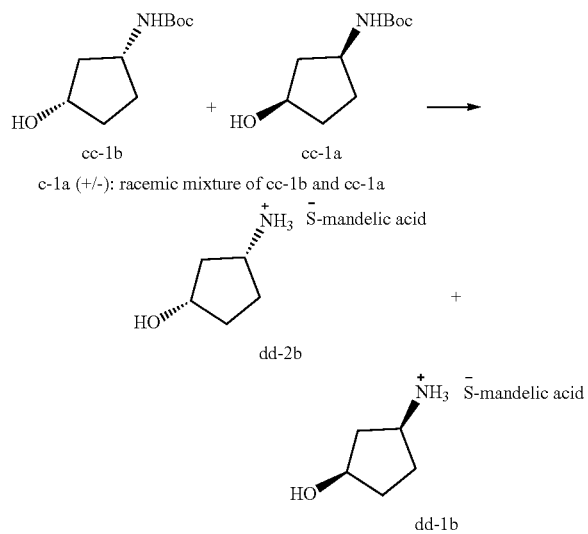

To a solution of c-1a (89.7 mgs, 1.0 equiv) in IPA (0.9 mL) was quickly added a solution of S-(+)-mandelic acid (134.9 mgs, 1.0 equiv) in IPA (0.9 mL). The mixture was stirred at approximately room temperature and solid precipitate was observed after approximately 20 minutes. The slurry was stirred for an additional 15 minutes, and the solids were filtered and collected. The solids obtained from the initial salt formation were recrystallized in IPA and was slowly cooled from approximately 80° C. to approximately 0° C. to provide the enantioenriched product dd-1b.

V. Enzymatic Resolution of c-1a—Selective Acylation

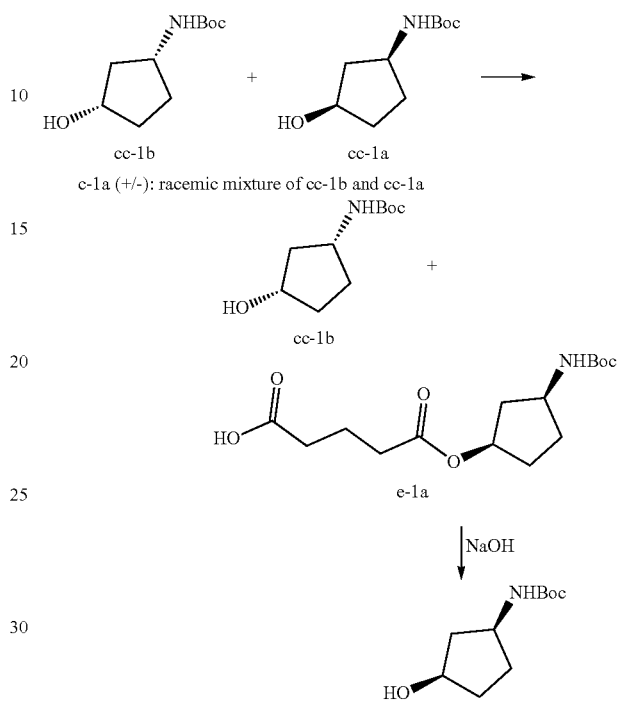

Toluene (500 mL) was added to a reaction vessel followed by c-1a (50 g, 1 eq.). Glutaric anhydride (28.4 g, 1 eq.) was added followed by Novozyme 435 (7.5 g, 15 wt %). The reaction was allowed to stir for approximately 23 h at approximately 10 to 15° C. Additional Novozyme (2.5 g, 5 wt %) was charged and the reaction allowed to proceed for approximately 12 h at approximately 10 to 15° C. Solids were removed by filtration and rinsed with toluene (100 mL). The organic phase was washed with 10% $Na_2CO_3$ (250 mL) followed by 5% $Na_2CO_3$ (250 mL). The combined aqueous phases were washed with MTBE (2×500 mL). THF (150 mL) was added to the resulting aqueous phase followed by sodium hydroxide (14.9 g, 3 equivalents). The mixture was allowed to stir for approximately 4 h at approximately 15 to 20° C. The layers were separated, and the THF layer was concentrated. The aqueous layer was extracted with dichloromethane (2×250 mL). The residue from the THF layer was dissolved in the combined dichloromethane, and the mixture washed with water (250 mL). The organic phase was concentrated to approximately 100 mL and water (300 mL) was added. The mixture was further concentrated to approximately 250 mL at approximately 55 to 60° C. The mixture was cooled to approximately 47° C. over approximately 1 h, seeds of the product (200 mg) were added and the mixture aged for approximately 1 h at approximately 45 to 47° C. The mixture was cooled to approximately 25° C. over approximately 2 h and aged approximately 0.5 h. The solids were collected by filtration and washed with water (50 mL). The product was dried at approximately 35 to 40° C. under vacuum to afford the desired product cc-1a (>95% ee).

W. Enzymatic Resolution of c-1a—Selective Hydrolysis

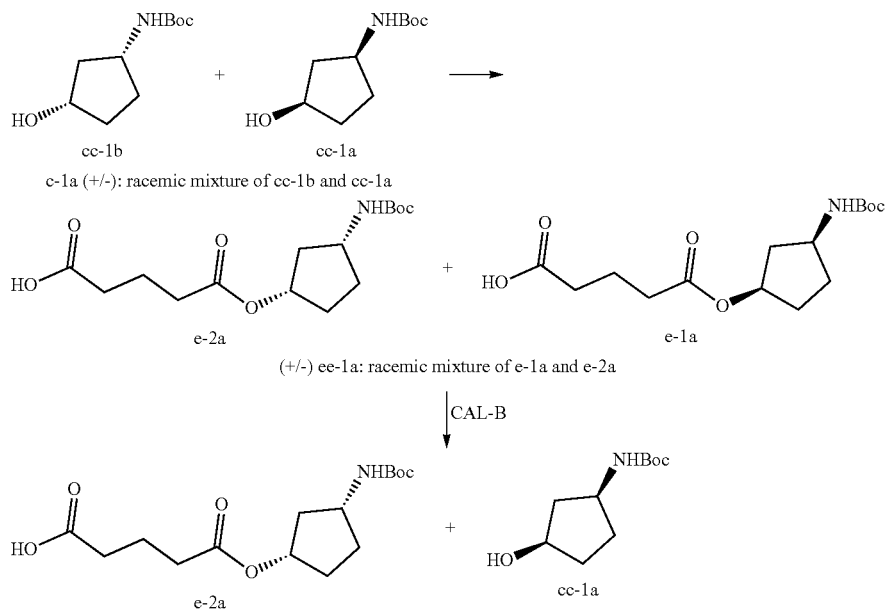

A mixture of compound c-1a (50 g, 1 eq.), glutaric anhydride (42.5 g, 1.5 eq.) and DMAP (50 mg, 0.001 eq.) in 300 mL pyridine was stirred overnight at approximately 60° C. The reaction mixture was evaporated to dryness. Subsequently the residue was dissolved in DCM (250 mL) and washed with 3×250 mL 0.2 M HCl (aq.). The organic layer was evaporated to dryness. The residue was stirred with 300 mL water and the pH was adjusted to 7.8 with approximately 300 mL 2 M NaOH solution. The water layer was washed with DCM (3×70 mL). The water layer was then acidified to pH 4 with 3 N HCl(aq) and extracted with DCM (4×150 mL and 2×100 mL). The combined organic layers were dried over $Na_2SO_4$, filtered and evaporated, yielding a colorless oil which crystalized upon standing. Trituration with pentane (~100 mL) followed by filtration and drying under vacuum yielded racemic ee-1a.

Racemic ee-1a (1.008 g) was suspended in diisopropyl ether (10 mL). To the suspension was added 200 mM sodium phosphate buffer pH 7 (20 mL) and Cal-B (0.2 g). The reaction mixture was shaken at 250 rpm, 30° C. for ~100 h (>80% ee observed after 91.5 h). The reaction mixture was filtered and the layers of the filtrate were separated. The solid was washed with DCM (2×10 mL). The filtrate was used to extract the aqueous layer. The aqueous layer was extracted a second time with DCM (10 mL). The combined organic layers were washed with 5% $Na_2CO_3$ (2×20 mL), brine (10 mL) and dried over $Na_2SO_4$. Filtration and evaporation of the volatiles under reduced pressure afforded the desired product cc-1a.

X. Allylic Amination of f-1a to Form g-1a

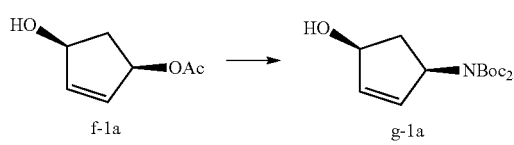

Triphenylphosphine (0.37 g, 0.02 eq) and $Pd_2(dba)_3$ (0.32 g, 0.005 eq) were mixed in degassed THF (200 mL) at approximately room temperature for approximately 20 min. f-1a (10 g, 1 eq, single enantiomer), $Cs_2CO_3$ (46 g, 2 eq) and di-tert-butyl iminodicarboxylate (16.05 g, 1.05 eq) were added and the mixture heated to 50° C. for approximately 18 h. The mixture was cooled and water (100 mL) and ethyl acetate (50 mL) were added. The layers were separated and the organic phase was washed 2× ethyl acetate. The combined organics were dried over sodium sulfate and concentrated to dryness. The residue was purified by silica gel column chromatography (0 to 40% ethyl acetate in hexane). The isolated material was dissolved in MeTHF, washed with 5% aq. KOH, concentrated, and purified by silica gel column chromatography (0 to 10% methanol in dichloromethane) to provide the desired product g-1a.

Y. Hydrogenation of g-1a to Form h-1a

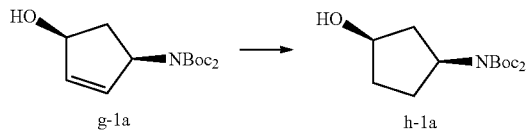

g-1a (1.0 g) and $PtO_2$ (0.008 g) were combined in isopropanol (10 mL). The vessel was flushed with $H_2$ gas and stirred under an atmosphere of hydrogen at approximately room temperature for approximately 18 h. The mixture was filtered through celite and used without further purification in the subsequent deprotection.

Z. Deprotection of h-1a to Form N-1a

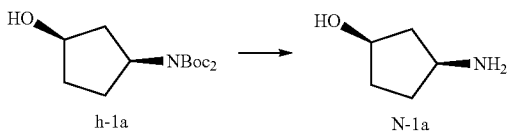

Acetyl chloride (1.7 mL, 7 eq) was combined with isopropanol (5 mL) and stirred at approximately room temperature for approximately 15 min to generate HCl in isopropanol. Crude starting material h-1a in isopropanol (2.5 mL) was added and rinsed forward with isopropanol (2.5 mL). After approximately 18 h, the slurry was cooled to approximately 0° C. and N-1a was collected by filtration. $^1$H NMR (CD$_3$OD) confirmed the desired product was isolated.

Each of the references including all patents, patent applications and publications cited in the present application is incorporated herein by reference in its entirety, as if each of them is individually incorporated. Further, it would be appreciated that, in the above teaching of invention, the skilled in the art could make certain changes or modifications to the invention, and these equivalents would still be within the scope of the disclosure defined by the appended claims of the application.

The invention claimed is:

1. A process to prepare a compound of Formula I:

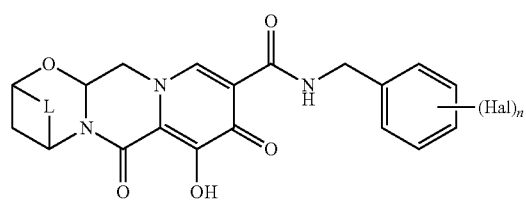

according to the following General Scheme VI

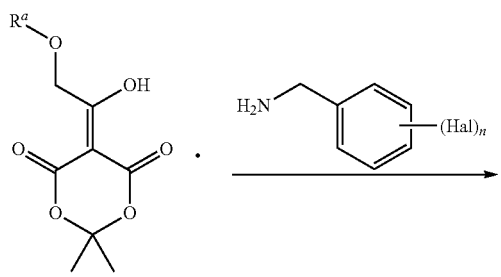

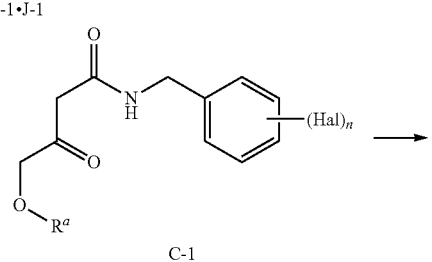

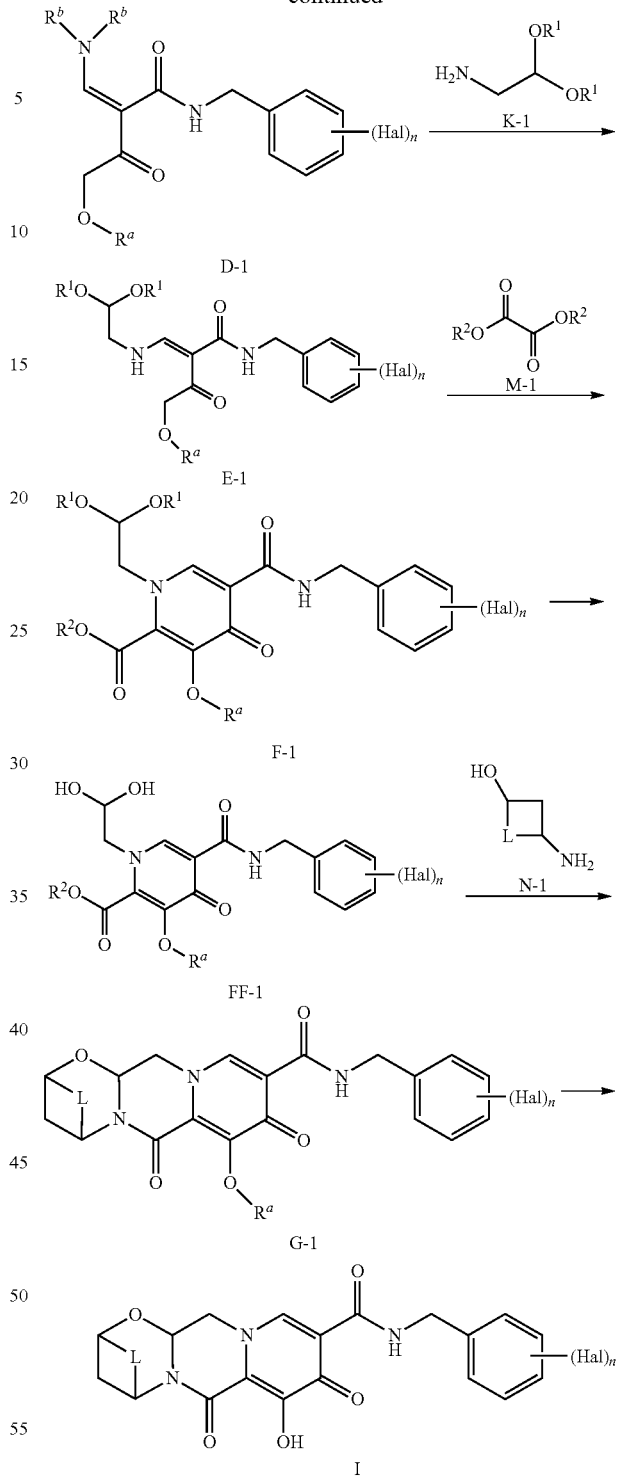

wherein the process comprises the following steps:
reacting B-1.J-1 in the presence of an acid to yield C-1;
reacting C-1 with an alkylated formamide acetal to yield D-1;
reacting D-1 with K-1 to yield E-1;
reacting E-1 with M-1 in the presence of a base to yield F-1;
reacting F-1 with at least one acid to yield FF-1;

reacting FF-1 with N-1, or a salt or a co-crystal thereof, in the presence of an additive selected from the group consisting of a carboxylate salt, an inorganic carbonate, a metal hydride, an alkoxide, a water scavenger and a mixture thereof to yield G-1; and reacting G-1 with at least one reagent selected from the group consisting of metal salts, Lewis acids, sodium ethanethiolate, sodium hexamethyldisiloxane, trifluoroacetic acid, and combinations thereof to yield a compound of Formula I;

wherein

Hal is halogen, which may be the same or different,
n is 1, 2, or 3,
L is —C(R$^c$)$_2$—, —C(R$^c$)$_2$C(R$^c$)$_2$—, —C(R$^c$)$_2$C(R$^c$)$_2$C(R$^c$)$_2$—, or —C(R$^c$)$_2$C(R$^c$)$_2$C(R$^c$)$_2$C(R$^c$)$_2$—,
each R$^c$ is, independently, hydrogen, halo, hydroxyl or C$_1$-C$_4$alkyl,
each R$^a$, R$^1$, and R$^2$ is, independently, (C$_1$-C$_4$)alkyl, (C$_6$-C$_{10}$)aryl, or (C$_6$-C$_{10}$)aryl (C$_1$-C$_4$)alkyl; and
each R$^b$ is independently (C$_1$-C$_4$)alkyl.

2. The process of claim 1 wherein B1.J-1 is reacted in the presence of an acid selected from the group consisting of an inorganic acid, an organic acid, a halogenated organic acid, a Lewis acid and mixtures thereof.

3. The process of claim 2 wherein the acid is selected from the group consisting of hydrochloric acid, hydrobromic acid, hydroiodic acid, trifluoromethanesulfonic acid, formic acid, trifluoroacetic acid, trichloroacetic acid, perfluoropropionic acid, dichloroacetic acid, chloroacetic acid, acetic acid, para-toluenesulfonic acid, methane sulfonic acid, zinc chloride, magnesium bromide, magnesium triflate, copper triflate, scandium triflate, and a mixture thereof.

4. The process of claim 3 wherein the acid is trifluoroacetic acid.

5. The process of claim 1 wherein the alkylated formamide acetal is selected from the group consisting of N,N-dimethylformamide dimethyl acetal, N,N-dimethylformamide diethyl acetal, N,N-dimethylformamide diisopropyl acetal, N,N-diethylformamide dimethyl acetal, and N,N-diisopropylformamide dimethyl acetal.

6. The process of claim 5 wherein the alkylated formamide acetal is N,N-dimethylformamide dimethyl acetal.

7. The process of claim 1 wherein C-1 is reacted with an alkylated formamide acetal in the presence of an acid.

8. The process of claim 7 wherein the acid is selected from the group consisting of trifluoroacetic acid, formic acid, acetic acid, sulfuric acid trifluoroacetic acid, trichloroacetic acid, and perfluoropropionic acid.

9. The process of claim 8, wherein the acid is trifluoroacetic acid.

10. The process of claim 1 wherein K-1 is selected from the group consisting of aminoacetaldehyde diethylacetal, aminoacetaldehyde dipropylacetal, aminoacetaldehyde dimethylacetal, and aminoacetaldehyde dibutalacetal.

11. The process of claim 10 wherein K-1 is aminoacetaldehyde dim ethyl acetal.

12. The process of claim 1 wherein M-1 is selected from the group consisting of dimethyl oxalate, diethyl oxalate, dipropyl oxalate, and dibutyl oxalate.

13. The process of claim 12 wherein M-1 is dimethyl oxalate.

14. The process of claim 1 wherein E-1 is reacted with M-1 in the presence of a base selected from the group consisting of a metal hydride, an alkoxide, an inorganic carbonate, a bis(trialkylsilyl)amide base, and a mixture thereof.

15. The process of claim 14 wherein the base is selected from the group consisting of sodium hydride, potassium hydride, lithium hydride, sodium methoxide, sodium tert-butoxide, sodium ethoxide, potassium tert-butoxide, potassium ethoxide, sodium tert-pentoxide, lithium tert-butoxide, lithium bis(trimethylsilyl)amide, sodium bis(trimethylsilyl)amide, potassium bis(trimethylsilyl)amide, lithium carbonate, sodium carbonate, potassium carbonate, cesium carbonate, and a mixture thereof.

16. The process of claim 15, wherein the base is sodium methoxide.

17. The process of claim 1 wherein F-1 is reacted with at least one acid selected from the group consisting of an organic acid, an inorganic acid, an organic carboxylic acids, and mixtures thereof.

18. The process of claim 17 wherein the at least one acid is selected from the group consisting of methanesulfonic acid, acetic acid, trifluoromethanesulfonic acid, trifluoroacetic acid, hydrochloric acid, hydrobromic acid, sulfuric acid, nitric acid, phosphoric acid, formic acid, butyric acid, propionic acid, benzoic acid, p-Toluenesulfonic acid, camphorsulfonic acid, and mixtures thereof.

19. The process of claim 18, wherein the at least one acid is p-toluenesulfonic acid.

20. The process of claim 1 wherein L is —CH$_2$—CH$_2$—.

21. The process of claim 1 wherein N-1 is

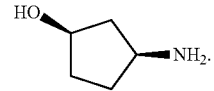

22. The process of claim 1 wherein N-1 is in the form of a salt or co-crystal.

23. The process of claim 22 wherein N-1 is

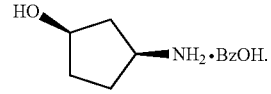

24. The process of claim 1 wherein N-1 is in solution.

25. The process of claim 1 wherein the additive is selected from the group consisting of lithium carbonate, sodium carbonate, potassium carbonate, cesium carbonate, sodium hydride, potassium hydride, lithium hydride, sodium methoxide, sodium tert-butoxide, sodium ethoxide, potassium tert-butoxide, potassium ethoxide, sodium tert-pentoxide, lithium tert-butoxide, sodium propionate, potassium propionate, molecular sieves, trimethyl orthoacetate, potassium acetate, sodium acetate, lithium acetate and trimethyl orthoformate.

26. The process of claim 25 wherein the additive is potassium acetate.

27. The process of claim 1, wherein the at least one reagent is selected from the group consisting of magnesium bromide, lithium chloride, lithium bromide, lithium iodide, aluminum trichloride, aluminum tribromide, chlorotrimethylsilane, iodotrimethylsilane, boron trichloride, boron tribromide, sodium ethanethiolate, sodium hexamethyldisiloxane, palladium, boron trifluoride diethyl etherate, and trifluoroacetic acid.

28. The process of claim 27, wherein the at least one reagent is magnesium bromide.

29. The process of claim 1 wherein each $R^a$, $R^b$, $R^1$, and $R^2$ is, independently $(C_1\text{-}C_4)$alkyl.

30. The process of claim 29 wherein $R^2$ is —$CH_3$.

31. The process of claim 29 wherein $R^1$ is —$CH_3$.

32. The process of claim 29 wherein $R^a$ is —$CH_3$.

33. The process of claim 29 wherein $R^b$ is —$CH_3$.

34. The process of claim 1 wherein each Hal is independently —F or —Cl.

35. The process of claim 34 wherein Hal is F.

36. The process of claim 1 wherein n is 3.

37. The process of claim 1 wherein J-1 is

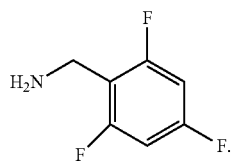

38. The process of claim 18, wherein the at least one acid is formic acid.

39. The process of claim 27, wherein the at least one reagent is lithium chloride.

* * * * *